US008318172B2

(12) United States Patent
Grunewald et al.

(10) Patent No.: US 8,318,172 B2
(45) Date of Patent: *Nov. 27, 2012

(54) BREAKING IMMUNOLOGICAL TOLERANCE WITH A GENETICALLY ENCODED UNNATURAL AMINO ACID

(75) Inventors: Jan Grunewald, San Diego, CA (US); Meng-Lin Tsao, Merced, CA (US); Roshan Perera, Arlington, TX (US); Richard A. Lerner, La Jolla, CA (US); Vaughn V. Smider, San Diego, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 559 days.

This patent is subject to a terminal disclaimer.

(21) Appl. No.: 12/322,938

(22) Filed: Feb. 7, 2009

(65) Prior Publication Data

US 2009/0263376 A1  Oct. 22, 2009

Related U.S. Application Data

(60) Provisional application No. 61/065,148, filed on Feb. 8, 2008, provisional application No. 61/065,147, filed on Feb. 8, 2008, provisional application No. 61/065,515, filed on Feb. 12, 2008, provisional application No. 61/065,590, filed on Feb. 12, 2008, provisional application No. 61/135,947, filed on Jul. 25, 2008, provisional application No. 61/135,969, filed on Jul. 25, 2008, provisional application No. 61/137,676, filed on Jul. 31, 2008, provisional application No. 61/137,635, filed on Jul. 31, 2008, provisional application No. 61/203,948, filed on Dec. 29, 2008, provisional application No. 61/203,947, filed on Dec. 29, 2008.

(51) Int. Cl.
*A61K 39/00* (2006.01)

(52) U.S. Cl. .................................................. 424/184.1

(58) Field of Classification Search .................. None
See application file for complete search history.

(56) References Cited

U.S. PATENT DOCUMENTS

| | | | |
|---|---|---|---|
| 6,927,042 B2 | 8/2005 | Schultz et al. | |
| 7,045,337 B2 | 5/2006 | Schultz et al. | |
| 7,083,970 B2 | 8/2006 | Schultz et al. | |
| 7,129,333 B2 | 10/2006 | Schultz et al. | |
| 7,183,082 B2 | 2/2007 | Schultz et al. | |
| 7,199,222 B2 | 4/2007 | Schultz et al. | |
| 7,217,809 B2 | 5/2007 | Schultz et al. | |
| 7,238,510 B2 | 7/2007 | Schultz et al. | |
| 7,262,040 B2 | 8/2007 | Schultz et al. | |
| 7,632,492 B2 * | 12/2009 | Grabstein et al. | 424/85.6 |
| 2004/0198637 A1 | 10/2004 | Schultz et al. | |
| 2004/0265952 A1 | 12/2004 | Deiters et al. | |
| 2005/0009049 A1 | 1/2005 | Chin et al. | |
| 2005/0136513 A1 | 6/2005 | Zhang et al. | |
| 2005/0208536 A1 | 9/2005 | Schultz et al. | |
| 2005/0227318 A1 | 10/2005 | Alfonta et al. | |
| 2005/0250183 A1 | 11/2005 | Schultz et al. | |
| 2005/0272121 A1 | 12/2005 | Xie et al. | |
| 2006/0019347 A1 | 1/2006 | Cho et al. | |
| 2006/0063244 A1 | 3/2006 | Schultz et al. | |
| 2006/0073507 A1 | 4/2006 | Deiters et al. | |
| 2006/0110784 A1 | 5/2006 | Deiters et al. | |
| 2006/0110796 A1 | 5/2006 | Schultz et al. | |
| 2006/0134746 A1 | 6/2006 | Deiters et al. | |
| 2006/0160175 A1 | 7/2006 | Anderson et al. | |
| 2006/0177900 A1 | 8/2006 | Anderson et al. | |
| 2006/0246509 A1 | 11/2006 | Deiters et al. | |
| 2007/0009990 A1 | 1/2007 | Alfonta et al. | |
| 2007/0020634 A1 | 1/2007 | Anderson et al. | |
| 2007/0042461 A1 | 2/2007 | Anderson et al. | |
| 2007/0111193 A1 | 5/2007 | Zhang et al. | |
| 2007/0117184 A1 | 5/2007 | Schultz et al. | |
| 2007/0154952 A1 | 7/2007 | Chin et al. | |
| 2007/0166791 A1 | 7/2007 | Chin et al. | |
| 2007/0172915 A1 | 7/2007 | Schultz et al. | |
| 2007/0178448 A1 | 8/2007 | Tsao et al. | |
| 2007/0184517 A1 | 8/2007 | Schultz et al. | |
| 2007/0238152 A1 | 10/2007 | Wang et al. | |
| 2007/0281335 A1 | 12/2007 | Ryu et al. | |

FOREIGN PATENT DOCUMENTS

WO  WO 2007075438 A2 *  7/2007
WO  WO 2007/094916 A2  8/2007

OTHER PUBLICATIONS

Thomas et al. "Nature of T Lymphocyte Recognition of Macrophage-Assocaited Antigens V. Contribution of Individual Peptide Residues of Human Fibrinopeptide B to T Lymphocte Responses" *J. Exp. Med.*, 152 (Sep. 1980) pp. 620-632.*
GenBank: CAA68530.1. tnf-alpha [*Mus musculus*]. Nov. 14, 2006, p. 1.*
NCBI Reference Sequence: NP_038721.1 for tumor necrosis factor [*Mus musculus*], pp. 1-3.* NCBI GenBank Reference Sequence: AAA61200.1 for tumor necrosis factor [*Homo sapiens*], p. 1.*
Bäcklund et al. (2002) "Glycosylation of Type II collagen is of major importance for T cell tolerance and pathology in collagen-induced arthritis." *Eurpean Journal of Immunology*, 32(12): 3776-3784.
Berd (2004) "M-Vax™: an autologous, hapten-modified vaccine for human cancer." *Expert Review of Vaccines*, 3(5): 521-547.
Cantaert et al. (2006) "Citrullinated proteins in rheumatoid arthritis: crucial . . . but not sufficient!" *Arthritis Rheumatism*, 54(11): 3381-3389.
Dalum et al. (1999) "Therapeutic antibodies elicited by immunization against TNF-alpha." *Nature Biotechnology*, 17(7): 666-669.
Dzhambazov et al. (2005) "The major T cell epitope on type II collagen is glycosylated in normal cartilage but modified by arthritis in both rats and humans." *European Journal of Immunology*, 35(2): 357-366.
Grünewald et al. (2008) "Immunochemical termination of self-tolerance." *Proceedings of the National Academy of Sciences, USA*, 105(32): 11276-11280.

(Continued)

*Primary Examiner* — Maher Haddad
*Assistant Examiner* — James Rogers
(74) *Attorney, Agent, or Firm* — Quine Intellectual Property Law Group, P.C.

(57) ABSTRACT

The present invention comprises methods and compositions for producing and/or enhancing an immunological response in a subject against a target moiety such as a disease-related moiety by administration of an antigenic version of the target moiety having one or more unnatural amino acid and/or by administration of an antibody against a version of a target moiety having one or more unnatural amino acid which antibody is cross reactive with the natural target moiety.

20 Claims, 28 Drawing Sheets

OTHER PUBLICATIONS

Grünewald et al. (2009) "Mechanistic studies of the immunochemical termination of self-tolerance with unnatural amino acids." *Proceedings of the National Academy of Sciences, USA*, 106(11): 4337-4342.

Hardy et al. (2008) "Conversion of tyrosine to the inflammation-associated analog 3'-nitrotyrosine at either TCR- or MHC-contact positions can profoundly affect recognition of the MHC class I-restricted epitope of lymphocytic choriomeningitis virus glycoprotein 33 by CD8 T Cells." *Journal of Immunology*, 180(9): 5956-5962.

Le Buanec et al. (2006) "TNFalpha kinoid vaccination-induced neutralizing antibodies to TNFalpha protect mice from autologous TNFalpha-driven chronic and acute inflammation." *Proceedings of the National Academy of Sciences, USA*, 105(51): 19442-19447.

Lerner and Dixon (1968) "The Induction of Acute Glomerulonephritis in Rabbits with Soluble Antigens Isolated from Normal Homologous and Autologous Urine." *Journal of Immunology*, 100(6): 1277-1287.

Loetscher et al. (1993) "Human tumor necrosis factor alpha (TNF alpha) mutants with exclusive specifity for the 55-kDa TNF receptors." *Journal of Biological Chemistry*, 268(35): 26350-26357.

Nakamura and Weigle (1967) "In vivo behavior of homologous and heterologous thyroglobulin and induction of immunologic unresponsiveness to heterologous thryglobulin." *The Journal of Immunology*, 98(4): 653-662.

Nakamura and Weigle (1967) "Induction, maintenance and termination of immunologic unresponsiveness to bovine thyroglobulin in rabbits." *The Journal of Immunology*, 99(2): 357-366.

Nakamura and Weigle (1968) "Isoantigens of Thyroglobulin and Their Significance in Experimental Autoimmune Thyroiditis." *The Journal of Immunology*, 101: 876-884.

Spohn et al. (2007) "A virus-like particle-based vaccine selectively targeting soluble TNF-alpha protects from arthritis without inducing reactivation of latent tuberculosis." *The Journal of Immunology*, 178(11): 7450-7457.

Tsao et al. (2006) "The Genetic Incorporation of a Distance Probe into Proteins in *Escherichia coli.*" *The Journal of the American Chemistry Society*, 128: 4572-4573.

Van Ostade et al. (1994) "Structure-activity studies of human tumour necrosis factors." *Protein Engineering*, 7(1): 5-22.

Weigle (1965) "The Induction of Autoimmunity in Rabbits Following Injection of Heterologous or Altered Homologous Thyroglobin." *Journal of Experimental Medicine*, 121: 289-308.

Weigle (1965) "The production of thyroiditis and antibody following injection of unaltered thyroglobulin without adjuvant into rabbits previously stimulated with altered thyrogobulin." *Journal of Experimental Medicine*, 122: 1049-1062.

Weigle and Nakamura (1967) "The development of autoimmune thyroiditis in rabbits following injection of aqueous preparations of heterologous thyroglobulins." *The Journal of Immunology*, 99(1): 223-231.

Zuany-Amorim et al. (2004) "Induction of TNF-alpha autoantibody production by AutoVac TNF106: a novel therapeutic approach for the treatment of allergic diseases." *International Archives of Allergy Immunology*, 133(2): 154-163.

Zhang et al. (1992) "Site-directed Mutational Analysis of Human Tumor Necrosis Factor-α Receptor Binding Site and Structure-Functional Relationship." *The Journal of Biological Chemistry*, 267(33): 24069-24075.

Baeyens et al. (1999) "The structure of mouse tumor-necrosis factor at 1.4 A resolution: toward modulation of its selectivity and trimerization." *Biological Crystallography*, D55: 772-778.

Blanchet et al. (2001) "A New Generation of Melan-A.MART-1 Peptides That Fulfill Both Increased Immunogenicity and High Resistance to Biodegradation: Implication for Molecular Anti-Melanoma Immunotherapy." *Journal of Immunology*, 167: 5852-5861.

Database XP-002670071: Kurtis et al. (2007) "Photo-reactive and non-natural amino acid Epitopes of human WT1 enhance immunogenicity and allow kinetic study of antigen processing." BIOSIS Database pp. 1-4.

European Search Report for EP Application No. 09708010.5, dated Mar. 2, 2012.

GenBank Reference No. CAA26669.1.

Magliery (2005) "Unnatural Protein Engineering: Producing Proteins with Unnatural Amino Acids." *Medicinal Chemistry Reviews*, 2: 303-323.

Tsao et al. (2006) "The Genetic Incorporation of a Distance Probe into Proteins in *Escherichia coli.*" *Journal of the American Chemistry Society*, 128: 4572-4573.

* cited by examiner

SEQ ID NO: 9

| y-series ions | observed mass (Da) | calculated mass (Da) |
|---|---|---|
| $[y_1]^+$ | 147.0 | 147.1 |
| $[y_2]^+$ | 276.1 | 276.2 |
| $[y_2-H_2O]^+$ | 258.1 | 258.1 |
| $[y_2-NH_3]^+$ | 259.2 | 259.1 |
| $[y_3]^+$ | 404.4 | 404.2 |
| $[y_3-H_2O]^+$ | 386.2 | 386.2 |
| $[y_4]^+$ | 596.3 | 596.3 |
| $[y_5]^+$ | 683.3 | 683.3 |
| $[y_5-H_2O]^+$ | 665.4 | 665.3 |
| $[y_5-H_2O]^{2+}$ | 333.1 | 333.1 |
| $[y_5-NH_3]^+$ | 666.3 | 666.3 |
| $[y_6]^+$ | 796.3 | 796.4 |
| $[y_6]^{2+}$ | 398.9 | 398.7 |
| $[y_6-H_2O]^+$ | 778.3 | 778.4 |
| $[y_6-NH_3]^+$ | 779.5 | 779.4 |
| $[y_7]^+$ | 867.3 | 867.4 |
| $[y_7]^{2+}$ | 434.2 | 434.2 |
| $[y_7-H_2O]^+$ | 849.6 | 849.4 |
| b-series ions | observed mass (Da) | calculated mass (Da) |
| $[b_2]^+$ | 218.9 | 219.1 |
| $[b_3]^+$ | 332.0 | 332.2 |
| $[b_4]^+$ | 419.1 | 419.2 |
| $[b_4-H_2O]^+$ | 401.1 | 401.2 |
| $[b_4-H_2O]^{2+}$ | 201.1 | 201.1 |
| $[b_5]^+$ | 611.3 | 611.3 |
| $[b_5]^{2+}$ | 305.9 | 306.1 |
| $[b_5-H_2O]^+$ | 593.2 | 593.3 |
| $[b_6]^+$ | 739.4 | 739.3 |
| $[b_6-H_2O]^+$ | 721.3 | 721.3 |
| $[b_7]^+$ | 868.3 | 868.4 |
| $[b_7-H_2O]^+$ | 850.3 | 850.4 |
| $[b_7-NH_3]^+$ | 851.1 | 851.4 |
| $[b_7]^+$ | 868.3 | 868.4 |
| $[b_7-H_2O]^+$ | 850.4 | 850.4 |

| y-series ions | Observed mass, Da | Calculated mass, Da |
|---|---|---|
| $[y_3]^+$ | 346.3 | 346.2 |
| $[y_5]^+$ | 530.4 | 530.4 |
| $[y_6]^+$ | 722.5 | 722.4 |
| $[y_7]^+$ | 908.6 | 908.5 |
| $[y_8]^+$ | 1021.6 | 1021.6 |
| $[y_9]^+$ | 1078.7 | 1078.6 |
| $[y_9]^{2+}$ | 540.0 | 539.8 |
| $[y_{10}]^+$ | 1165.7 | 1165.6 |
| $[y_{10}]^{2+}$ | 583.6 | 583.3 |
| b-series ions | | |
| $[b_2]^+$ | 235.2 | 235.1 |
| $[b_3]^+$ | 292.1 | 292.1 |
| $[b_9]^+$ | 1038.5 | 1038.5 |
| $[b_{10}]^{2+}$ | 583.6 | 583.8 |

| y-series ions | Observed mass, Da | Calculated mass, Da |
|---|---|---|
| $[y_2]^+$ | 303.2 | 303.2 |
| $[y_3]^+$ | 416.3 | 416.3 |
| $[y_4]^+$ | 563.4 | 563.3 |
| $[y_5]^+$ | 650.4 | 650.4 |
| $[y_6]^+$ | 721.5 | 721.4 |
| $[y_8]^+$ | 877.5 | 877.5 |
| $[y_9]^+$ | 1063.6 | 1063.6 |
| $[y_{10}]^+$ | 1255.6 | 1255.6 |
| $[y_{11}]^+$ | 1383.9 | 1383.7 |
| b-series ions | | |
| $[b_3]^+$ | 452.3 | 452.2 |
| $[b_8]^+$ | 952.4 | 952.4 |
| $[b_9]^+$ | 1099.6 | 1099.5 |
| $[b_{10}]^+$ | 1212.7 | 1212.6 |

US 8,318,172 B2

BREAKING IMMUNOLOGICAL TOLERANCE WITH A GENETICALLY ENCODED UNNATURAL AMINO ACID

CROSS-REFERENCE TO RELATED APPLICATIONS

This application claims priority to and benefit of U.S. Provisional Patent Application Serial Nos.: 61/065,148, filed on Feb. 8, 2008; 61/065,515, filed on Feb. 12, 2008; 61/135,947 filed Jul. 25, 2008; 61/137,676 filed Jul. 31, 2008; 61/203,948, filed Dec. 29, 2008; 61/065,147, filed Feb. 8, 2008; 61/065,590 filed Feb. 12, 2008; 61/135,969, filed Jul. 25, 2008; 61/137,635 filed Jul. 31, 2008; and 61/203,947, filed Dec. 29, 2008; the disclosures of which are incorporated herein in their entirety for all purposes.

STATEMENT AS TO RIGHTS TO INVENTIONS MADE UNDER FEDERALLY SPONSORED RESEARCH AND DEVELOPMENT

This invention was made with United States Government support under Contract No. GM062159 by the National Institutes of Health (NIH). The United States Government has certain rights in this invention.

FIELD OF THE INVENTION

The current invention relates to the field of immunology. More specifically, the present invention provides compositions and methods for producing an immunological response in a subject against a self-antigen, e.g., TNFα, or any of a myriad of other self-antigens, or producing or increasing an immunological response in a subject against a foreign (non-self) antigen, by administering an immunogen that corresponds to a target moiety (i.e., either the self-moiety or the foreign-moiety) into which one or more unnatural amino acids have been incorporated.

BACKGROUND OF THE INVENTION

A major challenge in modern medicine concerns the treatment of medical conditions that either do not elicit production of antibodies by a subject (e.g., due to the subject's immunological tolerance to self-antigens) or which do not elicit strong/robust antibody responses (e.g., certain bacterial/viral infections). Numerous medical conditions exist which fall into such categories. For example, conditions arising from or involving a subject's own self-proteins can involve moieties such as TNFα (involved/implicated in Crohn's disease, endotoxic shock, cerebral malaria, etc.), IL 10 (involved in SLE), and the like. Furthermore, it can be difficult for a subject to produce a robust antibody response to a variety of viral and bacterial infections such as HIV, CMV, tuberculosis, and *staphylococcus*.

A number of different approaches have been put forth to address such immunological response problems. For example, some approaches have considered improved adjuvants/carriers, introduction of strong T cell epitopes into antigens, conjugation vaccines and combination vaccines. See, e.g., Baldridge, et al., *Vaccine Adjuvants: Immunological and Clinical Principles*. C. J. Hackett, Ham, D. A. Jr., Eds. (Humana Press, Totowa, N.J., 2006), pp. 235-255; Makela, et al., *Expert Rev Vaccines,* 1(3): 399-410 (2002); Dalum, et al., *Nat. Biotechnol.* 17:666 (1999); and Restifo, *Curr Opin Immunol* 8:658 (1996). Other approaches have tried immunization with nonspecifically labeled antigens (i.e., diazonium derivatized antigens). See, Weigle, *J Exp Med* 121:289 (1965).

However, there is a continuing need for better, more widely applicable methods and compositions to produce or enhance a subject's immunological response against specific self-proteins, e.g., TNFα, and/or against specific proteins from various pathogens, e.g., bacterial, viral, fungal, and/or prion pathogens. The current invention provides these and other benefits, as will be apparent upon examination.

SUMMARY OF THE INVENTION

The ability to selectively induce a strong immune response against self-proteins, or to increase the immunogenicity of specific epitopes of foreign antigens, is significant in the production of vaccines for a number of disease states, including cancer, protein folding diseases, and infectious diseases (e.g., bacterial or viral infections). The current invention utilizes the incorporation of unnatural amino acids into proteins to produce unnatural immunogens to be used in vaccinations or to produce antibodies to be used in passive immunization. In the invention, the immunogens to which the unnatural amino acids are added correspond to target moieties (e.g., disease related moieties) within the subject to be vaccinated/immunized or correspond to target moieteis (e.g., disease related moieties) that are capable of being within the subject. In embodiments where the immunogen with the unnatural amino acid is administered to a subject, the presence of the unnatural amino acid elicits an immunological response against the immunogen which is cross reactive against the target (e.g., disease related) moiety.

In a first aspect, the invention provides methods of producing or enhancing an immunological response, e.g., a B-cell mediated response and/or a T-cell mediated response, in a subject against a target moiety, e.g., a polypeptide, a carbohydrate, or a combination of both, that is in the subject or that is capable of being within the subject. The methods include providing an unnatural immunogen that comprises one or more unnatural amino acids, and administering the unnatural immunogen to the subject. The subject (e.g., a human, a monkey, a mouse, a rat, a pig, a cow, a chicken, a cage bird, an aviary bird, a reptile, and/or an amphibian) produces one or more antibodies against the unnatural immunogen, which antibodies are cross-reactive against the target moiety (thus producing or enhancing the immunogenic response against the target).

The unnatural immunogen administered to the subject to produce or enhance an immunological response corresponds to at least one target moiety within the subject (or to at least one moiety that is capable of being within the subject). In some embodiments, the target moiety can comprise a first amino acid sequence, and the unnatural immunogen can comprise a second amino acid sequence that is the same as the target's sequence, except that one or more natural amino acids of the target moiety's sequence have been substituted with one or more unnatural amino acids in the immunogen's sequence. Alternatively or additionally, the target moiety can comprise a first amino acid sequence, and the unnatural immunogen can comprise a second amino acid sequence, that is the same as the target moiety's sequence except that the immunogen's sequence further comprises one or more additional unnatural amino acids. In various embodiments, the unnatural immunogen can comprise a substantially similar structure to the target moiety from which it is derived and/or it can comprise tertiary and/or quaternary structure that is substantially similar to the target moiety from which it is derived.

The one or more unnatural amino acids present in the unnatural immunogen can optionally be antibody accessible. The one or more cross-reactive antibodies produced in the methods of this aspect can optionally be specific for an epitope on the target moiety that comprises the same sequence as the corresponding epitope on the unnatural immunogen. However, the cross-reactive antibodies can optionally be specific for an epitope on the target moiety that comprises a different sequence as compared to the corresponding epitope on the unnatural immunogen, e.g., a different sequence that optionally comprises the one or more unnatural amino acids.

In this aspect, an unnatural immunogen that is derived from a target moiety can be produced in a variety of ways. In preferred embodiments, the unnatural immunogen is produced in an orthogonal translation system. However, the unnatural immunogen can optionally be produced in an in vivo translation system (e.g., via selective pressure incorporation); in an in vitro translation system (e.g., using tRNAs that have been chemically acylated with an unnatural amino acid); by a process other than post-translational modification; or by a process other than chemical modification of one of the 20 naturally occurring canonical amino acids present in the immunogen.

The unnatural amino acids that can be incorporated into an unnatural immunogen can optionally comprise any unnatural amino acid other than one of the 20 naturally occurring canonical amino acids. The unnatural amino acid that can be incorporated can also comprise any one other than one of the 20 cannonical amino acids wherein the unnatural amino acid comprises a structure of:

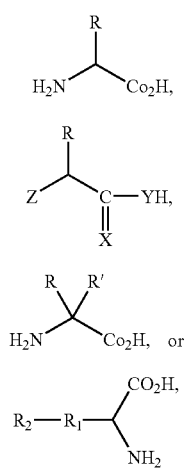

where R is any substituent other than a side chain used in any of the 20 canonical natural amino acids; wherein $R_1$ is any substituent used in one of the 20 canonical natural amino acids; wherein $R_2$ is any substituent such that R2-R1 together is other than a side chain of any of the 20 canonical natural amino acids; wherein Z is OH, $NH_2$, SH, NH—R', or S—R'; wherein R' is any substituent other than H; and wherein X and Y are each S or O and where R is of the L configuration if R' is H). In some embodiments, the one or more unnatural amino acids that can be incorporated into an immunogen can optionally include one or more: p-nitrophenylalanine; an o-nitro- phenylalanine; an m-nitrophenylalanine; a p-boronyl Phe; an o-boronyl Phe; an m-boronyl Phe; a p-amino Phe; an o-amino Phe; an m-amino Phe; a p-acyl Phe; an o-acyl Phe; an m-acyl Phe; a p-OMe Phe; an o-OMe Phe; an m-OMe Phe; a p-sulfo Phe; an o-sulfo Phe; an m-sulfo Phe; a 5-nitro His; a 3-nitro Tyr; a 2-nitro Tyr; a nitro substituted Leu; a nitro substituted His; a nitro substituted Ile; a nitro substituted Trp; a 2-nitro Trp; a 4-nitro Trp; a 5-nitro Trp; a 6-nitro Trp; a 7-nitro Trp; 3-aminotyrosine, 2-aminotyrosine, O-sulfotyrosine, 2-sulfooxyphenylalanine, 3-sulfooxyoxyphenylalanine or p-carboxyphenylalanine, o-carboxyphenylalanine, and m-carboxyphenylalanine.

In certain embodiments, the target moiety against which an immunological response is produced or enhanced can be a non-self moiety, e.g., a moiety derived from a bacterium, a virus, a fungus, a *Mycoplasma*, a protozoan, a helminth, or a prion. A non-self target moiety can optionally include one or more of: a bacterial antigen, a viral antigen, a fungal antigen, a mycoplasmal antigen, a protozoan antigen, a helminth antigen, a prion antigen, an HIV antigen, HIVgp120, HIV gp41, HIV gag, HIV pol, HIV env, HIV tat, HIV nef, HIV rev, a calicivirus capsid antigen, a hepatitis B core antigen, a hepatitis B surface antigen, hepatitis delta agent, a herpes simplex virus glycoprotein, a varicella zoster virus glycoprotein, an influenza virus hemagglutinin, an influenza virus neuraminidase, an influenza virus nucleoprotein, a HPV capsid protein, a parainfluenza virus hemagglutinin/neuraminidase, a poliovirus capsid polypeptide, a Hep A antigen, a vaccinia virus polypeptide, a rabies virus glycoprotein G, *B. burgdorferi* OspA, *H. influenzae* type b outer membrane protein, *Mycobacterium* lipoarabinomannan, mycobacterium mAPG, *S. pyogenes* M protein, *S. pneumoniae* capsular polysaccharide, *Y. pestis* F1, *Y. pestis* V antigen, *P. falciparum* circumsporozoite (PfCSP), *P. falciparum* sporozoite surface protein 2 (PfSSP2), *P. falciparum* carboxyl terminus of liver state antigen 1 (PfLSA1 c-term), *P. falciparum* exported protein 1 (PfExp-1), Pfs 48/45, Pfs 28, Pfs 25, or Pfs 230.

The target non-self moiety can optionally be derived from (or arising from) one or more of: a bacterium, a virus, a fungus, a *Mycoplasma*, a protozoan, a helminth, a prion, an *Actinomyces*, a *Bacillus*, a *Bacteroides*, a *Bordetella*, a *Bartonella*, a *Borrelia*, a *Brucella*, a *Campylobacter*, a *Capnocytophaga*, a *Chlamydia*, a *Clostridium*, a *Corynebacterium*, a *Coxiella*, a *Dermatophilus*, a *Enterococcus*, a *Ehrlichia*, a *Escherichia*, a *Francisella*, a *Fusobacterium*, a *Haemobartonella*, a *Haemophilus*, a *Helicobacter*, a *Klebsiella*, an L-form bacteria, a *Leptospira*, a *Listeria*, a *Mycobacterium*, a *Mycoplasma*, a *Neisseria*, a *Neorickettsia*, a *Nocardia*, a *Pasteurella*, a *Peptococcus*, a *Peptostreptococcus*, a *Pneumococcus*, a *Proteus*, a *Pseudomonas*, a *Rickettsia*, a *Rochalimaea*, a *Salmonella*, a *Shigella*, a *Staphylococcus*, a *Streptococcus*, a *Treponema*, a *Yersinia*, an adenovirus, an alphavirus, a calicivirus, a coronavirus, a CMV, a distemper virus, an Ebola virus, an enterovirus, an EBV, a flavivirus, a Hep C, a hepadnavirus, a Hep B, a hepititus delta agent, a Hep E or F virus, a GBV-C, a herpesvirus, a herpes simplex virus, a varicella zoster virus, an immunodeficiency virus, an HIV, an infectious peritonitis virus, an influenza virus, an influenza A virus, a leukemia virus, a Marburg virus, a orthomyxovirus, a papilloma virus, an HPV, a parainfluenza virus, a paramyxovirus, an RSV, a parvovirus, a pestivirus, a picorna virus, a poliovirus, a pox virus, a vaccinia virus, a rabies virus, a reovirus, a retrovirus, a rotavirus, an *Absidia*, an *Acremonium*, an *Alternaria*, an *Aspergillus*, a *Basidiobolus*, a *Bipolaris*, a *Blastomyces*, a *Candida*, a *Coccidioides*, a *Conidiobolus*, a *Cryptococcus*, a *Curvalaria*, an *Epidermophyton*, an *Exophiala*, a *Geotrichum*, a *Histoplasma*, a *Madurella*, a *Malassezia*, a

*Microsporum*, a *Moniliella*, a *Mortierella*, a *Mucor*, a *Paecilomyces*, a *Penicillium*, a *Phialemonium*, a *Phialophora*, a *Prototheca*, a *Pseudallescheria*, a *Pseudomicrodochium*, a *Pythium*, a *Rhinosporidium*, a *Rhizopus*, a *Scolecobasidium*, a *Sporothrix*, a *Stemphylium*, a *Trichophyton*, a *Trichosporon*, a *Xylohypha*, a *Babesia*, a *Balantidium*, a *Besnoitia*, a *Cryptosporidium*, an *Eimeria*, an *Encephalitozoon*, an *Entamoeba*, a *Giardia*, a *Hammondia*, a *Hepatozoon*, an *Isospora*, a *Leishmania*, a *Microsporidia*, a *Neospora*, a *Nosema*, a *Pentatrichomonas*, a *Plasmodium*, a *P. falciparum*, a *Pneumocystis*, a *Sarcocystis*, a *Schistosoma*, a *Theileria*, a *Toxoplasma*, a *Trypanosoma*, an *Acanthocheilonema*, an *Aelurostrongylus*, an *Ancylostoma*, an *Angiostrongylus*, an *Ascaris*, a *Brugia*, a *Bunostomum*, a *Capillaria*, a *Chabertia*, a *Cooperia*, a *Crenosoma*, a *Dictyocaulus*, a *Dioctophyme*, a *Dipetalonema*, a *Diphyllobothrium*, a *Diplydium*, a *Dirofilaria*, a *Dracunculus*, an *Enterobius*, a *Filaroides*, a *Haemonchus*, a *Lagochilascaris*, a Loa polypeptide, a *Mansonella*, a *Muellerius*, a *Nanophyetus*, a *Necator*, a *Nematodirus*, an *Oesophagostomum*, an *Onchocerca*, an *Opisthorchis*, an *Ostertagia*, a *Parafilaria*, a *Paragonimus*, a *Parascaris*, a *Physaloptera*, a *Protostrongylus*, a *Setaria*, a *Spirocerca*, a *Spirometra*, a *Stephanofilaria*, a *Strongyloides*, a *Strongylus*, a *Thelazia*, a *Toxascaris*, a *Toxocara*, a *Trichinella*, a *Trichostrongylus*, a *Trichuris*, an *Uncinaria*, or a *Wuchereria*.

In other embodiments of the invention, the target moiety against which an immunological response is produced or enhanced can optionally comprise a self-moiety of the subject. The self moiety can optionally comprise any of a variety of disease-related moieties, e.g., a self antigen related to an autoimmune disease, a tumor associated antigen, an Alzheimer's disease associated antigen, amyloid beta40, amyloid beta42, a breast cancer associated antigen, an ovarian cancer associated antigen, a prostate cancer associated antigen, MAGE, BAGE, RAGE, NY-ESO, a lineage-specific tumor associated antigen, a melanocyte-melanoma lineage antigen, MART-1/Melan-A, a tyrosinase or tyrosinase-related protein, tyrosinase-related protein 2, PSMA, PSA, mutated ras, rearranged bcr/ab1, Her2/neu, mutated or wild-type p53, cytochrome P450 1B1, an abnormally expressed intron sequence of N-acetylglucosaminyltransferase-V, CA19-9, p53, OCAA, HOXB7, Cal25, PSA, PSMA, STEAP, PCTA-1, Cal5-3, EGF, EGFR, HER-1, CXCR4, a G protein-coupled receptor (GCPR), or CA27-29.

In some embodiments the target self-moiety is TNFα and the unnatural immunogen is an unnatural TNFα. For example, in embodiments in which the subject is a mouse, the target moiety can be mTNFα, and the immunogen can be an unnatural mTNFα, e.g., an unnatural mTNFα that comprises $pNO_2Phe^{42}$-mTNFα, $pNO_2Phe^{42}$-mTNFα, $pNO_2Phe^{19}$-mTNFα, $pNO_2Phe^{21}$-mTNFα, $pNO_2Phe^{42}$-mTNFα, $pNO_2Phe^{49}$-mTNFα, $pNO_2Phe^{104}$-mTNFα, or $pNO_2Phe^{113}$-mTNFα.

Similarly, in embodiments in which the subject is a human, the target self-moiety can be an hTNFα, and the immunogen can be an unnatural hTNFα, e.g., a $pNO_2Phe^{11}$-hTNFα, a $pNO_2Phe^{19}$-hTNFα, a $pNO_2Phe^{21}$-hTNFα, a $pNO_2Phe^{42}$-hTNFα, a $pNO_2Phe^{49}$-hTNFα, a $pNO_2Phe^{87}$-hTNFα, a $pNO_2Phe^{105}$-hTNFα, and a $pNO_2Phe^{14}$-hTNFα.

In another aspect, the invention provides methods of prophylactically or therapeutically treating a disease state in a subject, e.g., by producing a B-cell mediated response and/or a T-cell mediated response in the subject. In various embodiments, the disease state can be, but is not limited to, one or more of: an autoimmune disorder, a cancer, a bacterial infection, a viral infection, a fungal infection, a *Mycoplasma* infection, a prion infection, a protozoan infection, or a helminth infection. One set of methods of the aspect includes administering an unnatural immunogen that comprises one or more unnatural amino acids to a subject, e.g., a human, a monkey, a mouse, a rat, a pig, a cow, a chicken, a cage bird, an aviary bird, a reptile, or an amphibian. The unnatural immunogen thus stimulates production of antibodies within the subject that are cross-reactive against one or more target moieties, e.g., polypeptides and/or carbohydrates, in the subject, or against one or more target moieties capable of being within the subject, that are associated with the disease state. In a second set of methods, of this aspect, the invention comprises prophyllactically or therapeutically treating a disease state in a subject by producing an antibody against one or more target moieties (e.g., a disease related moiety that is associated with the disease state/condition). Producing such an antibody comprises creating an antibody against an unnatural immunogen comprising one or more unnatural amino acids, which antibody is cross-reactive against the target moiety. The antibody is then administered to the subject.

The unnatural immunogen in the methods of this aspect typically corresponds to at least one target moiety within the subject (or to at least one target moiety that is capable of being within the subject). In various embodiments, the target moiety can comprise a first amino acid sequence, and the unnatural immunogen can comprise a second amino acid sequence that is the same as the target's sequence, except that one or more natural amino acids of the target's sequence have been substituted with one or more unnatural amino acids in the immunogen's. Alternatively or additionally, the target moiety can comprise a first amino acid sequence, and the unnatural immunogen can comprise a second amino acid sequence, where the immunogen's sequence is the same as the target's sequence except that the immunogen's sequence further comprises one or more additional unnatural amino acids. The unnatural immunogen can comprise a substantially similar structure to the target moiety from which it is derived and/or can comprise tertiary and/or quaternary structure that is substantially similar to the target moiety from which it is derived.

The one or more unnatural amino acids present in the unnatural immunogens of the methods of the aspect can optionally be antibody accessible. The one or more cross-reactive antibodies can optionally be specific for an epitope on the target moiety that comprises the same sequence as the corresponding epitope on the unnatural immunogen. However, the cross-reactive antibodies can optionally be specific for an epitope on the target moiety that comprises a different sequence as compared to the corresponding epitope on the unnatural immunogen, e.g., a different sequence that optionally comprises one or more unnatural amino acid.

In various embodiments of this aspect, the immunogen that is administered to the subject or against which an antibody is produced can be produced by any of the methods described in the earlier aspects or elsewhere herein. The unnatural immunogen can optionally include any unnatural amino acid, e.g., any of the unnatural amino acids described in the earlier aspects or elsewhere herein. The target moiety can optionally comprise a non-self moiety, e.g., including any of the non-self moieties described in the earlier aspects or elsewhere herein, or a self-moiety, e.g., a disease-related self-moiety, such as those described in the earlier aspects or elsewhere herein.

In some embodiments of this aspect, the target moiety is TNFα, and the methods of prophylatically or therapeutically treating a disease state can optionally include treating any one or more of the following disease states: endotoxic shock, cerebral malaria, an autoimmune disorder, multiple organ failure, multiple sclerosis, cardiac dysfunction, atherosclerosis, ischemia-reperfusion injury, insulin resistance, rheumatoid arthritis, Crohn's disease, inflammatory bowel disease, cachexia, septic shock, AIDS, graft-versus-host disease, bactericidal granulomas, adult respiratory distress syndrome, and silica-induced pulmonary fibrosis.

In some embodiments wherein the subject is a mouse, the target moiety can be an mTNFα, and the immunogen can be an unnatural mTNFα, e.g., an unnatural mTNFα comprising a pNO$_2$Phe$^{86}$-mTNFα: a pNO$_2$Phe$^{11}$-mTNFα, a pNO$_2$Phe$^{19}$-mTNFα, a pNO$_2$Phe$^{21}$-mTNFα, a pNO$_2$Phe$^{42}$-mTNFα, a pNO$_2$Phe$^{49}$-mTNFα, a pNO$_2$Phe$^{104}$-mTNFα, and a pNO$_2$Phe$^{113}$-mTNFα. In some embodiments wherein the subject is a human, the self-moiety can be an hTNFα, and the immunogen can be an unnatural hTNFα, e.g., a pNO$_2$Phe$^{11}$-hTNFα, a pNO$_2$Phe$^{19}$-hTNFα, a pNO$_2$Phe$^{21}$-hTNFα, a pNO$_2$Phe$^{42}$-hTNFα, a pNO$_2$Phe$^{49}$-hTNFα, a pNO$_2$Phe$^{87}$-hTNFα, a pNO$_2$Phe$^{105}$-hTNFα, and a pNO$_2$Phe$^{114}$-hTNFα.

In another aspect, the invention provides methods of producing a vaccine (as well as a vaccine produced thereby), such methods include identifying a target moiety, e.g., a polypeptide and/or carbohydrate, that does not comprise an unnatural amino acid, for antibody therapy, providing an unnatural immunogen that comprises one or more unnatural amino acids, and admixing the unnatural immunogen with one or more pharmaceutically acceptable adjuvant, carrier or excipient, thus producing the vaccine. The unnatural immunogen that is provided in these methods can be structurally similar to the target moiety such that when administered to a subject, e.g., as described in the earlier aspects or elsewhere herein, the subject will produce antibodies against the unnatural immunogen that are cross-reactive against the target moiety.

The unnatural immunogen in the methods of this aspect corresponds to at least one target moiety, within the subject (or to at least one target moiety that is capable of being within the subject). In various embodiments, the target moiety can comprise a first amino acid sequence and the unnatural immunogen can comprise a second amino acid sequence that is the same as the target's sequence, except that one or more natural amino acids of the target's sequence have been substituted with one or more unnatural amino acids in the immunogen's sequence. Alternatively or additionally, the target moiety can comprise a first amino acid sequence and the unnatural immunogen can comprise a second amino acid sequence, where the immunogen's sequence is the same as the target's sequence except that the immunogen's sequence further comprises one or more additional unnatural amino acids. The unnatural immunogen can comprise a substantially similar structure to the target moiety from which it is derived and/or can comprise tertiary and/or quaternary structure that is substantially similar to the target moiety from which it is derived.

The unnatural amino acid(s) present in the unnatural immunogen can optionally be antibody accessible. The one or more cross-reactive antibodies can optionally be specific for an epitope on the target moiety that comprises the same sequence as the corresponding epitope on the unnatural immunogen. However, the cross-reactive antibodies can optionally be specific for an epitope on the target moiety that comprises a different sequence as compared to the corresponding epitope on the unnatural immunogen, e.g., a different sequence that optionally comprises one or more unnatural amino acids.

In various embodiments, the immunogen that is provided to produce a vaccine can itself be produced by any of the methods described in the aspects above or elsewhere herein. Also the unnatural immunogen can optionally include any of the unnatural amino acids described in the aspects above or elsewhere herein. The target moiety can optionally comprise a non-self moiety, e.g., including any the non-self antigens or moieties described in the aspects above or elsewhere herein, or a self-moiety, e.g., a disease-related self-moiety, such as any of those described in the aspects above or elsewhere herein.

In some embodiments of this aspect, the target self-moiety can be TNFα. For example, in embodiments in which the subject is a mouse, the target self-moiety can be an mTNFα, and the immunogen can be an unnatural mTNFα, e.g., an unnatural mTNFα comprising a pNO$_2$Phe$^{86}$-mTNFα, a pNO$_2$Phe$^{11}$-mTNFα, a pNO$_2$Phe$^{19}$-mTNFα, a pNO$_2$Phe$^{21}$-mTNFα, a pNO$_2$Phe$^{42}$-mTNFα, a pNO$_2$Phe$^{49}$-mTNFα, a pNO$_2$Phe$^{104}$-mTNFα, and a pNO$_2$Phe$^{113}$-mTNFα. In embodiments wherein the subject is a human, the target self-moiety can be an hTNFα, and the immunogen can be an unnatural hTNFα, e.g., a pNO$_2$Phe$^{11}$-hTNFα, a pNO$_2$Phe$^{19}$-hTNFα, a pNO$_2$Phe$^{21}$-hTNFα, a pNO$_2$Phe$^{42}$-hTNFα, a pNO$_2$Phe$^{49}$-hTNFα, a pNO$_2$Phe$^{87}$-hTNFα, a pNO$_2$Phe$^{105}$-hTNFα, and a pNO$_2$Phe$^{114}$-hTNFα.

In another aspect, the invention also provides methods of producing an unnatural TNFα comprising pNO$_2$Phe$^{86}$-TNFα in a cell. The methods include growing a cell in an appropriate medium. In such embodiments, the cell can comprise a nucleic acid that encodes a TNFα and which comprises at least one selector codon at amino acid position 86. The cell can also comprise an orthogonal-tRNA (O-tRNA) that recognizes the selector codon and an orthogonal aminoacyl-tRNA synthetase (O—RS) that preferentially animoacylates the O-tRNA with the pNO$_2$Phe. The methods also include providing a pNO$_2$Phe, which permits the (O—RS) that preferentially animoacylate the O-tRNA with the pNO$_2$Phe and permits the orthogonal aminoacyl-tRNA synthetase to incorporate the pNO$_2$Phe into amino acid position 86 in response to the selector codon, thus producing the unnatural TNFα. Other embodiments herein include methods of producing any other unnatural immunogen with any desired unnatural amino acid at any desired location in the immunogen through similar methods with appropriate modification (e.g., a nucleic acid for the desired immunogen, the appropriate selector codon at the desired locations, the presence of the desired unnatural amino acids, and the appropriate corresponding orthogonal machinery ORS, OtRNA, etc.).

The invention also provides unnatural TNFαs. Unnatural mTNFαs provided by the invention include pNO$_2$Phe$^{86}$-mTNFα, a pNO$_2$Phe$^{11}$-mTNFα, a pNO$_2$Phe$^{19}$-mTNFα, a pNO$_2$Phe$^{21}$-mTNFα, a pNO$_2$Phe$^{42}$-mTNFα, a pNO$_2$Phe$^{49}$-mTNFα, a pNO$_2$Phe$^{104}$-mTNFα, and a pNO$_2$Phe$^{113}$-mTNFα. Unnatural hTNFαs provided by the invention include a pNO$_2$Phe$^{11}$-hTNFα, a pNO$_2$Phe$^{19}$-hTNFα, a pNO$_2$Phe$^{21}$-hTNFα, a pNO$_2$Phe$^{42}$-hTNFα, a pNO$_2$Phe$^{49}$-hTNFα, a pNO$_2$Phe$^{87}$-hTNFα, a pNO$_2$Phe$^{105}$-hTNFα, and a pNO$_2$Phe$^{114}$-hTNFα. Compositions comprising these unnatural TNFαs are also provided herein The invention also provides antibodies against the unnatural TNFα's described above and compositions comprising these antibodies. The invention also provides antibodies that are cross-reactive against a natural TNFα that does not comprise any unnatural amino acids and a TNFα comprising one or more unnatural amino acid as well as compositions that include these antibodies.

The invention also provides an unnatural mRBP4 comprising a pNO$_2$Phe$^{43}$ mRBP4 and compositions that include such unnatural mRBP4. In addition, the invention provides antibodies against this unnatural mRBP4 that are cross-reactive against an RBP4, which does not comprise an unnatural amino acid, and compositions that include these antibodies.

In the various aspects herein, the one or more unnatural amino acids that are incorporated into the unnatural immunogen are done so during synthesis of the immunogen. In some embodiments, the one or more unnatural amino acids are incorporated into the unnatural immunogen through a process other than post-translational modification or post-synthesis chemical modification. Thus, in various embodiments, the one or more unnatural amino acids are incorporated into the unnatural immunogen through one or more of: orthogonal translation; in vitro translation; native chemical ligation; expressed protein ligation; or solid-phase synthesis. In the various embodiments herein, the unnatural immunogen comprises one or more of the 20 naturally occurring canonical amino acids that has been glycosylated, nitroaryl modified, nitrated, alkylated, acetylated, oxidized, sulfated, or phosphorylated (e.g., glycosylated, nitroaryl modified, nitrated, alkylated, acetylated, oxidized, sulfated, or phosphorylated by a process other than post-translational modification or by a process other than chemical modification).

In some embodiments, the invention provides a kit or an article of manufacture containing materials useful for the methods and compositions described herein. Such kits can optionally comprise one or more containers, labels, and instructions, as well components for construction of antibodies and/or unnatural immunogens and/or actual antibodies and/or unnatural immunogens (e.g., unnatural TNFαs). The kits can also optionally comprise one or more antibody (e.g., an antibody against an unnatural immunogen, which antibody is cross-reactive against a natural target moiety within a subject) and/or one or more unnatural immunogen as well as optionally other components (e.g., various antibiotics, various antifungal agents, etc.). Such unnatural immunogens can include, but are not limited to, any one or more of the unnatural TNFαs provided by the invention or any other unnatural immunogen described herein. The kits can optionally include tubes or other containers (e.g., of glass, plastic, nylon, cotton, polyester, metal, etc.) to store the components or in which to mix/prepare the components as well as one or more devices with which to administer such to a subject (e.g., a human in need of treatment, etc.). In some embodiments, the device with which to administer the components to the subject comprises the container in which the components are stored and/or mixed/prepared.

The kits can also optionally include additional components in addition to the antibody/unnatural immunogen components of the invention, e.g., buffers, diluents, filters, dressings, bandages, applicators, gauze, barriers, semi-permeable barriers, tongue depressors, needles, and syringes, etc.

In some embodiments, the kits comprise instructions (e.g., typically written instructions) relating to the use of the kit to treat a subject for one or more medical condition/disease state). In some embodiments, the kits comprise a URL address or phone number or the like for users to contact for instructions or further instructions. The kits can be unit doses, bulk packages (e.g., multi-dose packages), or sub-unit doses.

It will be apparent to those of skill in the art that the methods and compositions of the invention can be used alone or in combination with one another.

These and other features of the invention will become more fully apparent when the following detailed description is read in conjunction with the accompanying figures and claims.

Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Thus, for example, reference to "a surface" includes "a combination of two or more surfaces"; reference to "bacteria" includes "mixtures of bacteria," and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

Antibody: As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin, e.g., antibody, structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

Antibodies can exist as intact immunoglobulins or as a number of well-characterized fragments produced by digestion with various peptidases. Thus, for example, pepsin digests an antibody below the disulfide linkages in the hinge region to produce F(ab')$_2$, a dimer of Fab which itself is a light chain joined to $V_H$-$C_H$1 by a disulfide bond. The F(ab')$_2$ may be reduced under mild conditions to break the disulfide linkage in the hinge region thereby converting the F(ab')$_2$dimer into an Fab' monomer. The Fab' monomer is essentially an Fab with part of the hinge region (see, *Fundamental Immunology*, W. E. Paul, ed., Raven Press, N.Y. (1999), for a more detailed description of other antibody fragments). While various antibody fragments are defined in terms of the digestion of an intact antibody, one of skill will appreciate that such Fab' fragments, etc. may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv or scFv) antibodies in which a variable heavy and a variable light chain are joined together (directly or through a peptide linker) to form a continuous polypeptide.

An antibody that "cross-reacts" with two or more different moieties is capable of binding to each of the different moieties, e.g. as determined by ELISA, FACS or other methods known to those of skill in the art. For example, an antibody that binds with an unnatural TNFα, e.g., any one of the unnatural TNFαs described herein, such as pNO$_2$Phe$^{86}$ mTNFα, and that also binds with native (or natural) TNFα

(which does not comprise any unnatural amino acids), thus cross-reacts with the two moieties. In particular embodiments herein, an antibody against an unnatural protein cross-reacts with the natural version of the same protein (i.e., the same protein, but which does not comprise an unnatural amino acid). In various embodiments, an antibody that binds to an unnatural molecule, cross-reacts to the natural version of the same molecule at about 1-50% or 50-100% or more of the binding ability of the antibody for the unnatural molecule.

Antigen: The term "antigen" is used herein to refer to a molecule or substance that induces an antibody response in a subject immunized therewith. The antigen may be a protein, peptide, carbohydrate, nucleic acid, lipid, hapten or other naturally occurring or synthetic compound (or combination thereof). The antigen can be, e.g., an innate (self) antigen, or can be derived from, e.g., a bacterium, a virus, a parasite, a fungus, etc. The term also intends any of the various tumor antigens, autoimmune disease related antigens, etc.

Cognate: The term "cognate" refers to components that function together, or have some aspect of specificity for each other, e.g., an orthogonal tRNA (O-tRNA) and an orthogonal aminoacyl-tRNA synthetase (O—RS), in which the O—RS specifically aminoacylates the O-tRNA with an unnatural amino acid.

Derived from: As used herein, the term "derived from" refers to a component that is isolated from or made using a specified molecule or organism, or sequence information from the specified molecule or organism. For example, a polypeptide that is derived from a second polypeptide can include an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of both. The mutagenesis of a polypeptide to create a different polypeptide derived from the first can be a random event, e.g., caused by polymerase infidelity, and the identification of the derived polypeptide can be made by appropriate screening methods, e.g., as discussed in references cited herein. Mutagenesis of a polypeptide typically entails manipulation of the polynucleotide that encodes the polypeptide.

Target moiety or target molecule: A "target moiety," a "target molecule," a "target protein moiety," a "target antigen" and the like refer to a moiety, e.g., a protein, peptide, carbohydrate, lipid, nucleic acid, or combination of any of such, against which it is desirable to create/enhance an immunological response through use of the current invention. Thus, a target moiety can be an innate (self) or an exogenous (foreign) molecule. It will be appreciated that recitation of specific examples herein, e.g., TNFα, should not be taken as limiting and that the target moiety (and thus an unnatural immunogen that corresponds to it) can be any molecule to which an immunological response is desired. Thus, a target moiety is one upon which the unnatural immunogen is modeled or designed, from which it is derived, to which it corresponds, etc. As explained further below, an unnatural immunogen comprises the same, or nearly the same, sequence as a target moiety except that the unnatural immunogen comprises one or more unnatural amino acids (and is created through, e.g., orthogonal translation systems, in vitro translation systems, etc. and/or through methods other than post-translational or chemical modification). In many embodiments, a target moiety is a disease related moiety, i.e., a moiety that arises or is present in a subject due to a disease state (e.g., cancer, autoimmune disorders, or from/caused by an infectious organism, such as a bacterium, virus, prion, *mycoplasm*, fungus, parasite, etc.). A natural target moiety (i.e., not comprising an unnatural amino acid) can be antigenic/and or immunogenic or not (e.g., it can be weakly immunogenic). In particular embodiments, an unnatural version of a target moiety (e.g., a moiety that is similar to the natural target moiety but which comprises one or more unnatural amino acids as replacement of corresponding natural amino acids in the target moiety and/or as additions to the amino acids of the target moiety) is antigenic and/or immunogenic (whether or not the natural target moiety is antigenic and/or immunogenic). Such unnatural target moieties are described as "unnatural target moieties," "unnatural antigens," or, more often, as "unnatural immunogens," or the like herein. Thus, an "unnatural" immunogen, moiety, molecule, etc., herein, is one that comprises one or more unnatural amino acid. In some such unnatural moieties, the unnatural amino acid is optionally either wholly or partially accessible to an antibody (e.g., an antibody can bind to the region of the moiety comprising the unnatural amino acid).

Effective amount: The term "effective amount" means a dosage or amount sufficient to produce a desired result. The desired result may comprise an objective or subjective improvement in the recipient of the dosage or amount (e.g., production of cross-reactive antibodies, long-term survival, decrease in number and/or size of tumors, effective prevention or partial prevention of a disease state, etc.).

Encode: As used herein, the term "encode" refers to any process whereby the information in a polymeric macromolecule or sequence string is used to direct the production of a second molecule or sequence string that is different from the first molecule or sequence string. The term is used broadly herein, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase. In another aspect, the term "encode" refers to any process whereby the information in one molecule is used to direct the production of a second molecule that has a different chemical nature from the first molecule. For example, a DNA molecule can encode an RNA molecule, e.g., by the process of transcription incorporating a DNA-dependent RNA polymerase enzyme. Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

Immunogen: As used herein, an "immunogen" refers to a moiety, which optionally can be administered to a subject, which induces an immunological response. An "unnatural immunogen" is a moiety, e.g., a target moiety such as a disease-related moiety, comprising one or more unnatural amino acids and which can be administered to a subject to induce an immunological response. See also above. For unnatural immunogens of the invention, serum antibodies, B-cells, and/or T-cells produced by such immunological response are advantageously cross-reactive against the corresponding natural target moiety (e.g., from which the immunogen is derived, from which it is modeled/designed, to which it corresponds, etc.) that comprises no unnatural amino acids, thus producing an immunological response against the natural target moiety. Thus, in some embodiments, an unnatural immunogen can induce an immunological response that is protective against a disease (or that can be used to treat a disease state) associated with the natural target moiety from which the unnatural immunogen is derived (or to which the unnatural immunogen corresponds, etc.).

Immunogenic composition: An "immunogenic composition" is a composition that comprises one or more molecule where administration of the composition to a subject results in the development in the subject of a humoral and/or a cellular immune response to the moiety. The immunogenic composition can be introduced directly into a recipient subject, such as by injection, inhalation, oral, intranasal and mucosal (e.g., intra-rectally or intra-vaginally) administration.

Immunological response or immune response: An "immunological response" or "immune response" to a moiety or composition thereof is the development in a subject of a cellular and/or antibody-mediated immune response to the moiety. Usually, an immunological response includes but is not limited to one or more of the following effects: the production of antibodies (preferably), B cells, helper T cells, suppressor T cells, and/or cytotoxic T cells and/or γδT cells, directed specifically to one or more antigen of the moiety. In various embodiments, the subject will display either a therapeutic or prophylactic immunological response such that resistance to a new challenge with the moiety will be enhanced and/or the clinical severity of the disease state caused by/associated with the moiety is reduced.

In response to: As used herein in regard to orthogonal production of unnatural molecules, the term "in response to" refers to the process in which an O-tRNA recognizes a selector codon and mediates the incorporation of the unnatural amino acid, which is coupled to the tRNA, into the growing polypeptide chain.

Orthogonal: As used herein, the term "orthogonal" refers to a molecule, e.g., an orthogonal tRNA (O-tRNA) and/or an orthogonal aminoacyl-tRNA synthetase (O—RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency, e.g., 45% efficiency, 50% efficiency, 60% efficiency, 70% efficiency, 75% efficiency, 80% efficiency, 90% efficiency, 95% efficiency, or 99% or more efficiency, as compared to that of a control, e.g., a corresponding tRNA/RS endogenous pair, or an active orthogonal pair.

Orthogonal aminoacyl tRNA synthetase: As used herein, an orthogonal aminoacyl tRNA synthetase (O—RS) is an enzyme that preferentially aminoacylates the O-tRNA with an amino acid in a translation system of interest. The amino acid that the O—RS loads onto the O-tRNA can be any amino acid, whether natural, unnatural or artificial, and is not limited herein. The synthetase is optionally the same as, or homologous to, a naturally occurring tyrosyl amino acid synthetase, or the same as, or homologous to, a synthetase designated as an O—RS.

Orthogonal tRNA: As used herein, an orthogonal tRNA (O-tRNA) is a tRNA that is orthogonal to a translation system of interest, where the tRNA is, e.g., (1) identical or substantially similar to a naturally occurring tRNA, (2) derived from a naturally occurring tRNA by natural or artificial mutagenesis, (3) derived by any process that takes a sequence of a wild-type or mutant tRNA sequence of (1) or (2) into account, (4) homologous to a wild-type or mutant tRNA; (5) homologous to any example tRNA that is designated as a substrate for an orthogonal tRNA synthetase or (6) a conservative variant of any example tRNA that is designated as a substrate for an orthogonal tRNA synthetase. The O-tRNA can exist charged with an amino acid, or in an uncharged state. It is also to be understood that an "O-tRNA" optionally is charged (aminoacylated) by a cognate synthetase with an unnatural amino acid. Indeed, it will be appreciated that an O-tRNA is advantageously used to insert essentially any unnatural amino acid into a growing polypeptide, during translation, in response to a selector codon.

Pharmaceutical composition: The term "pharmaceutical composition" herein refers to a composition suitable for pharmaceutical use in, or administration to, a subject, including an animal or human. A pharmaceutical composition generally comprises an effective amount of an active agent, e.g., an antibody and/or unnatural immunogen of the invention, and a pharmaceutically acceptable carrier, a buffer, adjuvant, or the like. A "pharmaceutically acceptable" or "pharmacologically acceptable" material is one that is not biologically or otherwise undesirable, i.e., the material may be administered to an individual in a formulation or composition without causing any (or causing few) undesirable biological effects or interacting in a deleterious manner with any of the components of the composition in which it is contained.

Polypeptide: A polypeptide is any oligomer of amino acid residues (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acid residues. As used herein, the amino acid sequence of a polypeptide is not limited to full-length sequences, but can be partial or complete sequences. Furthermore, it is not intended that a polypeptide be limited by possessing or not possessing any particular biological activity. As used herein, the term "protein" is synonymous with polypeptide. The term "peptide" refers to a small polypeptide, for example but not limited to, from 2-25 amino acids in length.

Preferentially aminoacylates: As used herein in reference to orthogonal translation systems, an O—RS "preferentially aminoacylates" a cognate O-tRNA when the O—RS charges the O-tRNA with an amino acid more efficiently than it charges any endogenous tRNA in an expression system. That is, when the O-tRNA and any given endogenous tRNA are present in a translation system in approximately equal molar ratios, the O—RS will charge the O-tRNA more frequently than it will charge the endogenous tRNA. Preferably, the relative ratio of O-tRNA charged by the O—RS to endogenous tRNA charged by the O—RS is high, preferably resulting in the O—RS charging the O-tRNA exclusively, or nearly exclusively, when the O-tRNA and endogenous tRNA are present in equal molar concentrations in the translation system. The relative ratio between O-tRNA and endogenous tRNA that is charged by the O—RS, when the O-tRNA and O—RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O—RS "preferentially aminoacylates an O-tRNA with an unnatural amino acid" when (a) the O—RS preferentially aminoacylates the O-tRNA compared to an endogenous tRNA, and (b) where that aminoacylation is specific for the unnatural amino acid, as compared to aminoacylation of the O-tRNA by the O—RS with any natural amino acid. That is, when the unnatural and natural amino acids are present in equal molar amounts in a translation system comprising the O—RS and O-tRNA, the O—RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O—RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Prophylactic treatment: A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such an unnatural immunogen and/or antibody, or composition thereof, that, when administered to a subject who does not display signs or symptoms of a pathology, disease, or disorder (or who displays only early signs or symptoms of such) diminishes, prevents, or decreases the risk of the subject developing the pathology, disease, or disorder. A "prophylactically useful" agent or compound (e.g., an unnatural immunogen and/or antibody of the invention, refers to an agent or compound that is useful in diminishing, preventing, treating, or decreasing development of a pathology, disease, or disorder.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Subject: The term "subject" as used herein includes, but is not limited to, a mammal, including, e.g., a human, non-human primate (e.g., monkey), mouse, pig, cow, goat, rabbit, rat, guinea pig, hamster, horse, monkey, sheep, or other non-human mammal, or a non-mammal, including, e.g., a non-mammalian vertebrate, such as a bird (e.g., a chicken or duck). In some embodiments, the methods and compositions of the invention are used to treat (both prophylactically and/or therapeutically) non-human animals. Many commercially important animals are susceptible to, e.g., various cancers or autoimmune conditions, or various infections (e.g., viral/bacterial, etc.) that can optionally be treated with the current invention.

Therapeutic treatment: A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder, e.g., typically through diminishing and/or eliminating the disease state that created the signs/symptoms. A "therapeutic activity" is an activity of an agent, such a protein and/or antibody, or composition thereof, which eliminates or diminishes signs or symptoms of a pathology, disease or disorder, when administered to a subject suffering from such signs or symptoms. A "therapeutically useful" agent or compound (e.g., an unnatural immunogen and/or antibody) indicates that an agent or compound is useful in diminishing, treating, or eliminating such signs or symptoms of the pathology, disease or disorder.

Translation system: The term "translation system" refers to the components that incorporate an amino acid into a growing polypeptide chain (protein). Components of a translation system can include, e.g., ribosomes, tRNAs, synthetases, mRNA and the like.

Treatment: As used herein, "treatment" in general refers to the prevention of infection or re-infection, the reduction or elimination of symptoms, and/or the substantial or complete elimination of a pathogen or disease state. Treatment may be effected prophylactically, e.g., prior to infection, prior to start of a disease state, or prior to development of major symptoms of a disease state, or therapeutically, e.g., following infection by a pathogen, following the start of a disease state, or following development of major symptoms of a disease state.

Unnatural amino acid: As used herein, the term "unnatural amino acid" (UAA) refers to any amino acid, modified amino acid, and/or amino acid analogue, that is not one of the 20 common naturally occurring amino acids or the rare naturally occurring amino acids e.g., selenocysteine or pyrrolysine. For example, the unnatural amino acids p-nitrophenylalanine (FIG. 1A), p-sulfotyrosine, and p-carboxyphenylalanine find use in various embodiments herein. In some embodiments, the unnatural amino acid can include, but is not limited to: p-nitrophenylalanine; an o-nitrophenylalanine; an m-nitrophenylalanine; a p-boronyl Phe; an o-boronyl Phe; an m-boronyl Phe; a p-amino Phe; an o-amino Phe; an m-amino Phe; a p-acyl Phe; an o-acyl Phe; an m-acyl Phe; a p-OMe Phe; an o-OMe Phe; an m-OMe Phe; a p-sulfo Phe; an o-sulfo Phe; an m-sulfo Phe; a 5-nitro His; a 3-nitro Tyr; a 2-nitro Tyr; a nitro substituted Leu; a nitro substituted His; a nitro substituted Ile; a nitro substituted Trp; a 2-nitro Trp; a 4-nitro Trp; a 5-nitro Trp; a 6-nitro Trp; a 7-nitro Trp; 3-aminotyrosine, 2-aminotyrosine, O-sulfotyrosine, 2-sulfooxyphenylalanine, 3-sulfooxyoxyphenylalanine or p-carboxyphenylalanine, o-carboxyphenylalanine, and m-carboxyphenylalanine. Again, it will be appreciated that the invention is not limited to particular unnatural amino acids. Additional information on unnatural amino acids is presented below.

As will be appreciated, the above terms, as well as additional terms, are detailed/described further below.

DETAILED DESCRIPTION

Overview

Figure 1:
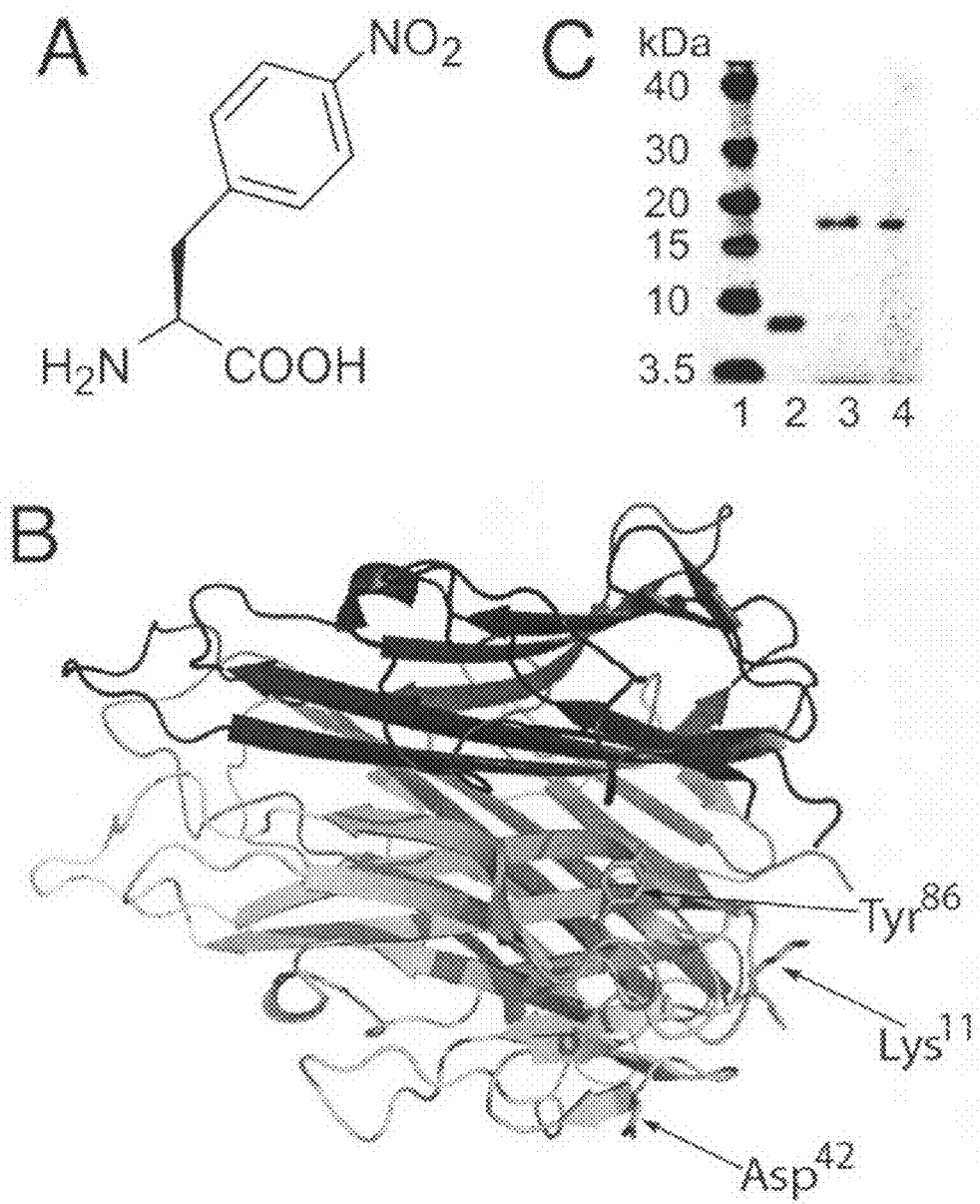
FIG. 1 depicts the chemical structure of $pNO_2Phe$, the protein structure of the mTNFα trimer, and results of experiments performed to determine the efficiency and fidelity with which $pNO_2Phe$ is incorporated into the mutant mTNFα protein.

The ability to selectively induce a strong immune response against self-proteins or other self-molecules, or to increase the immunogenicity of specific epitopes in foreign antigens, is significant in the production of vaccines for a number of disease states, including cancer, protein folding diseases, and infectious diseases (e.g., bacterial, viral, or other kinds of infections). The current invention utilizes the direct incorporation of unnatural amino acids into proteins to produce unnatural immunogens that can be beneficially used in vaccinations or to produce antibodies for passive immunization. In the invention, the proteins into which the unnatural amino acids are incorporated correspond to target moieties (e.g., disease-related moieties) within the subject to be vaccinated/immunized (or correspond to target moieties that are capable of being within the subject). In embodiments where the immunogen with the unnatural amino acid is administered to a subject, the presence of the unnatural amino acid elicits an immunological response against the unnatural immunogen. Antibodies produced by such response are beneficially cross-reactive against the natural target moiety from which the immunogen is derived (or corresponds to), thus producing an immunological response against the target moiety. The methods of the invention are particularly useful in generating an immunological response against non-immunogenic or weakly immunogenic target moieties that are in (or capable of being in) the subject. The invention also includes embodiments in which a subject is administered antibodies produced against the unnatural immunogen (i.e., the immunogen having the unnatural amino acid) that are cross-reactive against the corresponding natural target moiety (again, e.g., disease-related moiety) within (or capable of being within) the subject. In either embodiment, the invention results in increased immunological protection against challenge by the target moiety, whether such is an innate self-protein, e.g., TNFα, or a foreign molecule, e.g., a bacterial antigen.

In one example, the invention described herein also provides compositions and methods that can be useful in the treatment and/or prevention of pathologies associated with the activity of TNFα. Tumor necrosis factor alpha (TNFα) is a pleiotropic cytokine that is implicated in exacerbating and/or causing many chronic inflammatory diseases, e.g., septic shock, rheumatoid arthritis, cerebral malaria, and Crohn's disease. The invention provides methods of producing an unnatural TNFα, e.g., a TNFα comprising one or more immunogenic, antibody-accessible unnatural amino acid. The invention also provides methods for using an unnatural TNFα to break immunological tolerance for TNFα, e.g., to induce the immune system to produce or enhance an immune response against the body's endogenous TNFα. Neutralizing endogenous TNFα, e.g., with antibodies elicited against an unnatural TNFα, which antibodies cross react with epitopes on TNFα, can alleviate or ameliorate symptoms of such diseases as, e.g., endotoxic shock, cerebral malaria, autoimmune disorders, multiple organ failure, multiple sclerosis, cardiac dysfunction, atherosclerosis, ischemia-reperfusion injury, insulin resistance, rheumatoid arthritis, Crohn's disease, inflammatory bowel disease, cachexia, septic shock, AIDS, graft-versus-host disease, bactericidal granulomas, adult respiratory distress syndrome, and/or silica-induced pulmonary fibrosis.

In some embodiments comprising TNFα, the unnatural amino acid p-nitrophenylalanine, which comprises a highly immunogenic nitrophenyl moiety, replaces a tyrosine residue at position 86 of the mTNFα protein to produce an unnatural TNFα derivative with useful therapeutic and/or prophylactic properties. Additional unnatural TNFα derivatives that can find use in therapeutic and/or prophylactic treatments in a subject (e.g., a mouse) include a $pNO_2Phe^{11}$-mTNFα, a $pNO_2Phe^{11}$-mTNFα, a $pNO_2Phe^{21}$-mTNFα, a $pNO_2Phe^{42}$-mTNFα, a $pNO_2Phe^{49}$-mTNFα, a $pNO_2Phe^{104}$-mTNFα, or a $pNO_2Phe^{113}$-mTNFα. Additional unnatural TNFα derivatives that can find use in therapeutic and/or prophylactic treatments in a subject (e.g., a human) include a $pNO_2Phe^{11}$-hTNFα, a $pNO_2Phe^{19}$-hTNFα, a $pNO_2Phe^{21}$-hTNFα, a $pNO_2Phe^{42}$-hTNFα, a $pNO_2Phe^{49}$-hTNFα, a $pNO_2Phe^{87}$-hTNFα, a $pNO_2Phe^{105}$-hTNFα, or a $pNO_2Phe^{114}$-hTNFα.

In another example, the invention described herein also provides compositions and methods that can be useful in the treatment and/or prevention of pathologies associated with the activity of retinol binding protein 4 (RBP4). RBP4 has been implicated in presence/development of, e.g., Matthew Wood Syndrome, age-related macular degeneration (AMD), and Stargardt's disease, etc.

Breaking Immunological Tolerance with Unnatural Immunogens

A major challenge in modern medical treatment has been the development of robust methods to either increase the immunogenicity of specific weakly-immunogenic foreign antigens, e.g., to elicit neutralizing antibodies, or to selectively overcome tolerance to self-antigens. Important to the process of immunological discrimination between self and non-self is the concept of self-tolerance in which a mammal's immune system is "tolerized" to self-proteins in order to avoid autoimmune disease, primarily due to the absence or inactivation of self-reactive B- or T-cells. Several strategies have been pursued to address these challenges, including the development of improved adjuvants and carriers, the introduction of strong T cell epitopes into antigens, lipid conjugation, and combination vaccines, etc. See, e.g., Dalum et al., *Nat Biotechnol* 17:666 (1999); Makela, et al., *Expert Rev Vaccines* 1:399 (2002); Restifo, *Curr Opin Immunol* 8:658 (1996); and Baldridge, et al., *Vaccine Adjuvants: Immunological and Clinical Principles*. C. J. Hackett, Harn, D. A. Jr., Eds. (Humana Press, Totowa, N.J., 2006), pp. 235-255; and Zuany-Amorim, et al. (2004) "Induction of TNF-alpha autoantibody production by AutoVac TNF106: a novel therapeutic approach for the treatment of allergic diseases" *Int Arch Allergy Immunol* 133:154-163. It has been demonstrated that immunization of rabbits with a rabbit thyroglobulin that has been extensively nonspecifically labeled with a diazonium derivative induces cross-reactive antibodies to native thyroglobulin. See, Weigle, *J Exp Med* 121:289 (1965). However, such an approach is not easily modified/controlled to address other antigens, etc. Also, the nonspecific derivatization of autologous cancer cells with dinitrophenyl groups has been exploited as a vaccine in melanoma patients (Berd, D. (2004) "M-Vax: an autologous, hapten-modified vaccine for human cancer" *Expert Rev Vaccines* 3:521-527). Further references are found thoughout (e.g., the Examples below).

In contrast to prior attempts, the current invention permits the substitution (at particular desired locations) of one or more natural amino acids in a target epitope of a target moiety (e.g., a disease-related moiety) with one or more unnatural amino acids (UAA) in order to create an unnatural immunogen. Alternately or additionally, one or more specific unnatural amino acid residues can be added to a target epitope in a target moiety to create an unnatural immunogen. Such unnatural amino acid substitutions and/or additions can create one or more immunogenic, optionally structurally conservative epitopes in the unnatural immunogen that are capable of eliciting a strong immune response, e.g., a T-cell response and/or B-cell response, to the corresponding region in the wild-type (wt) natural target protein (e.g., in a subject). Also, as explained further below, cross-reactive antibodies produced in response to an unnatural immunogen can also be specific for regions of the corresponding natural target molecule which do not include an unnatural amino acid. See below. The current invention can optionally be superior to previous attempts at breaking tolerance using monoclonal antibodies or chimeric drugs, which are problematic due to the frequent injections and large quantities or protein required. As indicated herein, in some embodiments, the serum durability of antibodies produced in a subject through use of unnatural immogens of the invention can allow a low frequency of booster immunizations to be required during treatment.

B cells recognize free (soluble) antigen (e.g., an unnatural immunogen) in the blood or lymph via BCRs (B cell receptors) or membrane bound-immunoglobulins. Following the recognition of the antigen, a B cell will internalize it and display fragments of the antigen on its surface complexed with an MHC. Once activated, B cells can develop into memory B cells, which produce and secrete antibodies that can assist in such actions as neutralizing a disease-associated target moiety from which the antigen (the unnatural immunogen) was derived (corresponds to) and/or in the destruction of infectious target agents on which the epitope is antibody accessible.

T cells, e.g., $CD4^+$ T cells, specific for an antigen (e.g., the unnatural immunogen), will bind to the MHC-complexed peptide fragments displayed by, e.g., B cells. The T cells can then proliferate and release cytokines that stimulate immune cell proliferation and differentiation. Some of these primed T cells develop into memory cells which confer immediate protection against, e.g., the target (e.g., disease-related) moiety from which the unnatural immunogen was derived, as well as the capacity to mount a more rapid and effective secondary immune response. This activity can be quantified in T lymphocyte proliferation assays (see Examples 1 and 2).

Over fifty unnatural amino acids have been genetically encoded in either bacteria, yeast or mammalian cells in response to specific nonsense and frameshift codons. See, e.g., Wang, et al., *Science* 292:498 (2001); Chin, et al., *Science* 301:964 (2003); Liu, et al., *Nat Methods* 4:239 (2007); Anderson, et al., *Proc Natl Acad Sci USA* 101:7566 (2004); and Wang, et al., *Angew Chem Int Ed Engl* 44:34 (2004), as well as other references herein. These include metal-binding and posttranslationally modified amino acids, fluorescent and redox-active amino acids, and photo- and chemically-reactive amino acids. For example, the phenylalanine derivative p-nitrophenylalanine (pNO$_2$Phe, FIG. 1A) has been incorporated into proteins in bacteria in response to the amber nonsense codon with high fidelity and good efficiency for use as a spectroscopic distance probe. See Tsao, et al., *J Am Chem Soc* 128:4572 (2006). It will be appreciated that while the examples and description herein may discuss use of pNO$_2$Phe, that such should not be considered limiting and that the invention encompasses use of any unnatural amino acid (e.g., including, but not limited to, those listed herein and/or described in the references herein). Additional information on unnatural amino acids that can be used in various embodiments of the invention is given below.

Examples of Breaking Immunological Tolerance with Unnatural Immunogens.

Nitroaryl groups have historically been used as highly immunogenic haptens (see Keinan, Ed., *Catalytic Antibodies* (Wiley-VCH, Weinheim, 2005), pages 1-28), likely due to the propensity of the electron deficient pi system to interact with the Tyr and Trp side chains common to antibody combining sites. Because of their close structural similarity, either Phe→pNO$_2$Phe or Tyr→pNO$_2$Phe mutations in a target moiety (e.g., disease-related moiety) of interest can produce an immunogen that generates a robust immune response that is cross-reactive with the native natural target moiety from which the immunogen is derived (corresponds to).

Thus, as shown in the Examples, immunization of mice with, e.g., a Tyr$^{86}$→pNO$_2$Phe mutant of murine tumor necrosis factor-α: (mTNFα), generates a high titer antibody response to wild-type mTNFα (wt mTNFα), which efficiently protects mice against a lipopolysaccharide (LPS) challenge.

mTNFα was chosen as the target protein to illustrate aspects of the current invention because it is a well-characterized cytokine involved in the regulation of infectious, inflammatory and autoimmune phenomena (see Vassalli, *Annu Rev Immunol* 10:411 (1992)); and the biological properties of mTNFα, including its expression, structure, function, and signaling mechanisms have been extensively studied. See, e.g., Vassalli, supra; Baeyens, et al., *Acta Crystallogr D Biol Crystallogr* 55:772 (1999); Pennica, et al., *Proc Natl Acad Sci USA* 82:6060 (1985); Pasparakis, et al., *J Exp Med* 184:1397 (1996); Baeyens, H. L. et al., *Acta Crystallogr D Biol Crystallogr* 53:329 (1997); and Aggarwal, Vilcek, J., Ed., *Tumor necrosis factors: structure, function, and mechanism of action* (Dekker, New York, 1992), pages 1-587. In addition, mTNFα knockout mice are viable and show no apparent phenotypic abnormalities (see Pasparakis, supra), which suggests that the mice would survive a neutralizing immune response against TNF, thus allowing the vaccinated animals to be analyzed for anti-TNFα antibody production and biological activity. Furthermore, anti-TNFα antibodies (Knight, et al., *Mol Immunol* 30:1443 (1993); and Present, et al., *N Engl J Med* 340:1398 (1999)) and soluble chimeric TNFαα receptors (Peppel, et al., *J Exp Med* 174:1483 (1991); and Williams, et al., *Immunology* 84:433 (1995)) had been widely used in the treatment of rheumatoid arthritis. Thus, a TNFα-specific vaccine for clinical use would be desirable (Dalum, supra; Spohn, et al., *J Immunol* 178:7450 (2007); Buanec, et al., *Proc Natl Acad Sci USA* 103:19442 (2006); Capini, et al., *Vaccine* 22:3144 (2004)). On the basis of the X-ray crystal structure of trimeric mTNFα (Baeyens, et al., *Acta Crystallogr D Biol Crystallogr* 55:772 (1999); and Baeyens, et al., *Acta Crystallogr D Biol Crystallogr* 53:329 (1997)), a single Tyr$^{86}$→pNO$_2$Phe mutant mTNFα (pNO$_2$Phe$^{86}$ mTNFα, see FIG. 1B) was selected as an immunogen for illustration of the invention. Tyr$^{86}$ is highly conserved among different mammalian TNFs and it has been determined that mutations at this site have no effect on protein folding or on trimer formation. Mutations at Tyr$^{86}$ also lead to a significant loss in cytotoxicity, which is advantageous for vaccination purposes. See, e.g., Van Ostade, et al., *Protein Eng* 7:5 (1994); Loetscher, et al., *J Biol Chem* 268:26350 (1993); and Zhang, et al., *J Biol Chem* 267:24069 (1992).

Example 2 provides further illustration of the broad applicability of the current invention by, e.g., characterizing the nature and durability of the polyclonal IgG antibody response against TNFα and by showing the generation of an antibody response against wild-type retinol binding protein 4, mRBP4, (thus showing the use of the invention with a self-protein that is unrelated to immune function). Interestingly, Example 2 also shows that pNO$_2$Phe-induced breakdown of self-tolerance generates an antibody response against multiple epitopes in WT mTNFα, which epitopes do not necessarily include the region in the natural TNFα corresponding to the region comprising the pNO$_2$Phe residue in the unnatural immunogen TNFα. Thus, immunization with an unnatural immunogen of the invention can advantageously result in immunoglobulin epitope spreading, whereby epitopes distinct from an inducing epitope become major targets of an ongoing immune response. See below. The broadening of immunity to epitopes throughout the disease-associated moiety from which the unnatural immunogen is derived is a phenomenon that is particularly sought after in vaccine design. Enhancing the immune system's ability to attack multiple targets on a disease-associated moiety can increase the efficiency and/or robustness of an immune response against the moiety.

It will be appreciated that the illustrations in the Examples below are not the only TNFα or RPB4 embodiments of the invention. As will be apparent from the description herein, various embodiments can comprise one or more of ANY unnatural amino acid in the unnatural TNFα and RPB4 moieties. Furthermore, the unnatural amino acids present in such unnatural immunogens can optionally be in any location within the immunogens. The unnatural amino acids that replace the corresponding natural amino acids in the natural TNFα and RBP4 can be conservative amino acid replacements or can be non-conservative amino acid replacements. Also, the unnatural immunogenic TNFα and RBP4 can be constructed in any of a number of methods. While many embodiments utilize orthogonal translation (see below) as the route of direct incorporation of the unnatural amino acids, other direct incorporation methods (e.g., in vitro translation systems, solid-phase synthesis, etc.) can also optionally be used. The embodiments herein typically do not use post-translational or chemical modification methods except in conjunction or in addition to direct incorporation methods such as orthogonal translation.

Methods and Compositions to Strengthen/Enhance Immunogenic Responses

As can be seen from the Examples and description herein, unnatural immunogens of the invention can produce a robust cross-reactive antibody response against a native target moiety(s) (e.g., a disease-related protein that does not comprise an unnatural amino acid) that is protective against a disease (or that can be used to treat a disease state) associated with the target moiety(s). Thus, the invention can break immunological self-tolerance by the site-specific incorporation of an unnatural amino acid into a specific epitope of a target moiety of interest, e.g., a surface exposed epitope or a T-cell epitope in a disease related moiety). For example, in the simplified scematic below, a target moiety (e.g., a disease related moiety) comprises epitopes 1, 2, and 3. The unnatural immunogen also comprises epitopes 1, 2, and 3, which are derived from or correspond to (e.g., have identical sequences as) epitopes 1, 2, and 3 of the moiety. However, epitope 2 of the unnatural immunogen includes an unnatural amino acid (indicated by the asterisk) which replaces the corresponding natural amino acid in the target moiety. The presence of the unnatural amino acid in the unnatural immunogen can lead to the production of cross-reactive antibodies that can recognize different epitopes of the target moiety (epitope spreading). For example, cross reactive antibodies can be generated against epitopes 1 and 3 (which do not correspond to the epitope in the unnatural immunogen that comprises the unnatural amino acid) as well as to epitope 2 (which does correspond to the epitope in the unnatural immunogen having the unnatural amino acid)

| Target moiety | | |
| --- | --- | --- |
| Epitope 1 | Epitope 2 | Epitope 3 |

| Unnatural Immunogen | | |
| --- | --- | --- |
| Epitope 1 | Epitope 2 * | Epitope 3 |

Breaking immunological self-tolerance by site-specific incorporation of an unnatural amino acid into a specific epitope of a target moiety of interest to thus create an unnatural immunogen is applicable to a large number of endogenous moieties (e.g., proteins), including those associated with protein folding diseases or cancer (e.g., an amyloid-beta (1-42) peptide or prostate specific antigen, respectively). In addition, this approach also allows generation of a strong antibody response against weakly immunogenic epitopes to result in neutralizing antibodies against foreign target moieties, e.g., foreign targets arising from viral, bacterial, fungal, prion, or parasitic infections.

It will be appreciated that various embodiments herein utilize administration of an unnatural immunogen (i.e., a molecule that corresponds to a target moiety, but which comprises one or more unnatural amino acids) which, when inoculated into a subject, will lead to production of antibodies, B cells, and/or T-cells against the unnatural immunogen that are cross-reactive against the target moiety, e.g., a disease-related moiety that does not comprise unnatural amino acids and which moiety is within the subject or capable of being within the subject. In yet other embodiments, an unnatural immunogen can be used to produce antibodies that cross-react with the natural target moiety, which antibodies are in turn administered as prophylactic/therapeutic treatments to a subject.

Thus, in some embodiments herein, the invention comprises methods of producing an immunogenic (or immunological) response against a target moiety in a subject (e.g., a disease related moiety, a self-molecule of the subject, a molecule from a pathogen in the subject, or a molecule from a pathogen that is capable of being within the subject, etc.) by administering an unnatural immunogen that comprises one or more unnatural amino acid to the subject. Antibodies against the immunogen, which corresponds to a target moiety that does not comprise unnatural amino acids, are produced by the subject, which antibodies are cross-reactive against the particular target moiety. Again, it will be appreciated that the antibodies produced are not necessarily specific for the epitope on the target moiety that corresponds to the epitope that has the unnatural amino acid on the unnatural immunogen. The methods of the invention can be used to break immunological tolerance in a subject in regard to the target (e.g., disease related) moiety. Also, while described herein in terms of production via an orthogonal translation system or other direct incorporation methods (see below), the immunogenic unnatural antigens can be, once created, modified through other methods as well (e.g., chemical modification, etc.). Such indirect methods are typically used in conjunction with or in addition to direct incorporation methods such as orthogonal methods.

As explained in more detail below, the immunogen used to produce the immunological response in the subject typically comprises an "unnatural" version of a target moiety within a subject or a target moiety that is capable of being within the subject (e.g., a moiety from a bacteria that could infect the subject, a moiety from a tumor that could arise in the subject, etc.). In other words, the unnatural immunogen optionally comprises the same amino acid sequence/structure as the target moiety, except that one or more amino acid residue in the target moiety has been substituted with an unnatural amino acid (see Example sections below for additional illustration). Alternately or additionally, the unnatural immunogen can comprise the amino acid sequence of the target moiety along with one or more additional unnatural amino acid residues. In particular embodiments, the replacement and/or additional unnatural amino acid(s) does not change (or only slightly) changes the conformational structure of the unnatural immunogen as compared to the original target moiety. Thus, the tertiary and/or quaternary structure of the unnatural immunogen and the target moiety can be the same, or can be very similar to one another. Placement of the one or more unnatural amino acids in the unnatural immunogen is optionally chosen based on, e.g., whether placement in that location would change the conformation of the immunogen vs. the target moiety from which it is derived, whether the location allows the unnatural amino acid to be antibody accessible (e.g., can an antibody bind to the area comprising the unnatural amino acid), etc. The unnatural amino acid that is incorporated into the unnatural immunogen can be a conservative or non-conservative replacement (as compared to the corresponding natural amino acid in the target moiety).

Other embodiments of the invention are drawn to methods of prophylactically and/or therapeutically treating a subject by administering one or more unnatural immunogen and/or administering antibodies against one or more such unnatural immunogen that are cross-reactive with the corresponding natural target moiety.

The invention also includes embodiments comprising methods of producing a vaccine by identifying a target moiety (e.g., a disease-related moiety) that is at least putatively susceptible to treatment (e.g., TNFα). It will be appreciated that such target moiety is typically "natural" and does not comprise any unnatural amino acids. The methods also comprise providing an unnatural immunogen, i.e., a corresponding "unnatural" version of the target moiety and which comprises one or more unnatural amino acid, e.g., a replacement and/or additional unnatural amino acid. Again, the immunogen can comprise the same or nearly the same structural conformation as the target moiety such that administration of the unnatural immunogen to a subject elicits antibodies against the immunogen that are cross-reactive against the target moiety. The invention also comprises vaccines produced by such methods.

It will be appreciated that in the various embodiments herein, the natural target moiety may or may not be present in the subject when the immunological response is created and/or when prophylactic treatment is administered, etc. Thus, when a target moiety herein is described as being in or within a subject, it should be appreciated that such also includes wherein the target moiety is capable of being within the subject. Thus, the target moiety could be from a tumor that could arise in the subject, or from an infectious agent that could infect the subject, etc.

Thus, as explained throughout, in various embodiments, the target moiety can be a disease related moiety, an innate moiety, a foreign moiety, etc. The target moiety can be non-immunogenic by itself or can be partially or weakly immunogenic, etc. The target moieties that are foreign can be from any organism (e.g., bacteria, virus, etc.). The target moieties that are self can be any self antigen (e.g., tumor associated, etc.). The unnatural amino acid that is incorporated into the unnatural immunogen can be any unnatural amino acid, see below, and can be located anywhere within the immunogen. When compared to the natural amino acid in the target moiety, the replacement unnatural amino acid in the immunogen can be a conservative or a non-conservative replacement. Also, as described further below, the unnatural immunogens can be created through any of a number of direct incorporation methods (e.g., orthogonal translation, solid-phase synthesis, etc.). Typical embodiments herein do not create unnatural immunogens though indirect incorporation methods such as post-translational modification or chemical modification (but such can optionally be used in conjunction with or in addition to direct incorporation methods such as orthogonal translation or can be used after direct incorporation methods such as orthogonal translation).

Disease States and Disease-Related Target Moieties

The methods and compositions of the invention can be used to prophylactically and/or therapeutically treat a wide variety of medical conditions/disease states. For example, the invention can be used in the treatment of immune disorders. Such immune disorders can include, but are not limited to: autoimmune diseases (e.g., diabetes mellitus, arthritis, rheumatoid arthritis, juvenile rheumatoid arthritis, osteoarthritis, psoriatic arthritis, multiple sclerosis (e.g., involving MS associated antigens such as TRAIL, CD95/CD95, etc.), encephalomyelitis, myasthenia gravis, systemic lupus erythematosis (SLE), autoimmune thyroiditis, dermatitis, atopic dermatitis, eczematous dermatitis, psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Grave's disease, sarcoidosis, primary biliary cirrhosis, uveitis posterior and interstitial lung fibrosis, graft-versus-host disease, transplantation, and allergy (e.g., atopic allergy). The invention can also treat disease states of non-autoimmune/non-infectious pathogen origin such as diabetes/cardiovascular disease (e.g., involving RBP4), or of idiopathic origin such as Alzheimer's Disease (e.g., wherein the disease-related moiety can comprise, e.g., amyloid beta40, amyloid beta42, or the like).

Various embodiments of the methods and compositions of the invention also can be used to prophylactically and/or therapeutically treat disease states associated with TNFα activity, e.g., cachexia, septic shock, bactericidal granulomas, adult respiratory distress syndrome, silica-induced pulmonary fibrosis, autoimmune disorder, multiple organ failure, multiple sclerosis, cardiac dysfunction, atherosclerosis, ischemia-reperfusion injury, insulin resistance, and inflammatory bowel disease, etc. Other embodiments of the invention can be used to prophylactically and/or therapeutically treat disease states associated with RBP4 activity, e.g., Matthew Wood Syndrome, age-related macular degeneration (AMD), and Stargardt's disease, etc.

In other embodiments, the methods and compositions of the invention can be used to prophylactically and/or therapeutically treat various cancers (e.g., cancer of the breast, prostate, ovaries, lungs, skin, etc.). Such treatment can include, but is not limited to treatment of those cancers for which there are tumor-associated antigens. Tumor-associated antigens are known for numerous cancers, e.g., breast cancer, prostate cancer, ovarian cancer, etc. Tumor-associated antigens can include, but are not limited to: carcino embryonic antigen (CEA) from colon and other cancers, MAGE, BAGE, RAGE, and NY-ESO (non-mutated antigens expressed in the immune-privileged areas of the testes and in a variety of tumor cells); lineage-specific tumor antigens such as the melanocyte-melanoma lineage antigens MART-1/Melan-A, gp100, gp75, mda-7, tyrosinase and tyrosinase-related protein, or the prostate specific membrane antigen (PSMA) and prostate-specific antigen (PSA), which are antigens expressed in normal and neoplastic cells derived from the same tissue; epitope proteins/peptides derived from genes mutated in tumor cells or genes transcribed at different levels in tumor compared to normal cells, such as mutated ras, bcr/abl1 rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; epitope proteins/peptides derived from oncoviral processes, such as human papilloma virus proteins E6 and E7; and non-mutated oncofetal proteins with a tumor-selective expression, such as carcinoembryonic antigen and alpha-fetoprotein.

In particular embodiments, the invention can be used to treat ovarian cancer and/or the target disease-related moiety can comprise, e.g., an ovarian tumor-associated antigen, CA19-9, p53, OCAA, HOXB7, Cal25, etc. In yet other embodiments, the invention can be used to treat prostate cancer and/or the target disease-related moiety can comprise, e.g., a prostate tumor associated antigen, PSA, PSMA, STEAP, PCTA-1, etc. Other embodiments herein comprise treatment of breast cancer and/or the target disease-related moiety can comprise, e.g., CA15-3, CA27-29, Her2/neu, etc. Further information on tumor associated antigens that can be utilized in the current invention, can be found in, e.g., "Tumor-Antigens Recognized By T-Lymphocytes," Boon, et al., *Annual Review Of Immunology* 12:337-365, 1994; and "A listing of human tumor antigens recognized by T cells," Renkvist, et al., *Cancer Immunology Immunotherapy* 50:(1) 3-15 MAR 2001.

In other embodiments, the invention can be used to treat diseases, disorders, etc. involving self-antigens such as, but not limited to, e.g., EGF, EGFR, HER-1, CXCR4, or any of the G protein-coupled receptors (GCPR). Those of skill in the art will be familiar with numerous tumor associated antigens and corresponding cancers and self antigens and immune disorders that can be addressed through the current invention.

In some embodiments, the invention comprises treatment for HIV infection, wherein the unnatural antigen can correspond to a target disease-related moiety associated with HIV/AIDS, e.g., gp120, gp41, gp160, etc. Other exemplary HIV moieties include, but are not limited to: gag, pol, env, tat, nef, and rev.

In other embodiments, the invention can be used to treat viral infection and the unnatural immunogen can correspond to a target disease-related moiety associated with a virus, e.g., an adenovirus, an alphavirus, a calicivirus (e.g., a calicivirus capsid antigen), a coronavirus, a CMV (e.g., pp 65), a distemper virus, an Ebola virus, an enterovirus, an EBV (e.g., gp340 or nucleoantigen 3A), a flavivirus such as Hep C (e.g., core antigen), a hepadnavirus such as Hep B (e.g., a hepatitis B core or surface antigen, HbsAg, or envelope Ag pre S2, or pre S1 ag), a hepatitis delta agent, a Hep E or F virus, a Hepatitis A virus (e.g., VP1), a GBV-C, herpesvirus (e.g., a herpes simplex virus protein, e.g., type I glycoprotein G or gpD or CP27, or a varicella zoster virus glycoprotein, e.g., IE62 or gp1 or envelope protein), an immunodeficiency virus such as HIV (e.g., envelope or protease), an infectious peritonitis virus, an influenza virus (e.g., an influenza A hemagglutinin, neuraminidase, or nucleoprotein), a LCMV (e.g., nucleoprotein), a leukemia virus, a Marburg virus, an orthomyxovirus, a papilloma virus such as HIV (e.g., HPV capsid proteins), a parainfluenza virus (e.g., the hemagglutinin/neuraminidase), a paramyxovirus such as RSV (e.g., F or G proteins), a parvovirus, a pestivirus, a picorna virus (e.g., a poliovirus capsid polypeptide such as VP1, VP2, or VP3, or a Hep A antigen), a pox virus (e.g., a vaccinia virus polypeptide such as an envelope protein), a rabies virus (e.g., a rabies virus glycoprotein G), reovirus, a retrovirus, a rhinovirus (e.g., a human rhinovirus capsid), a rubella virus (e.g., a capsid protein), or a rotavirus.

In yet other embodiments, the invention can be used to treat bacterial or mycobacterial infection and the unnatural immunogen can be created to correspond to a target disease-related moiety associated with a bacterium or a *Mycobacterium*, e.g., an *Actinomyces*, a *Bacillus*, a *Bacteroides*, a *Bordetella* (e.g., *B. pertussis* surface protein), a *Bartonella*, a *Borrelia* (e.g., *B. burgdorferi* OspA), a *Brucella* (e.g., *Brucella* surface protein), a *Campylobacter*, a *Capnocytophaga*, a *Chlamydia* (e.g., *C. trachomatis* surface protein), a *Clostridium*, a *Corynebacterium*, a *Coxiella*, a *Dermatophilus*, an *Enterococcus*, an *Ehrlichia*, an *Escherichia*, a *Francisella*, a *Fusobacterium*, a *Haemobartonella*, a *Haemophilus* (e.g., *H. influenzae* type b outer membrane protein), a *Helicobacter*, a *Klebsiella*, an L-form bacteria, a *Leptospira*, a *Listeria* (e.g., a surface protein), a *Mycobacteria* such as for tuberculosis (e.g., *Mycobacteria* lipoarabinomannan, *Mycobacteria* mAPG, ESAT-6, Ag85B), a *Mycoplasma*, a *Neisseria* (e.g., *N. meningitides* class 1 outer protein), a *Neorickettsia*, a *Nocardia*, a *Pasteurella*, a *Peptococcus*, a *Peptostreptococcus*, a *Pneumococcus*, a *Proteus*, a *Pseudomonas*, a *Rickettsia*, a *Rochalimaea*, a *Salmonella*, a *Shigella*, a *Staphylococcus* (e.g., *staphylococcus* GP-1), a *Streptococcus* (e.g., *S. pyogenes* M proteins or *S. pneumoniae* capsular polysaccharides or *Streptococcus* surface protein Ag), a *Treponema*, a *Vibrio* (e.g., *Vibrio cholerae* TcpA pilin subunit), and a *Yersinia* (e.g., *Y. pestis* F1 and V antigens).

Other embodiments herein can comprise methods and compositions, etc., for treatment of fungal infection and the unnatural immunogens created can correspond to a target disease-related moiety associated with a fungus, e.g., an *Absidia*, an *Acremonium*, ab *Alternaria*, an *Aspergillus*, a *Basidiobolus*, a *Bipolaris*, a *Blastomyces*, a *Candida*, a *Coccidioides*, a *Conidiobolus*, a *Cryptococcus*, a *Curvalaria*, an *Epidermophyton*, an *Exophiala*, a *Geotrichum*, a *Histoplasma*, a *Madurella*, a *Malassezia*, a *Microsporum*, a *Moniliella*, a *Mortierella*, a *Mucor*, a *Paecilomyces*, a *Penicillium*, a *Phialemonium*, a *Phialophora*, a *Prototheca*, a *Pseudallescheria*, a *Pseudomicrodochium*, a *Pythium*, a *Rhinosporidium*, a *Rhizopus*, a *Scolecobasidium*, a *Sporothrix*, a *Stemphylium*, a *Trichophyton*, a *Trichosporon*, and a *Xylohypha*.

Some embodiments herein can comprise methods and compositions, etc., for treatment of a protozoan infection and the unnatural immunogens created can correspond to a target disease-related moiety associated with a protozoan parasite, e.g., a *Babesia*, a *Balantidium*, a *Besnoitia*, a *Cryptosporidium*, an *Eimeria*, an *Encephalitozoon*, an *Entamoeba*, a *Giardia*, a *Hammondia*, a *Hepatozoon*, an *Isospora*, a *Leishmania* (e.g., leishmania major surface glycoprotein such as gp63), a *Microsporidia*, a *Neospora*, a *Nosema*, a *Pentatrichomonas*, a *Plasmodium* (e.g., *P. falciparum* circumsporozoite (PfCSP), a sporozoite surface protein 2 (PfSSP2), a carboxyl terminus of liver state antigen 1 (PfLSA1 c-term), an exported protein 1 (PfExp-1), a Pfs 48/45, a Pfs 28, a Pfs 25, a Pfs 230), a *Pneumocystis*, a *Sarcocystis*, a *Schistosoma*, a *Theileria*, a *Toxoplasma*, and a *Trypanosoma*.

Still other embodiments herein can comprise methods and compositions for treatment of a helminth infection and the unnatural immunogens created can correspond to a target disease-related moiety associated with a helminth parasite, e.g., an *Acanthocheilonema*, an *Aelurostrongylus*, an *Ancylostoma*, an *Angiostrongylus*, an *Ascaris*, a *Brugia*, a *Bunostomum*, a *Capillaria*, a *Chabertia*, a *Cooperia*, a *Crenosoma*, a *Dictyocaulus*, a *Dioctophyme*, a *Dipetalonema*, a *Diphyllobothrium*, a *Diplydium*, a *Dirofilaria*, a *Dracunculus*, an *Enterobius*, a *Filaroides*, a *Haemonchus*, a *Lagochilascaris*, a Loa polypeptide, a *Mansonella*, a *Muellerius*, a *Nanophyetus*, a *Necator*, a *Nematodirus*, an *Oesophagostomum*, an *Onchocerca*, an *Opisthorchis*, an *Ostertagia*, a *Parafilaria*, a *Paragonimus*, a *Parascaris*, a *Physaloptera*, a *Protostrongylus*, a *Setaria*, a *Spirocerca*, a *Spirometra*, a *Stephanofilaria*, a *Strongyloides*, a *Strongylus*, a *Thelazia*, a *Toxascaris*, a *Toxocara*, a *Trichinella*, a *Trichostrongylus*, a *Trichuris*, an *Uncinaria*, and a *Wuchereria*.

Other embodiments of the invention can comprise methods and compositions for treatment of an ectoparasite infection and the unnatural immunogens created can correspond to a target disease-related moiety associated with an ectoparasite. Such ectoparasite can include, e.g., fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs. In yet other embodiments, the immunogen can correspond to a target moiety of a pollen or an allergen.

Unnatural Amino Acids

As used herein, an unnatural amino acid refers to any amino acid, modified amino acid, or amino acid analogue other than selenocysteine and/or pyrrolysine and the following twenty canonical genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. In various embodiments of the invention, the one or more unnatural amino acid that is incorporated into the unnatural immunogen can be any unnatural amino acid. Thus, it will be appreciated that recitation of specific unnatural amino acids herein should not necessarily be taken as limiting on the invention. A wide variety of unnatural amino acids have been incorporated into proteins by coding for them in vivo, e.g., using translation systems that comprise orthogonal elements. See, e.g., Liu, et al. (2007) "Genetic incorporation of unnatural amino acids into proteins in mammalian cells" *Nat Methods* 4:239-244; Wang, et al. (2006) "Expanding the genetic code" *Annu Rev Biophys Biomol Struct* 35:225-249; Xie & Schultz (2006) "A chemical toolkit for proteins—an expanded genetic code" *Nat Rev Mol Cell Biol* 7:775-782; Wang and Schultz "Expanding the Genetic Code," *Angewandte Chemie Int. Ed,* 44(1):34-66 (2005) and Chin, et al. (2003) "An expanded eukaryotic genetic code" *Science* 301:964-967 for a review.

In addition, in various embodiments of the present invention, unnatural amino acids can be incorporated into immunogens in vitro, e.g., using biosynthetic methods in which a suppressor tRNA is chemically acylated with a desired unnatural amino acid and is added to an in vitro extract capable of supporting immunogen biosynthesis. For a description of such in vitro synthetic methods, see, e.g., V. W. Cornish, D. Mendel and P. G. Schultz, *Angew. Chem. Int. Ed. Engl.,* 1995, 34:621 (1995); C. J. Noren, S. J. Anthony-Cahill, M. C. Griffith, P. G. Schultz, "A general method for site-specific incorporation of unnatural amino acids into proteins," *Science* 244 182-188 (1989); and, J. D. Bain, C. G. Glabe, T. A. Dix, A. R. Chamberlin, E. S. Diala, *"Biosynthetic site-specific incorporation of a non-natural amino acid into a polypeptide,"* J. Am. Chem. Soc. 111 8013-8014 (1989). Unnatural amino acids can also be added to naturally or synthetically produced proteins by available synthetic peptide chemistries (or natural amino acids can be converted to unnatural amino acids by such methods), or by post-translational processing. Again, however, it will be appreciated that such post-translation and chemical modifications are typically done in conjunction with, or in addition to, incorporation of one or more unnatural amino acids during synthesis of a molecule (e.g., direct incorporation such as orthogonal translation, solid-phase synthesis, etc.). Thus, post-translational addition or chemical modification of amino acids are typically done, if at all, only on molecules already having unnatural amino acids that were added during the synthesis of the molecule. Further information on non-orthogonal incorporation of unnatural amino acids into immunogens is given below.

The generic structure of an alpha-amino acid is illustrated by Formula I:

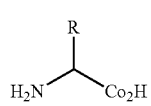

I

An unnatural amino acid is typically any structure having Formula I wherein the R group is any substituent other than one used in the twenty natural amino acids. See, e.g., *Biochemistry* by L. Stryer, 3$^{rd}$ ed. 1988, Freeman and Company, New York, for structures of the twenty natural amino acids. Note that, the unnatural amino acids of the invention, e.g., used to enhance an immunological response, can be naturally occurring compounds other than the twenty alpha-amino acids above.

Because the unnatural amino acids used herein typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

In unnatural amino acids, for example, R in Formula I optionally comprises an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In another aspect, the invention can utilize unnatural amino acids having the general structure illustrated by Formula IV below:

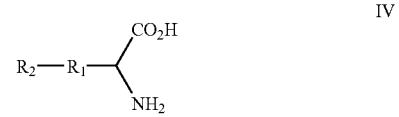

IV

An unnatural amino acid having this structure is typically any structure where $R_1$ is a substituent used in one of the twenty natural amino acids (e.g., tyrosine or phenylalanine) and $R_2$ is a substituent such that R2-R1 together is other than a side chain of any of the 20 canonical natural amino acids. Thus, this type of unnatural amino acid can be viewed as a natural amino acid derivative.

Unnatural amino acids can also optionally comprise modified backbone structures, e.g., as illustrated by the structures of Formula II and III:

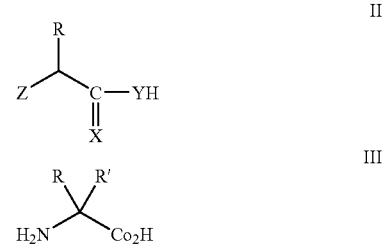

II

III wherein Z typically comprises OH, NH$_2$, SH, NH—R', or S—R'; X and Y, which can be the same or different, typically comprise S or O, and R and R', which are optionally the same or different, are typically any substituent other than H (where R is of the L configuration if R' H). For example, unnatural amino acids herein can optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

In some aspects, the invention utilizes unnatural amino acids in the L-configuration. However, it is not intended that the invention be limited to the use of L-configuration unnatural amino acids. It is contemplated that the D-enantiomers of these unnatural amino acids also find use with the invention.

Various embodiments of the invention can also include, tyrosine analogs which include para-substituted tyrosines, ortho-substituted tyrosines, and meta substituted tyrosines, wherein the substituted tyrosine comprises an alkynyl group, acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenyalanines, and meta-substituted phenylalanines, wherein the substituent comprises an alkynyl group, a hydroxy group, a methoxy group, a methyl group, an allyl group, an aldehyde, a nitro, a thiol group, or keto group, or the like. Specific examples of unnatural amino acids include, but are not limited to, p-ethylthiocarbonyl-L-phenylalanine, p-(3-oxobutanoyl)-L-phenylalanine, 1,5-dansylalanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine. Also, a p-propargyloxyphenylalanine, a 3,4-dihydroxy-L-phenyalanine (DHP), a 3, 4, 6-trihydroxy-L-phenylalanine, a 3,4,5-trihydroxy-L-phenylalanine, 4-nitrophenylalanine, a p-acetyl-L-phenylalanine, O-methyl-L-tyrosine, an L-3-(2-naphthyl)alanine, a 3-methylphenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. Other unnatural amino acids that can be included in various embodiments of the invention include, e.g., p-nitrophenylalanine; an o-nitrophenylalanine; an m-nitrophenylalanine; a p-boronyl Phe; an o-boronyl Phe; an m-boronyl Phe; a p-amino Phe; an o-amino Phe; an m-amino Phe; a p-acyl Phe; an o-acyl Phe; an m-acyl Phe; a p-OMe Phe; an o-OMe Phe; an m-OMe Phe; a p-sulfo Phe; an o-sulfo Phe; an m-sulfo Phe; a 5-nitro His; a 3-nitro Tyr; a 2-nitro Tyr; a nitro substituted Leu; a nitro substituted His; a nitro substituted Ile; a nitro substituted Trp; a 2-nitro Trp; a 4-nitro Trp; a 5-nitro Trp; a 6-nitro Trp; a 7-nitro Trp; 3-aminotyrosine, 2-aminotyrosine, O-sulfotyrosine, 2-sulfooxyphenylalanine, 3-sulfooxyoxyphenylalanine or p-carboxyphenylalanine, o-carboxyphenyalanine, and m-carboxyphenylalanine. Yet other embodiments can comprise unnatural amino acids such as an aliphatic, aryl or heterocycle substituted boronic acid, a p-boronophenylalanine, an o-boronophenylalanine, or an m-boronophenylalanine. In the various embodiments herein, the unnatural immunogen comprises one or more of the 20 naturally occurring canonical amino acids that has been glycosylated, nitroaryl modified, nitrated, alkylated, acetylated, oxidized, sulfated, or phosphorylated (e.g., glycosylated, nitroaryl modified, nitrated, alkylated, acetylated, oxidized, sulfated, or phosphorylated by a process other than post-translational modification or by a process other than chemical modification). The structures of a variety of unnatural amino acids that can be incorporated using orthogonal translation systems are known. See the references cited herein, each of which is incorporated herein by reference in its entirety.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry by March* (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids"; Matsoukas et al., (1995) *J. Med. Chem.* 38:4660-4669; King and Kidd, (1949) "A New Synthesis of Glutamine and of γ-Dipeptides of Glutamic Acid from Phthylated Intermediates," *J. Chem. Soc.,* 4:3315-3319; Friedman, and Chattenji (1959) "Synthesis of Derivatives of Glutamine as Model Substrates for Anti-Tumor Agents," *J. Am. Chem. Soc.* 81:3750-3752; Craig et al., (1988) "Absolute Configuration of the Enantiomers of 7-Chloro-4 [[4-(diethylamino)-1-methylbutyl]amino]quinoline (Chloroquine)," *J. Org. Chem.* 53:1167-1170; Azoulay, et al. (1991) "Glutamine analogues as Potential Antimalarials," *Eur. J. Med. Chem.* 26:201-5; Koskinen and Rapoport (1989) "Synthesis of 4-Substituted Prolines as Conformationally Constrained Amino Acid Analogues,".*J. Org. Chem.* 54:1859-1866; Christie and Rapoport (1985) "Synthesis of Optically Pure Pipecolates from L-Asparagine. Application to the Total Synthesis of (+)-Apovincamine through Amino Acid Decarbonylation and Iminium Ion Cyclization," *J. Org. Chem.* 1989:1859-1866; Barton, et al., (1987) "Synthesis of Novel a-Amino-Acids and Derivatives Using Radical Chemistry Synthesis of L- and D-a-Amino-Adipic Acids, L-a-aminopimelic Acid and Appropriate Unsaturated Derivatives," *Tetrahedron Lett.* 43:4297-4308; and, Subasinghe, et al., (1992) "Quisqualic acid analogues: synthesis of beta-heterocyclic 2-aminopropanoic acid derivatives and their activity at a novel quisqualate-sensitized site," *J. Med. Chem.* 35:4602-7. See also, International Publication WO 2004/058946, entitled "PROTEIN ARRAYS," filed on Dec. 22, 2003.

Cellular Uptake of Unnatural Amino Acids

Unnatural amino acid uptake by a cell is one issue that is typically considered when designing and selecting unnatural amino acids, e.g., for incorporation into an immunogen via genetically coding orthogonal pairs (an ORS that charges an OtRNA that recognizes a selector codon). For example, the high charge density of α-amino acids may limit uptake. Natural amino acids are taken up into the cell via a collection of protein-based transport systems often displaying varying degrees of amino acid specificity. A rapid screen can be done which assesses which unnatural amino acids are taken up by cells. See, e.g., the toxicity assays in, e.g., International Publication WO 2004/058946, entitled "PROTEIN ARRAYS," filed on Dec. 22, 2003; and Liu and Schultz (1999) "Progress toward the evolution of an organism with an expanded genetic code," *PNAS* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, various embodiments of the invention provide such methods. For example, biosynthetic pathways for unnatural amino acids are optionally generated in a host cell by adding new enzymes or modifying existing host cell pathways. Additional new enzymes are optionally naturally occurring enzymes or artificially evolved enzymes. For example, the biosynthesis of p-aminophenylalanine (as presented in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes optionally added can be found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994) "Rapid evolution of a protein in vitro by DNA shuffling," *Nature* 370(4):389-391; and Stemmer (1994)"DNA shuffling by random fragmentation and reassembly: In vitro recombination for molecular evolution," *Proc. Natl. Acad. Sci. USA.,* 91:10747-10751. A related approach shuffles families of related (e.g., homologous) genes to quickly evolve enzymes with desired characteristics. An example of such "family gene shuffling" methods is found in Crameri, et al., (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier, et al., (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See also, Ostermeier, et al. (1999) "Combinatorial Protein Engineering by Incremental Truncation," *Proc. Natl. Acad. Sci. USA,* 96: 3562-67, and Ostermeier, et al. (1999), "Incremental Truncation as a Strategy in the Engineering of Novel Biocatalysts," *Biological and Medicinal Chemistry,* 7: 2139-44. Another approach optionally used herein uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave and Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of, e.g., Arkin and Youvan (1992) "Optimizing nucleotide mixtures to encode specific subsets of amino acids for semi-random mutagenesis" *Biotechnology* 10:297-300; or Reidhaar-Olson, et al. (1991) "Random mutagenesis of protein sequences using oligonucleotide cassettes," *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "NON-STOCHASTIC GENERATION OF GENETIC VACCINES AND ENZYMES" WO 00/46344.

An alternative to such mutational methods involves recombining entire genomes of organisms and selecting resulting progeny for particular pathway functions (often referred to as "whole genome shuffling"). This approach can be applied to various embodiments of the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik, et al. (2002) "Genome shuffling of *lactobacillus* for improved acid tolerance" *Nature Biotechnology,* 20(7):707-712; and Zhang, et al. (2002) "Genome shuffling leads to rapid phenotypic improvement in bacteria" *Nature,* February 7, 415(6872):644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry, et al. (2002) "Application of Metabolic Engineering to improve both the production and use of Biotech Indigo" *J. Industrial Microbiology and Biotechnology* 28:127-133; Banta, et al. (2002) "Optimizing an artificial metabolic pathway: Engineering the cofactor specificity of *Corynebacterium* 2,5-diketo-D-gluconic acid reductase for use in vitamin C biosynthesis" *Biochemistry,* 41(20):6226-36; Selivonova, et al. (2001) "Rapid Evolution of Novel Traits in Microorganisms" *Applied and Environmental Microbiology,* 67:3645, and many others.

Regardless of the method used, typically, the unnatural amino acid produced with an engineered biosynthetic pathway is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Unnatural Immunogens

The unnatural immunogen used herein to produce the immunological response in the subject typically comprises an "unnatural" version of a target (e.g., disease-related) moiety within a subject or a target moiety that is capable of being within the subject (e.g., a moiety from a bacteria that could infect the subject, a moiety from a tumor that could arise in the subject, etc.). In other words, the unnatural immunogen optionally comprises the same amino acid sequence/structure as the target moiety, except that one or more amino acid residues in the target moiety have been substituted with an unnatural amino acid (see Examples section below for illustration). Alternately or additionally, the unnatural immunogen can comprise the same amino acid sequence as the target moiety but along with one or more additional unnatural amino acid residues. The unnatural immunogens of the invention can comprise, e.g., 10 or more unnatural amino acids, 5-10 unnatural amino acids, 5 or fewer unnatural amino acids, or 2 or fewer unnatural amino acids, etc. An unnatural immunogen can comprise, e.g., 10% or more, 5-10%, 5% or less, 2% or less, or 1% or less percentage of unnatural amino acids as compared to total amino acids. Again, as will be appreciated, the unnatural immunogens herein can comprise one or more of a number of different unnatural amino acids.

Location of the one or more unnatural amino acids in an unnatural immunogen of the invention should also not necessarily be taken as limiting. Thus, for example, an unnatural amino acid can be present at either the C or N terminus of an immunogen, or the unnatural amino acid can be present anywhere internally in the primary amino acid sequence of the immunogen. See, Examples section below. Placement of the unnatural amino acid(s) (and also choice of the particular unnatural amino acid) can optionally be guided by a number of considerations. For example, the location/choice of the unnatural amino acid can optionally not significantly alter the structural conformation of the immunogen vs. the natural target protein moiety from which it is derived (to which it corresponds). Thus, the structural conformation of the resulting unnatural immunogen can optionally still closely match that of the corresponding natural target moiety, such that antibody cross-reactivity occurs. Therefore, in some embodiments herein, the particular unnatural amino acid and its particular location within an immunogen can be chosen to minimize structural (e.g., tertiary/quaternary) changes to the immunogen as compared to the natural target moiety. In some embodiments, the choice of unnatural amino acid and the choice of its placement can also be influenced by whether such choice/placement will help in decreasing infectivity, cytotoxicity, etc. The unnatural amino acid(s) incorporated into the immunogen can optionally be structurally distinct from the natural amino acid(s) they replace. Thus, in some embodiments, the particular unnatural amino acid is a non-conservative alternative to the natural amino acid in the target moiety. See Examples below where a Lys residue in a target moiety was replaced with a $pNO_2Phe$ in the unnatural immunogen. In the other embodiments, the unnatural amino acid is a conservative alternative to the natural amino acid. Also, the location of the unnatural amino acid in the immunogen can be influenced by antibody accessibility and/or its ability to generate a serum antibody, B-cell, and/or T-cell response. Thus, in the various unnatural immunogens of the invention, the unnatural amino acid can be antibody accessible, e.g., surface exposed.

In various embodiments, the unnatural amino acid can be any unnatural amino acid. Further to the above, unnatural amino acids that can be used in the invention have side chain groups that distinguish them from the natural amino acids, although unnatural amino acids can be naturally occurring compounds other than the twenty proteinogenic alpha-amino acids. The unnatural amino acids finding use with the invention can include an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcb-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl; aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an a,a disubstituted amino acid; a b-amino acid; and a cyclic amino acid other than proline.

In various embodiments, the unnatural immunogens herein, e.g., unnatural TNFαs, can comprise one or more of: p-nitrophenylalanine; an o-nitrophenylalanine; an m-nitrophenylalanine; a p-boronyl Phe; an o-boronyl Phe; an m-boronyl Phe; a p-amino Phe; an o-amino Phe; an m-amino Phe; a p-acyl Phe; an o-acyl Phe; an m-acyl Phe; a p-OMe Phe; an o-OMe Phe; an m-OMe Phe; a p-sulfo Phe; an o-sulfo Phe; an m-sulfo Phe; a 5-nitro His; a 3-nitro Tyr; a 2-nitro Tyr; a nitro substituted Leu; a nitro substituted His; a nitro substituted Ile; a nitro substituted Trp; a 2-nitro Trp; a 4-nitro Trp; a 5-nitro Trp; a 6-nitro Trp; a 7-nitro Trp; 3-aminotyrosine, 2-aminotyrosine, O-sulfotyrosine, 2-sulfooxyphenylalanine, 3-sulfooxyoxyphenylalanine or p-carboxyphenylalanine, o-carboxyphenylanine, and m-carboxyphenylalanine. Again, it will be appreciated that recitation of particular unnatural amino acids should not be taken as limiting on the invention, and that other unnatural amino acids, e.g., as noted herein, can also be used with the invention.

Those of skill in the art will be readily familiar with determination of protein shape/conformation and determination of the effect, if any, of incorporation of an unnatural amino acid into a particular polypeptide, e.g., through use of protein crystallography, NMR, etc. Examples of production of an unnatural immunogen and determination of structural conformation and antibody accessibility of such an immunogen are shown in the Examples below. Such determination can optionally aid in choice and/or placement of particular unnatural amino acids in an unnatural immunogen.

The unnatural immunogens of the invention can be based on numerous target moieties and can include not only polypeptides/proteins, but also polypeptides/proteins associated with carbohydrates, lipids, haptens and/or other non-proteinaceous molecules. An immunogen of the invention can include, but is not limited to, any of the target (e.g., disease-related) moieties described herein.

In one class of useful embodiments described herein, the unnatural immunogen comprises unnatural TNFα and can comprise a highly immunogenic (E. Keinan, Ed. *Catalytic Antibodies* (Wiley-VCH, Weinheim, 2005) pp. 1-28), structurally conservative, antibody accessible p-nitrophenylalanine (pNO$_2$Phe, FIG. 1A), e.g., pNO$_2$Phe$^{86}$TNFα, pNO$_2$Phe$^{11}$-mTNFα, pNO$_2$Phe$^{19}$-mTNFα, pNO$_2$Phe$^{21}$-mTNFα, pNO$_2$Phe$^{42}$-mTNFα, pNO$_2$Phe$^{49}$-mTNFα, pNO$_2$Phe$^{19}$-mTNFα, or pNO$_2$Phe$^{13}$-mTNFα. In such embodiments, the substitution mutation permits the unnatural mTNFα to maintain a tertiary and quaternary protein structure that is substantially similar to that of the natural mTNFα, thus increasing the probability that neutralizing antibodies produced against the unnatural mTNFα can cross react with corresponding epitopes on the wt mTNFα. As detailed elsewhere herein, the replacement of and/or addition of an unnatural amino acid optionally does not change (or does not significantly change) the conformational structure of the unnatural mTNFα as compared to the endogenous mTNFα. Unnatural hTNFα that can find use in therapeutic and/or prophylactic treatments in a human subject include a pNO$_2$Phe$^{11}$-hTNFα, a pNO$_2$Phe$^{19}$-hTNFα, a pNO$_2$Phe$^{21}$-hTNFα, a pNO$_2$Phe$^{42}$-hTNFα, a pNO$_2$Phe$^{49}$-hTNFα, a pNO$_2$Phe$^{87}$-hTNFα, a pNO$_2$Phe$^{105}$-hTNFα, or a pNO$_2$Phe$^{14}$-hTNFα.

In general, elevated serum levels of TNFα are associated with a variety of disease states. It will be appreciated, however, that a subject in whom the immunological response is created and/or to whom the prophylactic treatment is administered, etc. may not exhibit at serum TNFα levels that represent a disease state. Thus, it should be appreciated that the antibodies, and/or the unnatural immunogens of the invention can be administered both to individuals who do exhibit a TNFα-associated disease as well as those who do not.

In other embodiments of the invention, the unnatural immunogen can comprise an unnatural RBP4, e.g., to treat and/or prevent RBP4-associated disease states. Any natural RBP4 can be substituted with one or more unnatural amino acid to produce an unnatural RBP4. As will be appreciated, and as for TNFα or any other target moiety, the substitution need not (but can) replace the natural amino acid with a structurally conservative unnatural amino acid. Alternatively or additionally, one or more additional unnatural amino acids can be added to an RBP4 polypeptide (rather than "replace" natural amino acids within it) to produce an unnatural RBP4. As described above for unnatural TNFα immunogens, and again, as for any other immunogen construction herein, an unnatural RBP4 can optionally comprise a structure that is substantially similar to the natural RBP4, thus increasing the probability that neutralizing antibodies produced against the unnatural RBP4 can cross react with corresponding epitopes on the natural RBP4 (whether or not such epitopes in the target RBP4 correspond to the epitope(s) in the unnatural RBP4 that have an unnatural amino acid). Of course, here too, any unnatural amino acid in an unnatural immunogen that is used to replace a natural amino acid in a target moiety does not need to be a conservative substitution. See Examples below. Unnatural RBP4s that can find use in therapeutic and/or prophylactic treatments in a subject include a pNO$_2$Phe$^{43}$ mRBP4 and a pNO$_2$Phe$^{108}$ mRBP4 as well as their corresponding human counterparts.

Production of Unnatural Immunogens

As will be appreciated, the unnatural immunogens of the invention can be constructed through a variety of methods, typically direct incorporation methods. Thus, while the description and examples herein primarily focus on use of orthogonal translation systems to incorporate unnatural amino acids into proteins, other methods can also optionally be used to create the unnatural immunogens to be administered to a subject, e.g., to produce an immunological response against the target moiety to which the immunogen corresponds, or to produce the unnatural immunogens used in the creation of cross-reactive antibodies that are to be administered to a subject to, e.g., neutralize a target moiety. In many embodiments, the unnatural amino acid is added to the unnatural immunogen during construction of the immunogen (e.g., during the construction of the immunogen through orthogonal translation, in vitro synthesis or chemo-synthetic methods, etc.) rather than through post-translational modification or chemical modification of a natural amino acid in the molecule after it has been synthesized (although such methods can optionally be used in combination with or in addition to direct incorporation approaches). Therefore, while particular methods of constructing molecules that comprise unnatural amino acids are detailed herein, e.g., orthogonal translation, they such should not necessarily be taken as limiting. Other methods of constructing molecules having unnatural amino acids that include non-post-translational and non-chemical modification are also included herein in the many embodiments.

It will be appreciated that genetic incorporation of unnatural amino acids into immunogens (e.g., through orthogonal translation systems such as those described and referenced to herein) can, in some embodiments, offer benefits over generation of unnatural immunogens through solid-phase peptide synthesis or other similar in vitro methods. For example, the genetic incorporation of unnatural amino acids into immunogens in vivo uses the biosynthetic machinery of living cells to synthesize the unnatural immunogen. Such in vivo production can produce an accurate functional immunogen (or any other moiety) similar to the native (natural) target moiety, but with the added active/functional groups introduced via the unnatural amino acids. This, thus, helps generate a robust immune response that is cross-reactive with a native (natural) target moiety or wild-type moiety. Furthermore, use of the novel biotechnological tool of in vivo incorporation of unnatural amino acids, can help produce the proper native conformation of immunogens (i.e., similar or identical to that of the corresponding target moiety) with high yields at low cost. Total synthesis of proteins with unnatural amino acids using other in vitro methods such as solid-phase peptide synthesis can in some embodiments be more targeted to shorter molecules (e.g., ~60-100 amino acids) as well as producing denatured proteins at a lower yield which can optionally be ligated together, etc.

Orthogonal tRNA/Aminoacyl-tRNA Synthetase Technology

As explained herein, unnatural immunogens used in the invention to produce an immunological response against a natural target moiety (either innate or foreign to a subject) are typically constructed through orthogonal tRNA/aminoacyl-tRNA synthetase systems. Thus, an understanding of the novel compositions and methods of the present invention is further developed through an understanding of the activities associated with orthogonal tRNA and orthogonal aminoacyl-tRNA synthetase pairs. In general, in order to add unnatural amino acids to the genetic code, new orthogonal pairs comprising an aminoacyl-tRNA synthetase and a suitable tRNA are needed that can function efficiently in the host translational machinery, but that are "orthogonal" to the translation system at issue. Thus, the orthogonal moieties function independently of the synthetases and tRNAs endogenous to the translation system. Desired characteristics of the orthogonal pair include tRNA that decode or recognize only a specific codon, such as a selector codon, e.g., an amber stop codon, that is not decoded by any endogenous tRNA, and aminoacyl-tRNA synthetase that preferentially aminoacylates, or "charges" its cognate tRNA with only one specific unnatural amino acid. The O-tRNA is also not typically aminoacylated, or is poorly aminoacylated, i.e., charged, by endogenous synthetases. For example, in an *E. coli* host system, an orthogonal pair will include an aminoacyl-tRNA synthetase that does not cross-react with any of the endogenous tRNA, of which there are 40 endogenous in *E. coli*, and an orthogonal tRNA that is not aminoacylated by any of the endogenous synthetases, of which there are 21 in *E. coli*.

The general principles of orthogonal translation systems that are suitable for making proteins that comprise one or more unnatural amino acid in the invention are known in the art, as are the general methods for producing orthogonal translation systems. For example, see International Publication Numbers: WO 2002/086075, entitled "METHODS AND COMPOSITION FOR THE PRODUCTION OF ORTHOGONAL tRNA-AMINOACYL-tRNA SYNTHETASE PAIRS"; WO 2002/085923, entitled "IN VIVO INCORPORATION OF UNNATURAL AMINO ACIDS"; WO 2004/094593, entitled "EXPANDING THE EUKARYOTIC GENETIC CODE"; WO 2005/019415, filed Jul. 7, 2004; WO 2005/007870, filed Jul. 7, 2004; WO 2005/007624, filed Jul. 7, 2004; WO 2006/110182, filed Oct. 27, 2005, entitled "ORTHOGONAL TRANSLATION COMPONENTS FOR THE VIVO INCORPORATION OF UNNATURAL AMINO ACIDS"; and WO 2007/103490, filed Mar. 7, 2007, entitled "SYSTEMS FOR THE EXPRESSION OF ORTHOGONAL TRANSLATION COMPONENTS IN EUBACTERIAL HOST CELLS." See also, e.g., Liu, et al. (2007) "Genetic incorporation of unnatural amino acids into proteins in mammalian cells" *Nat Methods* 4:239-244; Int'l Application PCT/US2008/081868 entitled "A Genetically Encoded Boronate Amino Acid," filed Oct. 30, 2008; WO2007/047301 entitled "Selective Posttranslational Modification of Phage-Displayed Polypeptides," filed Oct. 11, 2006; and WO2006/110182 entitled "Orthogonal Translation Components for the In vivo Incorporation of Unnatural Amino Acids," filed Oct. 27, 2005. Each of such applications is incorporated herein by reference in its entirety. For discussion of orthogonal translation systems that incorporate unnatural amino acids, and methods for their production and use, see also, Wang and Schultz, (2005) "Expanding the Genetic Code" *Angewandte Chemie Int Ed* 44:34-66; Xie and Schultz, (2005) "An Expanding Genetic Code" *Methods* 36:227-238; xie and Schultz, (2005) "Adding Amino Acids to the Genetic Repertoire" *Curr Opinion in Chemical Biology* 9:548-554; Wang, et al., (2006) "Expanding the Genetic Code" *Annu Rev Biophys Biomol Struct* 35:225-249; Deiters, et al., (2005) "In vivo incorporation of an alkyne into proteins in *Escherichia coli*" *Bioorganic & Medicinal Chemistry Letters* 15:1521-1524; Chin, et al., (2002) "Addition of p-Azido-L-phenylalanine to the Genetic Code of *Escherichia coli*" *J Am Chem Soc* 124:9026-9027; and International Publication No. WO2006/034332, filed on Sep. 20, 2005. The contents of each of such documents is incorporated by reference in its entirety. Additional details of orthogonal translation systems can be found in U.S. Pat. Nos. 7,045,337; 7,083,970; 7,238, 510; 7,129,333; 7,262,040; 7,183,082; 7,199,222; and 7,217, 809

Further to above, as used herein, an unnatural amino acid (however constructed) refers to any amino acid, modified amino acid, or amino acid analogue that is other than selenocysteine and/or pyrrolysine and the twenty genetically encoded alpha-amino acids. See, e.g., *Biochemistry* by L. Stryer, 3rd ed. 1988, Freeman and Company, New York, for structures of the twenty natural amino acids. In various embodiments, the unnatural amino acid is any immunogenic amino acid (e.g., an immunogenic analogue of a common amino acid). Unnatural amino acids of the invention have side chain groups that distinguish them from the natural amino acids, although unnatural amino acids can be naturally occurring compounds other than the twenty proteinogenic alpha-amino acids. Non-limiting examples of unnatural amino acids that can be used in the immogens of the invention include an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcb-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an a,a disubstituted amino acid; a b-amino acid; and a cyclic amino acid other than proline.

In particular embodiments, the unnatural immunogens herein, such as unnatural TNFαs or any other unnatural immunogen, can comprise one or more of: p-nitrophenylalanine; an o-nitrophenylalanine; an m-nitrophenylalanine; a p-boronyl Phe; an o-boronyl Phe; an m-boronyl Phe; a p-amino Phe; an o-amino Phe; an m-amino Phe; a p-acyl Phe; an o-acyl Phe; an m-acyl Phe; a p-OMe Phe; an o-OMe Phe; an m-OMe Phe; a p-sulfo Phe; an o-sulfo Phe; an m-sulfo Phe; a 5-nitro His; a 3-nitro Tyr; a 2-nitro Tyr; a nitro substituted Leu; a nitro substituted His; a nitro substituted Ile; a nitro substituted Trp; a 2-nitro Trp; a 4-nitro Trp; a 5-nitro Trp; a 6-nitro Trp; a 7-nitro Trp; 3-aminotyrosine, 2-aminotyrosine, O-sulfotyrosine, 2-sulfooxyphenylalanine, 3-sulfooxyoxyphenylalanine or p-carboxyphenylalanine, o-carboxyphenyalanine, and m-carboxyphenylalanine. Again, it will be appreciated that recitation of particular unnatural amino acids should not be taken as limiting on the invention, and that other unnatural amino acids (e.g., other immunogenic unnatural amino acids) can also be used with the invention.

Orthogonal Translation Systems

Orthogonal translation systems generally comprise cells, e.g., prokaryotic cells such as *E. coli*, that include an orthogonal tRNA (O-tRNA), an orthogonal aminoacyl tRNA synthetase (O—RS), and an unnatural amino acid, e.g., para-nitrophenylalanine (pNO$_2$Phe), para-carboxyphenylalanine, sulfotyrosine, etc. (see above), where the O—RS aminoacylates the O-tRNA with the unnatural amino acid. An orthogonal pair can include an O-tRNA, e.g., a suppressor tRNA, a frameshift tRNA, or the like, and a cognate O—RS. Orthogonal systems, that can be used to produce the unnatural proteins herein, which typically include O-tRNA/O—RS pairs, can comprise a cell or a cell-free environment.

In general, when an orthogonal pair recognizes a selector codon and loads an amino acid in response to the selector codon, the orthogonal pair is said to "suppress" the selector codon. That is, a selector codon that is not recognized by the translation system's, e.g., the *E. coli* cell's, endogenous machinery is not ordinarily charged, which results in blocking production of a polypeptide that would otherwise be translated from the nucleic acid. In an orthogonal pair system, the O—RS aminoacylates the O-tRNA with a specific unnatural amino acid, e.g., para-nitrophenylalanine (pNO$_2$Phe) as used in the Examples herein. The charged O-tRNA recognizes the selector codon and suppresses the translational block caused by the selector codon.

The translation system, e.g., an *E. coli* cell, uses the O-tRNA/O—RS pair to incorporate an unnatural amino acid into a growing polypeptide chain, e.g., via a polynucleotide that encodes a polypeptide of interest (such as an unnatural immunogen that corresponds to a target moiety that is in or capable of being in a subject, etc.), where the polynucleotide comprises a selector codon that is recognized by the O-tRNA. In certain systems, the cell can include one or more additional O-tRNA/O—RS pairs, where an additional O-tRNA is loaded by an additional O—RS with a different unnatural amino acid. For example, one of the O-tRNAs can recognize a four base codon and the other O-tRNA can recognize a stop codon. Alternately, multiple different stop codons, multiple different four base codons, multiple different rare codons and/or multiple different non-coding codons can be used in the same coding nucleic acid. Thus, a single polypeptide, e.g., unnatural immunogen, can comprise multiple unnatural amino acids and/or different polypeptides created in the system can comprise different unnatural amino acids. For further details regarding available O—RS/O-tRNA cognate pairs and their use, see, e.g., the references noted elsewhere herein.

Thus, some translational systems can comprise multiple O-tRNA/O—RS pairs, which allow incorporation of more than one unnatural amino acid into a polypeptide. For example, the translation system can further include an additional different O-tRNA/O—RS pair and a second unnatural amino acid, where this additional O-tRNA recognizes a second selector codon and this additional O—RS preferentially aminoacylates the O-tRNA with the second unnatural amino acid. For example, a cell that includes an O-tRNA/O—RS pair, where the O-tRNA recognizes, e.g., an amber selector codon, can further comprise a second orthogonal pair, where the second O-tRNA recognizes a different selector codon, e.g., an opal codon, an ochre codon, a four-base codon, a rare codon, a non-coding codon, or the like. In some systems, the different orthogonal pairs are derived from different sources, which can facilitate recognition of different selector codons.

Certain translation systems can comprise a cell, such as an *E. coli* cell, that includes an orthogonal tRNA (O-tRNA), an orthogonal aminoacyl-tRNA synthetase (O—RS), an unnatural amino acid, and a nucleic acid that comprises a polynucleotide that encodes a polypeptide of interest, e.g., an unnatural immunogen corresponding to a self-protein target of a subject, where the polynucleotide comprises the selector codon that is recognized by the O-tRNA. Although orthogonal translation systems can utilize cultured cells to produce proteins having unnatural amino acids, it is not intended that orthogonal translation systems used herein require an intact, viable cell. For example, an orthogonal translation system can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is well within the scope of the invention.

The O-tRNA and/or the O—RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a tRNA/synthetase pair that is heterologous to the system in which the pair will function from a source, or multiple sources, other than the translation system in which the tRNA/synthetase pair will be used. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases. A second strategy for generating an orthogonal pair involves generating mutant libraries from which to screen and/or select an O-tRNA or O—RS. Such strategies can also be combined.

Orthogonal tRNA (O-tRNA)

An orthogonal tRNA (O-tRNA) desirably mediates incorporation of an unnatural amino acid into a polypeptide encoded by a polynucleotide that comprises a selector codon recognized by the O-tRNA, e.g., in vivo or in vitro.

Thus compositions comprising an O-tRNA can further include an orthogonal aminoacyl-tRNA synthetase (O—RS), where the O—RS preferentially aminoacylates the O-tRNA with an unnatural amino acid. Such compositions including an O-tRNA can further include a translation system, e.g., in vitro or in vivo. A nucleic acid that comprises a polynucleotide that encodes a polypeptide of interest, where the polynucleotide comprises a selector codon that is recognized by the O-tRNA, or a combination of one or more of these can also be present in the cell.

Methods for producing a recombinant orthogonal tRNA and screening its efficiency with respect to incorporating an unnatural amino acid into a polypeptide in response to a selector codon can be found in, e.g., International Application Publications WO 2002/086075, entitled "METHODS AND COMPOSITIONS FOR THE PRODUCTION OF ORTHOGONAL tRNA AMINOACYL-tRNA SYNTHETASE PAIRS"; WO 2004/094593, entitled "EXPANDING THE EUKARYOTIC GENETIC CODE"; and WO 2005/019415, filed Jul. 7, 2004. See also Forster, et al., (2003) "Programming peptidomimetic synthetases by translating genetic codes designed de novo" Proc Natl Acad Sci USA 100:6353-6357; and Feng, et al., (2003) "Expanding tRNA recognition of a tRNA synthetase by a single amino acid change" Proc Natl Acad Sci USA 100:5676-5681. Additional details can be found in U.S. Pat. Nos. 7,045,337; 7,083,970; 7,238,510; 7,129,333; 7,262,040; 7,183,082; 7,199,222; and 7,217,809.

Orthogonal Aminoacyl-tRNA Synthetase (O—RS)

The O—RS of systems used to produce unnatural polypeptides as used herein, preferentially aminoacylates an O-tRNA with an unnatural amino acid either in vitro or in vivo. The O—RS can be provided to the translation system, e.g., an E. coli cell, by a polypeptide that includes an O—RS and/or by a polynucleotide that encodes an O—RS or a portion thereof.

General details for producing an O—RS, assaying its aminoacylation efficiency, and/or altering its substrate specificity can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS"; and WO 2004/094593, entitled "EXPANDING THE EUKARYOTIC GENETIC CODE." See also, Wang and Schultz "Expanding the Genetic Code," Angewandte Chemie Int Ed 44:34-66 (2005); and Hoben and Soll (1985) Methods Enzymol 113:55-59, the contents of which are incorporated by reference in their entirety. Additional details concerning such systems can be found in U.S. Pat. Nos. 7,045,337; 7,083,970; 7,238,510; 7,129,333; 7,262,040; 7,183,082; 7,199,222; and 7,217,809.

Source and Host Organisms

The orthogonal translational components (O-tRNA and O—RS) that can optionally be used to create the unnatural immunogens of the invention, can be derived from any organism, or a combination of organisms, for use in a host translation system from any other species, with the caveat that the O-tRNA/O—RS components and the host system work in an orthogonal manner. It is not a requirement that the O-tRNA and the O—RS from an orthogonal pair be derived from the same organism. For example, the orthogonal components can be derived from archaebacterial genes for use in a eubacterial host system.

Furthermore, the orthogonal O-tRNA can be derived from an archaebacterium, such as Methanococcus jannaschii, Methanobacterium thermoautotrophicum, Halobacterium such as Haloferax volcanii and Halobacterium species NRC-1, Archaeoglobus fulgidus, Pyrococcus furiosus, Pyrococcus horikoshii, Aeuropyrum pernix, Methanococcus maripaludis, Methanopyrus kandleri, Methanosarcina mazei (Mm), Pyrobaculum aerophilum, Pyrococcus abyssi, Sulfolobus solfataricus (Ss), Sulfolobus tokodaii, Thermoplasma acidophilum, Thermoplasma volcanium, or the like, or a eubacterium, such as Escherichia coli, Thermus thermophilus, Bacillus subtilis, Bacillus stearothermphilus, or the like, while the orthogonal O—RS can be derived from an organism or combination of organisms, e.g., an archaebacterium, such as Methanococcus jannaschii, Methanobacterium thermoautotrophicum, Halobacterium such as Haloferax volcanii and Halobacterium species NRC-1, Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium, or the like, or a eubacterium, such as Escherichia coli, Thermus thermophilus, Bacillus subtilis, Bacillus stearothermphilus, or the like. In other systems, eukaryotic sources, e.g., plants, algae, protists, fungi, yeasts, animals, e.g., mammals, insects, arthropods, or the like can also be used as sources of O-tRNAs and O—RSs. Furthermore, the individual components of an O-tRNA/O—RS pair can be derived from the same organism or different organisms.

The O-tRNA, O—RS or O-tRNA/O—RS pair can be selected or screened in vivo or in vitro and/or used in a cell, e.g., a eubacterial cell, to produce a polypeptide with an unnatural amino acid. The eubacterial cell used is not limited and can include, for example, Escherichia coli, Thermus thermophilus, Bacillus subtilis, Bacillus stearothermphilus, or the like.

Selector Codons

Various selector codons expand the genetic codon framework of protein biosynthetic machinery. For example, a selector codon can include, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. Conventional site-directed mutagenesis can be used to introduce the selector codon at the site of interest in a polynucleotide encoding a polypeptide of interest (e.g., a self antigen of a subject, etc.). See, e.g., Sayers, et al., (1988) "5', 3' Exonuclease in phosphorothioate-based oligonucleotide-directed mutagenesis" Nucl Acid Res 16:791-802. By using different selector codons, multiple orthogonal tRNA/synthetase pairs can be used that allow the simultaneous site-specific incorporation of multiple unnatural amino acids e.g., including at least one unnatural amino acid, using these different selector codons.

Unnatural amino acids can also be encoded with rare codons. For example, when the arginine concentration in an in vitro protein synthesis reaction is reduced, the rare arginine codon AGG has proven to be efficient for insertion of Ala by a synthetic tRNA acylated with alanine. See, e.g., Ma, et al., (1993) "In vitro protein engineering using synthetic tRNA$^{Ala}$ with different anticodons" Biochemistry 32:7939-7945. In such case, the synthetic tRNA competes with the naturally occurring tRNA$^{Arg}$, which exists as a minor species in Escherichia coli. In addition, some organisms do not use all triplet codons. An unassigned codon AGA in Micrococcus luteus has been utilized for insertion of amino acids in an in vitro transcription/translation extract. See, e.g., Kowal and Oliver, (1997) "Exploiting unassigned codons in Micrococcus luteus for tRNA-based amino acid mutagenesis" Nucl Acid Res 25:4685-4689.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Particular methods of incorporating unnatural amino acids into proteins, e.g., unnatural immunogens such as any of the unnatural TNFαs described below, or, indeed, any target moiety of interest, can include using extended codons based on frameshift suppression. Four or more base codons can insert, e.g., one or multiple unnatural amino acids, into the same protein. In other instances, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson, et al., (2002) "Exploring the Limits of Codon and Anticodon Size" *Chemistry and Biology* 9:237-244; Magliery, et al., (2001) "Expanding the Genetic Code: Selection of Efficient Suppressors of Four-base Codons and Identification of "Shifty" Four-base Codons with a Library Approach in *Escherichia coli*" *J Mol Biol* 307:755-769; Ma, et al., (1993) "In vitro protein engineering using synthetic tRNA$^{Ala}$ with different anticodons" *Biochemistry* 32:7939; Hohsaka, et al., (1999) "Efficient Incorporation of Normatural Amino Acids with Large Aromatic Groups into Streptavidin in In Vitro Protein Synthesizing Systems" *J Am Chem Soc* 121:34-40; and Moore, et al., (2000) "Quadruplet Codons: Implications for Code Expansion and the Specification of Translation Step Size" *J Mol Biol* 298:195-209. Four base codons have been used as selector codons in a variety of orthogonal systems. See, e.g., WO 2005/019415; WO 2005/007870; and WO 2005/07624. See also, Wang and Schultz, (2005) "Expanding the Genetic Code" *Angewandte Chemie Int Ed* 44:34-66.

For a given system, a selector codon can also include one of the natural three base codons, where the endogenous system does not use (or rarely uses) the natural base codon. For example, such can include a system that is lacking a tRNA that recognizes the natural three base codon, and/or a system where the three base codon is a rare codon.

Selector codons optionally include unnatural base pairs. Descriptions of unnatural base pairs which can be adapted for use with the methods and compositions herein include, e.g., Hirao, et al., (2002) "An unnatural base pair for incorporating amino acid analogues into protein" *Nature Biotechnology* 20:177-182. See also, Wu, et al., (2002) "Enzymatic Phosphorylation of Unnatural Nucleosides" *J Am Chem Soc* 124: 14626-14630.

As stated above, in different embodiments of the invention, unnatural immunogens (that can be used either to produce an immune response in a subject or to produce cross-reactive antibodies that, in turn, can be administered to a subject) can be constructed in various fashions. For example, the unnatural immunogens can typically be constructed via direct incorporation methods such as an orthogonal translation system or an in vitro translation system or through solid-phase synthesis. However, indirect incorporations such as chemical modification and post-translational modification can done when in conjunction with (or in addition to) orthogonal translation system methods or in vitro translation system methods or as further modification to amino acids added through orthogonal or in vitro translation systems (or to natural amino acids in such already constructed molecules). It will be appreciated that various embodiments of the invention can include unnatural immunogens constructed through a number of available methods.

Non-Orthogonal Methods for the Incorporation of Unnatural Amino Acids into Immunogens Further to the above, various non-orthogonal strategies can be employed to introduce unnatural amino acids into moieties herein (or to modify unnatural amino acids incorporated into target moieties (e.g., disease related moieties) through orthogonal methods) to produce unnatural immunogens (e.g., in combination with the orthogonal methods above). It will be appreciated that in typical embodiments herein, an unnatural amino acid is incorporated into an immunogen during construction of the immunogen (e.g., when the immunogen is being translated, created/synthesized, etc.) and is not added through later chemical modification or post-translational modification. Thus, in some embodiments, derivatization of amino acids with reactive side-chains such as Lys, Cys and Tyr, e.g., the conversion of lysine to $N^2$-acetyl-lysine, can be used in conjuction with and/or in addition to orthogonal methods or other direct incorporation methods. Chemical synthesis can also provide a method to incorporate unnatural amino acids. See, e.g., Dawson, et al., *Annu. Rev. Biochem.*, 69:923 (2000).

In another example, a general in vitro biosynthetic method in which a suppressor tRNA chemically acylated with the desired unnatural amino acid is added to an in vitro extract capable of supporting protein biosynthesis, as has been used to site-specifically incorporate over 100 unnatural amino acids into a variety of proteins of virtually any size can be used herein to create unnatural immunogens. See, e.g., Cornish, et al., *Angew. Chem. Int. Ed. Engl.*, 1995, 34:621 (1995); Noren, et al., *Science* 244 182-188 (1989); and, Bain, et al., *J. Am. Chem. Soc.* 111 8013-8014 (1989).

An in vivo method, termed selective pressure incorporation, can also be used to exploit the promiscuity of wild-type synthetases and thus create unnatural immunogens herein. See, e.g., Budisa, et al., *FASEB J.*, 13:41 (1999). In such an auxotrophic strain, the relevant metabolic pathway supplying the cell with a particular natural amino acid is switched off, and the strain is grown in minimal media containing limited concentrations of the natural amino acid while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. See, e.g., Minks, et al., *Anal. Biochem.*, 284:29 (2000); Duewel, et al., *Biochemistry*, 36:3404 (1997); and Tang, et al., *Angew. Chem. Int. Ed. Engl.*, 40:1494 (2001). For additional examples, see, e.g., Hendrickson, et al., *EMBO J.*, 9:1665 (1990); Boles, et al., *Nat. Struct. Biol.*, 1:283 (1994); Budisa, et al., *Eur. J. Biochem.*, 230:788 (1995); Budisa, et al., *J. Mol. Biol.*, 270:616 (1997); vanHest et al., *FEBS Lett.*, 428:68 (1998); van Hest, et al., *J. Am. Chem. Soc.*, 122:1282 (2000); and, Kiick et al., *Tetrahedron*, 56:9487 (2000).

Yet another optional/additional strategy to incorporate unnatural amino acids into immunogens herein is to modify synthetases that have proofreading mechanisms. These synthetases cannot discriminate, and therefore charge tRNAs with amino acids that are structurally similar to the cognate natural amino acids with which the tRNAs are ordinarily charged. This error is corrected at a separate site of the synthetase, which deacylates the mischarged amino acid from the tRNA to maintain the fidelity of protein translation. If the proofreading activity of the synthetase is disabled, tRNAs charged with structural analogs of the amino acids with which they are normally charged can escape the editing function and incorporate the structural amino acid analog into a growing polypeptide chain. See, Doring, et al., *Science,* 292:501 (2001).

Solid-phase synthesis and semisynthetic methods can also be used for the synthesis of immunogens containing unnatural amino acids herein. For example, see the following publications and references cited within: Crick, et al., *Nature,* 1227-1232 (1961); Hofmann, et al., *J. Am. Chem,* 5914-5919 (1966); Kaiser, et al., *Acc Chem Res,* 47-54 (1989); Nakatsuka, et al., *J Am Chem Soc,* 3808-3810 (1987); Schnolzer, et al., *Science,* 221-225 (1992); Chaiken, et al., *CRC Crit. Rev Biochem,* 255-301 (1981); Offord, *Protein Eng.,* 151-157 (1987); and, Jackson, et al., *Science,* 243 (1994).

Chemical modification can be used in the various embodiments herein to introduce a variety of unnatural side chains, including cofactors, spin labels and oligonucleotides into unnatural immunogens of the invention. Again, chemical modification along with other post-translational modifications are typically used, if at all, as an adjuct to the direct incorporation methods such as orthogonal translation. Thus, chemical modification can optionally be used in combination with the orthogonal or other methods above such as to modify unnatural amino acids incorporated through orthogonal methods. See, e.g., Corey, et al., *Science,* 1401-1403 (1987); Kaiser, et al., *Rev Biochem,* 565-595 (1985); Kaiser, et al., *Science,* 505-511 (1984); Neet, et al., *J. Biol. Chem.,* 6392-6401 (1968); Polgar, et al., *J. Am. Chem Soc,* 3153-3154 (1966); and, Pollack, et al., *Science,* 1038-1040 (1988).

Alternatively, biosynthetic methods that employ chemically modified aminoacyl-tRNAs as have been used to incorporate several biophysical probes into proteins synthesized in vitro can be used herein to create unnatural immunogens. See the following publications and their cited references: Brunner, J., *Annu. Rev Biochem,* 483-514 (1993); and, Krieg, et al., *Proc. Natl. Acad. Sci,* 8604-8608 (1986).

Unnatural amino acids can also be site-specifically incorporated into unnatural immunogens of the invention by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, et al., *Science,* 244:182-188 (1989); Nowak, et al., *Science* 268:439-42 (1995); Bain, et al., *J. Am. Chem Soc,* 111:8013-8014 (1989); Budisa et al., *FASEB J.,* 13:41-51 (1999); Ellman et al., *Methods in Enz.,* 301-336 (1992); and, Mendel, et al., *Annu Rev Biophys. Biomol Struct.,* 24, 435-62 (1995).

Microinjection techniques can also be used to incorporate unnatural amino acids into unnatural immunogens of the invention. See, e.g., Nowak, et al., *Science,* 268:439 (1995); and Dougherty, *Curr. Opin. Chem. Biol.,* 4:645 (2000). See also, e.g., Turcatti, et al., *J. Biol. Chem.,* 271:19991 (1996); Gallivan, et al., *Chem. Biol.,* 4:739 (1997); Miller, et al., *Neuron,* 20:619 (1998); England, et al., *Cell,* 96:89 (1999); and, Lu, et al., *Nat. Neurosci.,* 4:239 (2001).

Solid phase peptide synthesis is another method that is widely used to chemically synthesize peptides and small proteins that comprise unnatural amino acids (see, e.g., Merrifield (1963) "Solid Phase Peptide synthesis. I. The synthesis of a tetrapeptide." *JACS* 85:2149-2154) and which can be adapted to produce unnatural immunogens of the invention. This technique typically comprises two stages: The first stage SPPS can include the assembly of a peptide chain using protected amino acid derivatives on a polymeric support via repeated cycles of coupling-deprotection. The free N-terminal amine of a solid-phase attached peptide can then be coupled to a single N-protected amino acid unit. This unit is then deprotected, revealing a new N-terminal amine to which a further amino acid may be attached. In the second stage of SPPS, the peptide is cleaved from the support and side-chain protecting groups are removed to produce the peptide, e.g., a peptide comprising one or more unnatural amino acids. There are two major used forms of solid phase peptide synthesis: Fmoc (Carpino, et al. (1972) "9-Fluorenylmethoxycarbonyl amino-protecting group." *J Org Chem* 37:3404-3409), in which a base labile alpha-amino protecting group is used, and t-Boc, in which an acid labile protecting group is used. Each method involves different resins and amino acid side-chain protection and consequent cleavage/deprotection steps.

Protein semi-synthesis can also be used to incorporate an unnatural amino acid into a protein to produce an unnatural immunogen herein. Protein semisynthesis often uses a split intein, a section of a protein that can excise itself and reattach the remaining portions, e.g., the exteins, to give a newly active protein called the splicing product. For example, one protein domain that does not comprise an unnatural amino acid can be used with a second protein domain that does comprise an unnatural amino acid, thus producing an unnatural immunogen. This strategy can be of beneficial use to produce unnatural immunogens that are difficult to express in in vivo protein expression systems.

A variety of chemical ligation techniques can also be used to incorporate an unnatural amino acid into a protein herein, e.g., during protein semi synthesis, thus producing an unnatural immunogen. For example, in a native chemical ligation (NCL) reaction, a peptide comprising an N-terminal cysteine reacts with, e.g., an unnatural amino acid comprising an α-thioester group, e.g. a C-terminal thioester, in the presence of an exogenous thiol catalyst to yield a native peptide bond at the site of ligation (Dawson, et al. (1994) "Synthesis of Proteins by Native Chemical Ligation" *Science* 266:776-779). Expressed protein ligation (EPL) is a protein engineering approach that allows recombinant and synthetic polypeptides to be chemoselectively and regioselectively joined together. This approach makes the primary structure of most proteins accessible to the tools of synthetic organic chemistry, enabling the addition of any of a variety of unnatural amino acids to be incorporated into a protein to produce an unnatural immunogen. Further details regarding these and other protein chemical ligation techniques can be found in, e.g., Howl, ed. *Peptide Synthesis and Its Applications,* Humana Press: Totowa N.J., 2005 and others.

Additional Details Regarding Techniques

Additional useful references for producing RS and tRNA mutations, as well as a variety of recombinant and in vitro nucleic acid manipulation methods (including cloning, expression, PCR, and the like) include Berger and Kimmel, *Guide to Molecular Cloning Techniques, Methods in Enzymology volume* 152 Academic Press, Inc., San Diego, Calif. (Berger); Kaufman, et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley); Chen, et al. (ed) *PCR Cloning Protocols. Second Edition* (Methods in Molecular Biology, volume 192) Humana Press; and in Viljoen, et al. (2005) *Molecular Diagnostic PCR Handbook* Springer, ISBN 1402034032.

A variety of protein methods are known and can be used to isolate, detect, manipulate or otherwise handle a protein produced according to the invention, e.g., from recombinant cultures of cells expressing any unnatural immunogen of the invention. A variety of protein isolation and detection methods are well known in the art, including, e.g., those set forth in R. Scopes, *Protein Purification*, Springer-Verlag, N.Y. (1982); Deutscher, *Methods in Enzmmology Vol.* 182: Guide to Protein Purification, Academic Press, Inc. N.Y. (1990); Sandana (1997) *Bioseparation of Proteins*, Academic Press, Inc.; Bollag, et al. (1996) *Protein Methods*. $2^{nd}$ *Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* $3^{rd}$ *Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000). These available methods can be used (optionally in conjunction with other protein purification methods) to isolate and/or purify unnatural immunogens produced through various methods herein (e.g., through orthogonal translation methods) in order to, e.g., prepare immunogens to use in treatments, vaccines, or other aspects of the current invention.

Antibodies and Antibody Production

In some embodiments, the invention comprises one or more antibody against an immunogen (i.e., an unnatural disease-related moiety that comprises one or more unnatural amino acid), which antibody can be administered to a subject. As detailed above, such an antibody is typically cross-reactive with a corresponding target moiety within the subject, or that is capable of being within the subject, which natural target moiety does not comprise an unnatural amino acid and from which the "unnatural" immunogen is derived or to which the immunogen corresponds.

As described above, an antibody refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies of the invention can exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1999), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or synthesized de novo using recombinant DNA methodologies. Particular antibodies include single chain antibodies (antibodies that exist as a single polypeptide chain), or single chain Fv antibodies (sFv or scFv) in which a variable heavy and a variable light chain are joined together (directly or through a peptide linker) to form a continuous polypeptide. The single chain Fv antibody is a covalently linked VH-VL heterodimer that can be expressed from a nucleic acid including VH- and VL-encoding sequences either joined directly or joined by a peptide-encoding linker. See, Huston, et al. (1988) *Proc. Nat. Acad. Sci. USA*, 85:5879-5883. While the VH and VL are connected to each as a single polypeptide chain, the VH and VL domains associate non-covalently. The scFv antibodies and a number of other structures converting the naturally aggregated, but chemically separated light, and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Antibodies useful in the current invention include polyclonal and monoclonal antibodies.

The unnatural immunogens of the invention, or their fragments, can be used to produce antibodies of the invention. Polyclonal antibodies, humanized antibodies, monoclonal antibodies, or antibody fragments can be produced using the unnatural immunogens of the invention. The antibodies can be purified by standard methods to provide antibody preparations that are substantially free of unwanted contaminants, e.g., serum proteins, that may affect their reactivity. For polyclonal antibodies, a selected mammal, (e.g., mouse, rabbit, goat, horse, etc.) can be immunized with an unnatural immunogen of the invention. Serum from the immunized animal can then be collected and treated according to procedures well known to those of skill in the art. Furthermore, polyclonal antibodies can be purified by immunoaffinity chromatography, again using procedures well known to those of skill in the art.

Alternatively, or additionally, monoclonal antibodies against an unnatural immunogen of the invention can be created. The making of monoclonal antibodies through hybridoma technology is well known to those of kill in the art. For example, an immortal cell line that produces an antibody of the invention can be created by cell fusion, or by other techniques, e.g., direct transformation of B lymphocytes with oncogenic DNA, transfection with Epstein-Barr virus, etc. See, e.g., Schreier, et al., Hybridoma Techniques (1980); Hammerling, et al., Monoclonal Antibodies and T-cell Hybridomas (1981); Kennett et al., Monoclonal Antibodies (1980); U.S. Pat. Nos. 4,341,761; 4,399,121; 4,427,783; 4,444,887; 4,452,570; 4,466,917; 4,472,500; 4,491,632; and 4,493,890, etc.

As those of skill in the art readily appreciate, other numerous well-known protocols exist to guide design and production of antibodies (e.g., monoclonal, polyclonal, humanized, etc.). Antibodies also can be prepared by any of a number of commercial services (e.g., Berkeley Antibody Laboratories, Bethyl Laboratories, Anawa, Eurogenetec, etc.).

Anti-TNFα Immunotherapy Based on an Unnatural TNFα Immunogen Comprising an Antibody-Accessible P-Nitrophenylalanine In a particular embodiment, described in further detail in the Examples below, the invention provides compositions and methods that can be useful in the treatment and/or prevention of pathologies associated with the activity of TNFα.

Tumor necrosis factor alpha (TNFα) plays a crucial role in the pathogenesis of many chronic inflammatory diseases, including Crohn's disease, endotoxic shock, cerebral malaria, rheumatoid arthritis, and others. A major challenge in the treatment and/or prevention of these diseases has been the development of methods that permit the immune system to selectively overcome tolerance to endogenous TNFα in order to stimulate the production of TNFα-neutralizing antibodies.

Neutralizing TNFα can alleviate symptoms of such diseases. For example, anti-TNFα antisera have been employed in numerous experiments to determine their therapeutic potential (reviewed in Veres, et al., (2007) "Infliximab therapy for pediatric Crohn's disease" *Expert Opin Biol Ther* 7:1869-1880; Ackermann, et al. (2007) "Tumor necrosis factor as a therapeutic target of rheumatologic disease" *Expert Opin Ther Targets* 8:2553-68, Knight, et al. (1993) "Construction and initial characterization of a mouse-human chimeric anti-TNF antibody" *Mol Immunol* 30:1443-1453; Present, et al. (1999) "Infliximab for the Treatment of Fistulas in Patients with Crohn's Disease" *New Engl J Med* 340:1398-1405). Soluble chimeric TNFα receptors have also been studied for their efficacy in minimizing the symptoms associated with arthritis, septic shock, and Crohn's disease (Peppel, et al. (1991) "A tumor necrosis factor (TNF) receptor-IgG heavy chain chimeric protein as a bivalent antagonist of TNF activity." *J Exp Med* 174:1483-1489; Williams, et al. (1995) "Successful therapy of collagen-induced arthritis with TNF receptor-IgG fusion protein and combination with anti-CD4" *Immunology* 84:433-439; Hoy, et al. (2007) "Etanercept: A Review of its Use in the Management of Ankylosing Spondylitis and Psoriatic Arthritis" *Drugs* 67:2609-2633; Fisher, et al. (1996) "Treatment of Septic Shock with the Tumor Necrosis Factor Receptor:Fc Fusion Protein" *New Eng J Med* 334:1697-1702; Korzenik (2004) "Crohn's disease: future anti-tumor necrosis factor therapies beyond infliximab" *Gastro Clin of North Am* 33:285-301). Breaking a subject's immunological tolerance to self-TNFα is one strategy by which TNFα-associated diseases can be treated and/or prevented.

The challenge of breaking immunological tolerance has been attempted by a number of strategies, described and referenced elsewhere herein. Some embodiments of the present invention provide an unnatural TNFα, i.e. a TNFα that comprises unnatural amino acid (UAA), that, when administered to a subject, stimulates or enhances an immunological response against an endogenous TNFα, e.g., a TNFα that may or may not be present in the subject at serum levels and/or expression levels that represent a disease state. Also provided herein are treatments for and vaccines against disease states, e.g. those listed herein associated with the presence or level of presence of TNFα, that entail administering anti-unnatural TNFα antibodies, which antibodies are cross-reactive with a natural TNFα, to attenuate or prevent the symptoms associated with TNFα-related disease states.

In general, elevated serum levels of TNFα are associated with a variety of disease states. It will be appreciated, however, that a subject in whom the immunological response is created and/or to whom the prophylactic treatment is administered, etc may not exhibit at serum TNFα levels that represent a disease state. Thus, it should be appreciated that the antibodies, and/or the unnatural immunogens of the invention can be administered both to individuals who do exhibit a TNFa-associated disease as well as those who do not.

Methods for producing an unnatural TNFα comprising any unnatural amino acid, e.g., any of the unnatural TNFαs described herein, are elaborated herein in UNNATURAL IMUNOGENS and UNNATURAL IMMUNOGEN PRODUCTION and in the Examples. Although the unnatural TNFαs described in the Examples below have been produced using orthogonal translation systems, it will be appreciated that unnatural TNFαs can also be produced using any one or more of the non-orthogonal methods detailed herein that are not chemical modifications or post-translational modifications (e.g., selective pressure incorporation, solid-phase synthesis, protein semi-synthesis, and others).

In an embodiment described herein, an unnatural TNFα comprises a highly immunogenic (E. Keinan, Ed. *Catalytic Antibodies* (Wiley-VCH, Weinheim, 2005) pp. 1-28), structurally conservative, antibody accessible p-nitrophenylalanine (pNO$_2$Phe, FIG. 1A) residue at amino acid position 86, e.g., pNO$_2$Phe$^{86}$TNFα. In this embodiment, the substitution mutation permits the unnatural TNFα, e.g., pNO$_2$Phe$^{86}$ mTNFα, to maintain a tertiary and quaternary protein structure that is substantially similar to that of the self-TNFα, thus increasing the probability that neutralizing antibodies produced against the unnatural TNFα, e.g., pNO$_2$Phe$^{86}$ mTNFα, can cross react with corresponding epitopes on the natural mTNFα, e.g., a mouse TNFα. As detailed above, the replacement of and/or addition of an unnatural amino acid can optionally not change (or not significantly change) the conformational structure of the unnatural TNFα as compared to the endogenous natural TNFα. Additional unnatural mTNFα derivatives (e.g., of GenBank Accession No. NP_038721) that can find use in therapeutic and/or prophylactic treatments in a mouse subject include a pNO$_2$Phe$^{11}$-mTNFα, a pNO$_2$Phe$^{19}$-mTNFα, a pNO$_2$Phe$^{21}$-mTNFα, a pNO$_2$Phe$^{42}$-mTNFα, a pNO$_2$Phe$^{49}$-mTNFα, a pNO$_2$Phe$^{104}$-mTNFα, or a pNO$_2$Phe$^{113}$-mTNFα. Unnatural hTNFαs derivations (e.g., of GenBank Accession No. AAA61200) that can find use in therapeutic and/or prophylactic treatments in a human subject include a pNO$_2$Phe$^{11}$-hTNFα, a pNO$_2$Phe$^{19}$-hTNFα, a pNO$_2$Phe$^{21}$-hTNFα, a pNO$_2$Phe$^{42}$-hTNFα, a pNO$_2$Phe$^{49}$-hTNFα, a pNO$_2$Phe$^{87}$-hTNFα, a pNO$_2$Phe$^{105}$-hTNFα, or a pNO$_2$Phe$^{114}$-hTNFα.

In general, elevated serum levels of TNFα are associated with a variety of disease states. Again, it will be appreciated, however, that a subject in whom the immunological response is created and/or to whom the prophylactic treatment is administered, etc. may not exhibit at serum TNFα levels that represent a disease state. Thus, it should be appreciated that the vaccines, the antibodies, and/or the unnatural immunogens of the invention can be administered both to individuals who do exhibit a TNFα-associated disease as well as those who do not.

Anti-RBP4 Immunotherapy Based on an Unnatural RBP Immuogen Comprising an Antibody-Accessible P-Nitrophenylalanine In embodiments described in Example 2, the methods and compositions of the invention can be beneficially used to treat and/or prevent of RBP4-associated diseases. RBP4, a low molecular weight serum protein, is secreted from the liver and adipose tissue and is the principal carrier of 90% of serum vitamin A. Excess levels of RBP4 contribute to such visual diseases as Matthew Wood Syndrome, age-related macular degeneration (AMD), and Stargardt's disease, among other conditions. Furthermore, elevated levels of serum RBP4 are also known to contribute to the development of insulin resistance and/or diabetes. Some embodiments of the present invention provide an unnatural RBP4, i.e., an RBP4 that comprises an unnatural amino acid, that can be administered to a subject to treat and/or prevent these diseases, e.g., by stimulating an antibody, B cell, or T cell response against a corresponding natural RBP4. It will be appreciated, however, that here too, a subject in whom the immunological response is created and/or to whom the prophylactic treatment is administered, etc. may not exhibit at serum RBP4 levels that represent a disease state. Thus, it should be appreciated that the vaccines, the antibodies, and/or the unnatural immunogens of the invention can be administered both to individuals who do exhibit a RBP4-associated disease as well as those who do not.

The methods that can be used to produce an unnatural TNFα, elaborated herein, can also be used to produce an unnatural RBP4. The unnatural RBP4 can include any unnatural amino acid described herein that is incorporated into the unnatural RBP4 in a method that is other than post-translational modification or chemical modification. Any natural RBP4 can be substituted with any unnatural amino acid to produce an unnatural RBP4. The substitution need not replace the natural amino acid with a structurally conservative unnatural amino acid. Alternatively or additionally, one or more additional unnatural amino acids can be added to an RBP4 polypeptide to produce an unnatural RBP4. The unnatural RBP4 can optionally comprise a structure that is substantially similar to the natural RBP4, thus increasing the probability that neutralizing antibodies produced against the unnatural RBP4 can cross react with corresponding epitopes on the natural RBP4. Unnatural RBP4s that can find use in therapeutic and/or prophylactic treatments in a subject include a $pNO_2Phe^{43}$ mRBP4 and a $pNO_2Phe^{108}$ mRBP4, as well corresponding human constructs, etc.

Administration and Formulation

Antibody and/or Immunogen Formulations

In order to produce or enhance an immunological response against a target moiety, e.g., a TNFα, or any other of the myriad possible targets noted herein, the treatment methods of the invention can employ an antibody against an immunogen, e.g., a derivative of the target moiety that comprises one or more unnatural amino acids, and/or employ the immunogen itself, e.g., an unnatural TNFα. Typically, such antibodies and/or immunogens are present in combination with a physiologically acceptable adjuvant, excipient, and/or stabilizer that is non-toxic to recipients (e.g., subjects) at the dosages employed. It will be appreciated, however, that the current invention is not necessarily limited by the specific formulations of antibody and/or immunogen preparations.

Formulations of antibodies and/or immunogens (i.e., derivatives of target moieties that comprise one or more unnatural amino acids) can include a physiologically acceptable adjuvant, excipient, and/or stabilizer. Excipients known in the art include, for example, vegetable and animal oils and fats. Stabilizing agents, wetting and emulsifying agents, salts for varying the osmotic pressure, buffers for maintaining a desirable pH, and/or skin penetration enhancers can be used as auxiliary (i.e., excipient) agents in the various formulations. Methods for preparing various conventional dosage forms are known or will be apparent to those skilled in the art; for example, see, Remington: The Science and Practice of Pharmacy (21$^{st}$ Edition, Lippincott Williams & Wilkins, 2005). Formulation can also include one or more adjuvants such as alum, Freund's complete adjuvant (FCA), Freund's incomplete adjuvant (FIA), lipopolysaccharide (LPS), squalene, virosomes, MSP1, QS21, etc. Furthermore, the formulation can also comprise wherein the immunogen is fused to carriers such as a polypeptide carrier, a carbohydrate carrier (e.g., one or more units of a monosaccharide such as mannose, one or more units of mucin, etc.), keyhole limpet hemocyanin (KLH), ovalbumin, hen egg albumin, tetanus toxin or diphtheria toxin, etc. Those of skill in the art will be familiar with a number of adjuvants, carriers, excipients, stabilizers, etc., that can optionally be used with the current invention.

Furthermore, examples of common excipients that can be used for either antibody and/or immunogen formulations include buffers (such as phosphate buffer, citrate buffer, and buffers made from other organic acids), antioxidants (e.g., ascorbic acid), low-molecular weight (less than about 10 residues) polypeptides, additional proteins (such as serum albumin, gelatin, and an immunoglobulin), hydrophilic polymers (such as polyvinylpyrrolidone), amino acids (such as glycine, glutamine, asparagine, arginine, and lysine), monosaccharides, disaccharides, and other carbohydrates (including glucose, mannose, and dextrins), chelating agents (e.g., ethylenediaminetetraacetic acid [EDTA]), sugar alcohols (such as mannitol and sorbitol), salt-forming counter ions (e.g., sodium), and/or anionic surfactants (such as Tween™, Pluronics™, and PEG).

It will be appreciated that particular adjuvants, excipients, or stabilizers and formulations used can vary depending upon, e.g., whether the formulation comprises an antibody or an unnatural immunogen of the invention, the specific route of administration, other drugs given, dosage used, etc. For example, in intravenous, intramuscular or subcutaneous administration, the antibody or immunogen can be incorporated into a pharmaceutically acceptable and injectable excipient. Typically, the excipient is one such as sterile water, aqueous saline solution, aqueous buffered saline solution, aqueous dextrose solution, aqueous glycerol solution, ethanol, or combinations thereof. The preparation of such solutions ensuring sterility, proper pH, isotonicity, and stability is achieved according to protocols established in the art for administration of antibodies or antigenic proteins. Generally, an excipient is selected to minimize allergic and other undesirable effects, and to suit the particular route of administration, e.g., subcutaneous, intramuscular, etc.

In some embodiments, the formulations can be prepared for oral administration, e.g., incorporated into a food or drink, formulated into a chewable or swallowable tablet or capsule, etc. Such formulations, thus, allow rapid uptake in the bloodstream and distribution to various compartments of the body. Typically for oral administration, excipients can include pharmaceutical grades of lactose, mannitol, starch, methyl cellulose, magnesium stearate, sodium saccharine, talcum, cellulose, glucose, gelatin, sucrose, magnesium carbonate, and the like. When the composition is employed in the form of solid preparations for oral administration, the preparations may be tablets, granules, powders, capsules, etc.

In some embodiments, the invention utilizes sustained-release pharmaceutical formulations to deliver the antibody and/or unnatural immunogen. An exemplary sustained-release formulation comprises a semipermeable matrix of a solid hydrophobic polymer to which the antibodies and/or unnatural immunogens of the invention are attached or in which such are encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(−)-3-hydroxybutyric acid. Such matrices can be in the form of shaped articles, such as films, or microcapsules.

In the various methods herein, the immunogens, e.g., any of the unnatural TNFαs or any other immunogens described herein, or anti-immunogen antibodies that cross-react with target moieties can also be prepared in formulations to be administered to a subject transdermally. For transdermal administration, the antibody and/or unnatural immunogen can be incorporated into a lipophilic carrier and formulated as a topical cream or ointment or in an adhesive patch. Methods for preparing various conventional dosage forms are known or will be apparent to those skilled in the art; for example, see, Remington: The Science and Practice of Pharmacy ($21^{st}$ Edition, Lippincott Williams & Wilkins, 2005). Thus, a sustained-release formulation can include liposomally entrapped active agents. Liposomes are small vesicles composed of various types of lipids, phospholipids, and/or surfactants. These components are typically arranged in a bilayer formation, similar to the lipid arrangement of biological membranes. Liposomes containing antibodies/unnatural immunogens can be prepared by known methods, such as, for example, those described in Epstein, et al. (1985) *PNAS USA* 82:3688-92, and Hwang, et al., (1980) *PNAS USA,* 77:4030-34. Useful liposomes can be generated by the reverse-phase evaporation method, using a lipid formulation including, for example, phosphatidylcholine, cholesterol, and PEG-derivatized phosphatidylethanolamine (PEG-PE). If desired, liposomes can be extruded through filters of defined pore size to yield liposomes of a particular diameter.

In yet other embodiments, the antibodies and/or unnatural immunogens of the invention, such as those described throughout, can be prepared into formulations for mucosal administration. Mucosal administration includes such routes as buccal, endotracheal, inhalation, nasal, pharyngeal, rectal, sublingual, vaginal, etc. For administration through the mucosal membranes, the antibodies and/or unnatural immunogens can be formulated as an emulsion, gum, lozenge, spray, tablet or the like. Nasal administration can be conducted through a powder or spray formulation. For rectal and vaginal administration the formulations can comprise a cream, douche, enema or suppository, etc.

In some embodiments, the antibody and/or unnatural immunogens can be prepared into formulations for ocular administration by incorporating them into a solution or suspension adapted for ocular application, e.g., drops or sprays.

Pharmaceutical formulations utilized herein can also include the antibodies and/or unnatural immunogens adsorbed onto a membrane, such as a silastic membrane, which can be implanted, as described in International Publication No. WO 91/04014.

Pharmaceutical formulations utilized by the invention can be stored in any standard form, including, e.g., an aqueous solution or a lyophilized cake. Such formulations are typically sterile when administered to subjects. Sterilization of an aqueous solution is readily accomplished by filtration through a sterile filtration membrane. If the formulation is stored in lyophilized form, the formulation can be filtered before or after lyophilization and reconstitution.

Administration of Antibodies and/or Unnatural Immunogens

As described herein, the present invention concerns compositions and methods to produce or enhance an immunological response in a subject against a target moiety, e.g., a self moiety such as a TNFα, through administration of antibodies against an unnatural target moiety (an unnatural immunogen), which antibody is cross reactive with the target moiety and/or through administration of the unnatural target moiety itself. Such target moieties can include, for example, any of the unnatural TNFαs described in the Examples below as well as myriad other molecules, e.g., as described herein. Typically, the specific formulation is given either alone or in combination (e.g., co-administered) with other treatments or medications to therapeutically and/or prophylactically treat one or more of a number of medical conditions/disease states. It will be appreciated that depending upon whether an antibody against the unnatural immunogen is administered, whether an unnatural immunogen is administered, the specific formulation of the antibody and/or unnatural immunogen that is administered, etc., the administration/treatment regime can vary. Thus, in some embodiments, administration of an antibody of the invention is different (e.g., in dosage, time-course, etc.) than administration of an unnatural immunogen of the invention. It will also be appreciated that recitation of particular formulations and/or administration regimes herein should not necessarily be taken as limiting.

Those of skill in the art will be familiar with numerous medical/physiological/psychological tests and measurements to help in selection of subjects that are to be administered the compositions and/or to whom the methods of the invention are to be performed. For example detection of viral or bacterial infection or the like (e.g., HIV infection) is well known and widely practiced by those of skill in the art. Similarly, numerous diagnostic tests (e.g., based on symptoms and/or presence of specific infectious agents, etc.) are available for other medical disorders, e.g., cancer, autoimmune disorders (e.g., SLE), etc. Such determination can be used to help select subjects herein to which the unnatural immunogens and/or antibodies against such are to be administered. Furthermore, in some instances, subjects are optionally chosen based on their familial history, environmental exposure, etc. For example, subjects can be chosen based on a family history or family predisposition to a disease state (e.g., Alzheimer's disease, breast cancer, etc.). Also, subjects can optionally be chosen based on exposure or potential/risk of exposure to an infectious agent or other disease causative agent (e.g., exposure or possible exposure of sex workers to HIV, exposure or possible exposure of healthcare workers to hepatitis, exposure of workers to silica compounds possibly leading to silica-induced pulmonary fibrosis, etc.). Those of skill in the art will be familiar with additional examples.

Antibody Administration

The antibodies of the invention have therapeutic and/or prophylactic utility. Thus, in various embodiments, they can be used to, e.g., produce or enhance an immunological response against one or more specific target moieties. Therefore, the invention provides methods for treating one or more disease state (e.g., cancer, an autoimmune condition, a pathogenic infection, etc.) related to or associated with such target moiety by using antibodies of the invention. As explained throughout, antibodies of the invention can be used to treat and/or prevent numerous diseases and/or disorders. For example, diseases/disorders such as endotoxic shock, cerebral malaria, an autoimmune disorder, multiple organ failure, multiple sclerosis, cardiac dysfunction, atherosclerosis, ischemia-reperfusion injury, insulin resistance, rheumatoid arthritis, Crohn's disease, inflammatory bowel disease, cachexia, septic shock, AIDS, graft-versus-host disease, bactericidal granulomas, adult respiratory distress syndrome, and/or silica-induced pulmonary fibrosis, as well as numerous others, can be treated through use of the current invention. As explained above, the antibodies of the invention are specific for an unnatural immunogen (an unnatural disease-related moiety, such as an unnatural TNFα), but are cross-reactive with the corresponding target moiety that does not comprise an unnatural amino acid (such as a natural TNFα).

As will be appreciated, the various methods of the invention comprising antibody administration can optionally be used in combination with other therapeutic/prophylactic treatments (e.g., chemotherapy, antibiotic and/or antiviral treatment, surgery, etc.).

The antibodies of the invention can be administered to a subject through injection (e.g., intravenous, intraperitoneal, subcutaneous, or intramuscular injection), or by other methods such as infusion. The antibodies can also be administered via intratumoral, peritumoral, intralesional, or perilesional routes and therefore exert local as well as systemic effects.

Effective dosages, time courses, schedules, etc., for administering antibodies of the invention can be determined empirically. Those of skill in the art will be familiar with such tailoring of antibody treatment for numerous medical conditions. The parameters (e.g., dosage, time course, etc.) involved in antibody treatment of a subject can vary depending on, e.g., the individual subject to receive the antibodies (e.g., the subject's species, disease state, overall physical condition, etc.), the route of administration, the particular type of antibody used and other drugs being administered whether the treatment is prophylactic or therapeutic, etc. Further guidance in creating antibody treatment programs can be found throughout the literature, e.g., *Handbook of Monoclonal Antibodies*, Ferrone, et al., eds., Noges Publications, Park Ridge, N.J., (1985); Antibodies in Diagnosis and Therapy: Technologies Mechanisms and Clinical Data, CRC, 1999.

Unnatural Immunogen Administration

In other embodiments, the unnatural immunogens of the invention (i.e., versions of a target moiety which have one or more unnatural amino acid, including, but not limited to, any of the unnatural TNFαs or RBP4s described hereinbelow) can be administered to a subject in order for prophylactic and/or therapeutic treatment. As detailed herein, administration of such unnatural immunogens produces an immunological response in the subject, an antibody response against the unnatural immunogen. Furthermore, however, the antibodies produced by the subject against the unnatural immunogen, are preferably cross-reactive against a natural version of the target moiety (which corresponds to the unnatural immunogen) that is within the subject or that is capable of being in the subject (i.e., a disease-related moiety whether arising from pathogenic infection, cancer, an autoimmune condition, etc., but which does not comprise an unnatural amino acid).

In the methods herein, the unnatural immunogens, such as unnatural TNFαs or any of the other myriad possible targets listed herein, can be administered in any of the commonly accepted manners for administration of pharmaceutical compositions. Again, those of skill in the art will be quite familiar with such routes and delivery protocols. For example, routes of administration for unnatural immunogens can include, but are not limited to: oral, intracerebral, intrathecal, intraperitoneal, intramuscular, intravenous, subcutaneous, transdermal, mucosal (e.g., via suppository or intranasal or transbuccal administration) or ocular administration, etc. Thus, depending upon the route of administration, the unnatural immunogens can be provided in various dosage forms, such as, for example, tablets, capsules, powders, controlled-release formulations, suspensions, emulsions, suppositories, creams, ointments, lotions, or aerosols. See above. Particular embodiments utilize dosage forms suitable for simple administration of precise dosages.

Delivery can contain up to a full daily dose, or the unnatural immunogen can be delivered over an extended period, e.g., 3-10 days, in an amount effective to produce at least an average daily dose.

Where an antibody response (typically against the corresponding natural target moiety that does not comprise an unnatural amino acid) in a subject is weak or lower than desired, further administration of the unnatural immunogen can be performed (e.g., until the titer of the desired antibody increases sufficiently). Furthermore, after immunization with the unnatural immunogen, serum samples can be taken from the subject to test for production of the desired antibodies.

Co-Administration of Antibodies and/or Unnatural Immunogens and Other Compositions If desired, administration of antibodies and/or unnatural immunogens of the invention can be performed in conjunction with administration of one or more other drug or treatment. The antibodies/unnatural immunogens can be administered in the same formulation as another drug, or can be administered separately (e.g., at separate times, in different formulations, according to different schedules, according to different criteria, etc.). Furthermore, in various embodiments, multiple antibody types and/or multiple unnatural immunogens can be administered to a subject, again, either concurrently or sequentially, optionally along with other drugs (or treatments).

The antibodies and/or unnatural immunogens of the invention can also be administered, either concurrently or sequentially, with various treatments such as surgery, radiation treatment, etc.

The additional drugs/treatments with which the antibodies and/or unnatural immunogens of the invention can be co-administered optionally are to treat the same particular aspect of the medical condition as the antibodies/unnatural immunogens of the invention (e.g., decrease of a particular target moiety within the subject) or can be to treat other or related (or even unrelated) medical conditions in the subject. Thus, the co-administered drugs/treatments can be to treat other aspects of an underlying medical condition (disease state). For example, in the various treatments, the antibodies and/or unnatural immunogens of the invention are optionally administered along with any of a number of common treatments, such as aspirin, salisylates, ibuprofen, naproxen, sulindac (e.g., Clinoril™), oxaprozin and tolmetin for fever, joint pain and inflammation, etc. In some embodiments, antimalarial drugs such as hydroxychloroquine, chloroquine and quinacrine can be indicated for treatment of malaria or for various skin abnormalities involved in other conditions (e.g., SLE). Corticosteroids, typically prednisone, can be administered for organ inflammation, etc. Some androgenic compounds, e.g., danazol (e.g., Danocrine™) can be used in controlling immune thrombocytopenia and severe hemolytic anemia.

Furthermore, the antibodies/unnatural immunogens of the invention can also be administered along with drugs that are effective for secondary conditions arising from the underlying medical condition or even arising from the treatment for the underlying medical condition. For example, in some embodiments, the treatments of the invention can be administered along with calcitonin to help treat bone density loss arising from treatment of various ancillary conditions that may arise from use of prednisone, methotrexate, immunosuppressants, anti-inflammatories, etc., in a treatment program.

Time-Course and Adjustment of Dosage of Antibodies and/or Unnatural Immunogens

As stated above, the range of antibody/unnatural immunogen dosages and dose rates effective for achieving the desired outcome in a subject (and, thus, optionally an effective treatment of a medical condition/disease state) can be determined in accordance with standard industry practices. These ranges can be expected to differ depending upon whether the desired response is the prophylactic, therapeutic or curative treatment of the medical condition (e.g., cancer, SLE, Sjogren's syndrome, bacterial infection, viral infection, scleroderma, allergic diseases, HIV/AIDS, etc.), the type or severity of symptoms, other medications being administered, the age, gender, medical history and other individual parameters of the subject being treated, etc. In some embodiments, the dosages can be determined based upon changes produced in particular levels of a target moiety, as measured, e.g., in changes as measured by ELISA or the like. To determine such levels in a subject, typical embodiments herein can measure the levels of the moiety in any one or more of a biological tissue, peripheral blood, serum, plasma, urine, vaginal fluid, semen, saliva, peritoneal fluid, lymphatic fluid, aqueous or vitreous humor, tears, pulmonary effusion or serosal fluid.

Those skilled in the art will be familiar with individual tailoring of treatment regimes to effect the desired outcome in various subjects. Thus, in many embodiments, while a particular dosage of antibody and/or unnatural immunogen is used as either a starting point or a target level, such dosage is optionally adjusted based on specific factors of the subject receiving treatment. For example, the dosage can be increased if the desired level of target moiety is not reached. Alternately or additionally, if/when the desired level is achieved, the dosage can be tapered down to find the lowest level that will achieve stability at the desired level.

The antibody/unnatural immunogen dosage can also be adjusted based upon symptoms of the underlying medical condition being treated. For example, if the subject is being treated for a particular medical condition, then symptoms of that particular condition are optionally used as guidelines or indicators for dosages (amounts and time courses). Thus, in some embodiments, evaluations of the severity of the condition, e.g., as measured by time intervals between outbursts of symptoms, etc., can be used as indirect measurement of progress of treatment, and, thus, administration can be tailored accordingly. Those of skill in the art will be aware of other tests/diagnostic scales capable of use to monitor symptoms in medical conditions.

Subjects to which Antibodies and/or Unnatural Immunogens Can Be Administered.

A variety of animals can benefit from vaccines, therapeutic treatments, and/or prohyllactic treatments provided by the invention, as well. Such animals include, but are not limited to, domestic livestock, such as cows, pigs, goats, sheep, chickens, and/or other common farm animals. Common household pets, e.g., cats, dogs, parrots, parakeets, etc., can also benefit from being administered a cross-reactive antibody against an unnatural immunogen and/or the immunogen itself.

Further details regarding the use of animal models and animal subjects in biomedical testing and veterinary treatment are elaborated in, e.g., Ng, Chow, and Ogden, eds. *Using Animal Models in Biomedical Research: A Primer for the Investigator*. First Edition. Singapore: World Scientific Publishing Company, 2008; Conn, ed. *Sourcebook of Models for Biomedical Research*. Totowa, N.J.: Springer, 2008; Woodhead, ed. *Nonmammalian Animal Models for Biomedical Research* (Vol 1). New York: Academic Press, 1990. See also, e.g., Adams, ed. Veterinary Pharmacology and Therapeutics. Eighth Edition. USA: Wiley-Blackwell, 2001; Kahn and Line, Eds. *Merck Veterinary Manual*. Ninth Edition. USA: Merck, 2005; and references cited therein.

Antibodies and/or unnatural immunogens provided by the invention can be administered not only to treat a disease state in a subject, e.g., a human, but also to perform treatment efficacy tests, as well as metabolic tests, toxicology tests, and specific tests to determine the effects of the antibodies and/or unnatural immunogens on reproductive function or embryonic toxicity, or to determine their carcinogenic potential. Performing such observational studies can entail administering the antibodies and/or unnatural immunogens of the invention to a variety of animal subjects. Those of skill in the art will be quite familiar with numerous medical tests and measurements to help in selection of animal subjects that are to be administered the compositions and/or to whom the methods of the invention are to be performed. Such animal subjects include, but are not limited to, e.g., mammals such as goats sheep, camels, cows, pigs, rabbits, horses, hamsters, non-human primates (monkeys, including cynomologous monkeys, baboons, Old World Monkeys, and chimpanzees), guinea pigs, rats, mice, and/or cats. Birds such as, e.g., domestic fowl (chickens, turkeys), cockatiels, psittacine birds, and cage and/or aviary birds, as well as bird embryos, can also be used in the research and development, production, quality control, or safety testing of antibodies and/or unnatural immunogens provided by the invention.

Fish, such as zebrafish, platyfish, and swordtails; amphibians, including, e.g., frogs and salamanders; and reptiles (snakes, lizards, and turtles) can also be used in a wide variety of tests to determine the safety, effective dose, and/or toxicology of the compositions described herein and/or the methods of their administration. See, e.g., Barry, et al. (2002) "Information Resources for Reptiles, Amphibians, Fish, and Cephalopods Used in Biomedical Research." United States Department of Agriculture National Agricultural Library Animal Welfare Information Center, and the references cited therein.

Kits and Articles of Manufacture

In some embodiments, the invention provides a kit or an article of manufacture containing materials useful for the methods and compositions described herein. Such kits can optionally comprise one or more containers, labels, and instructions, as well components for construction of antibodies and/or unnatural immunogens and/or actual antibodies and/or unnatural immunogens (e.g., unnatural TNFαs or any of the other myriad examples herein).

The kits can also optionally comprise one or more antibody (i.e., an antibody against an unnatural immunogen, which antibody is cross-reactive against a natural target moiety within a subject) and/or one or more unnatural immunogen as well as optionally other components (e.g., various antibiotics, various antifungal agents, etc.). Such unnatural immunogens can include, but are not limited to, any one or more of the unnatural TNFαs provided by the invention. The kits can optionally include tubes or other containers (e.g., of glass, plastic, nylon, cotton, polyester, metal, etc.) to store the components or in which to mix/prepare the components as well as one or more devices with which to administer such to a subject (e.g., a human in need of treatment, etc.). In some embodiments, the device with which to administer the components to the subject comprises the container in which the components are stored and/or mixed/prepared.

The kits can also optionally include additional components in addition to the antibody/unnatural immunogen components of the invention, e.g., buffers, diluents, filters, dressings, bandages, applicators, gauze, barriers, semi-permeable barriers, tongue depressors, needles, and syringes, etc.

In many embodiments, the kits comprise instructions (e.g., typically written instructions) relating to the use of the kit to treat a subject for one or more medical condition/disease state). In some embodiments, the kits comprise a URL address or phone number or the like for users to contact for instructions or further instructions. The kits can be unit doses, bulk packages (e.g., multi-dose packages), or sub-unit doses.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Breaking Immunological Tolerance with a Genetically Encoded Unnatural Amino Acid The ability to selectively induce a strong immune response against self-proteins, or increase the immunogenicity of specific epitopes in foreign antigens, would have a significant impact on the production of vaccines for cancer, protein-misfolding diseases, and infectious diseases. Here, we show that site-specific incorporation of an immunogenic unnatural amino acid into a protein of interest produces high-titer antibodies that cross-react with WT protein. Specifically, mutation of a single tyrosine residue ($Tyr^{86}$) of murine tumor necrosis factor-α (mTNFα) to p-nitrophenylalanine ($pNO_2Phe$) induced a high-titer antibody response in mice, whereas no significant antibody response was observed for a $Tyr^{86}{\rightarrow}Phe$ mutant. The antibodies generated against the $pNO_2Phe$ are highly cross-reactive with native mTNFα and protect mice against lipopolysaccharide (LPS)-induced death. This approach may provide a general method for inducing an antibody response to specific epitopes of self- and foreign antigens that lead to a neutralizing immune response.

A major challenge in modern vaccinology is the development of robust methods to selectively induce a strong immune response against self-proteins or to increase the immunogenicity of specific epitopes in foreign antigens that can elicit neutralizing antibodies but that are not immunodominant. A number of strategies are being pursued to address this challenge including the development of improved adjuvants, the introduction of foreign helper peptides into chimeric antigens, and the use of DNA vaccines (Dalum, et al. (1999) "Therapeutic antibodies elicited by immunization against TNF-alpha." *Nat Biotechnol* 17: 666-669; Makela, et al. (2002) "Evolution of conjugate vaccines." *Expert Rev Vaccines* 1: 399-410; Restifo, et al. (1996) "The new vaccines: building viruses that elicit anti-tumor immunity." *Curr Opin Immunol*, 8: 658-663; Baldridge, et al., *Vaccine Adjuvants: Immunological and Clinical Principles*. C. J. Hackett, Ham, D. A., Jr., Ed. (Humana Press, Totowa, N.J., 2006), pp 235-255). Interestingly, almost 50 years ago, Weigle (Weigle (1965) "The induction of autoimmunity on rabbits following injections of heterologous or altered homologous thyroglobulin." *J Exp Med* 121: 289-308) showed that rabbits immunized with a rabbit thyroglobulin that had been nonspecifically labeled with a diazonium derivative produced cross-reactive antibodies to native thyroglobulin. Although these early experiments produced a highly heterogeneous antigen, one interpretation is that chemical modification results in immunogenic epitopes that induce high-titer cross-reactive antibodies. Similarly, there is anecdotal evidence that T cell tolerance can be broken by autoreactive B cells, which are readily elicited by immunization with cross-reactive foreign antigens that differ from self-antigen by one or a few amino acids (Mamula, et al. (1992) Breaking T cell tolerance with foreign and self co-immunogens. A study of autoimmune B and T cell epitopes of cytochrome c." *J Immunol* 149: 789-795).

In contrast to the relatively nonselective chemical methods for modifying proteins, it is now possible to make highly precise "chemical mutations" to protein structure by means of genetically encoded unnatural amino acids. More than 50 unnatural amino acids have been encoded in bacteria, yeast, or mammalian cells including metal-binding and posttranslationally modified amino acids, fluorescent and redox-active amino acids, and photo- and chemically reactive amino acids (Wang, et al. (2001) Expanding the genetic code of *Escherichia coli*." *Science* 292: 498-500; Chin, et al. (2003) "An expanded eukaryotic genetic code." *Science* 301: 964-967; Xie and Schultz (2006) "A chemical toolkit for proteins—an expanded genetic code." *Nat Rev Mol Cell Biol* 7: 775-782). More specifically, the phenylalanine derivative p-nitrophenylalanine ($pNO_2Phe$, FIG. 1A) has been incorporated into proteins in bacteria in response to the amber nonsense codon with high fidelity and good efficiency for use as a spectroscopic distance probe (Tsao, et al. (2006) "The genetic incorporation of a distance probe into proteins in *Escherichia coli*." *J Am Chem Soc* 128: 4572-4573). Nitroaryl groups have historically been used as highly immunogenic haptens (Keinan, Ed., Catalytic Antibodies (Wiley-VCH, Weinheim, 2005), most likely because of the propensity of the electron-deficient pi system to interact with the Tyr and Trp side chains common to antibody combining sites. Because of their close structural similarity, we postulated that proteins containing either $Phe{\rightarrow}pNO_2Phe$ or $Tyr{\rightarrow}pNO_2Phe$ mutations might generate a robust immune response that would be cross-reactive with the native protein. Here, we show that immunization of mice with a $Tyr^{86}{\rightarrow}pNO_2Phe$ mutant of murine tumor necrosis factor-α (mTNFα) generates a high-titer antibody response to WT mTNFα that efficiently protects mice against a lipopolysaccharide (LPS) challenge.

mTNFα was chosen as the target protein for this study because: (i) it is a well characterized cytokine involved in the regulation of infectious, inflammatory, and autoimmune phenomena (Vassalli (1992) "The Pathophysiology of Tumor Necrosis Factors." *Ann Rev Immunol* 10: 411-452); (ii) the biological properties of this protein have been extensively studied including its expression, structure, function, and signaling mechanisms (Vassalli (1992) "The Pathophysiology of Tumor Necrosis Factors." *Ann Rev Immunol* 10: 411-452; Baeyens, et al. (1999) "The structure of mouse tumour-necrosis factor at 1.4 A resolution: towards modulation of its selectivity and trimerization." *Acta Crystallogr D Biol Crystallogr* 55: 772-778; Pennica, et al. (1985) "Cloning and expression in *Escherichia coli* of the cDNA for murine tumor necrosis factor." *Proc Natl Acad Sci USA* 82: 6060-6064: Pasparakis, et al. (1996) "Immune and inflammatory responses in TNF alpha-deficient mice: a critical requirement for TNF alpha in the formation of primary B cell follicles, follicular dendritic cell networks and germinal centers, and in the maturation of the humoral immune response." *J Exp Med* 184: 1397-1411; Baeyens, et al. (1997) "Crystallization and preliminary X-ray studies of mouse tumor necrosis factor." *Acta Crystallogr D Biol Crystallogr* 53: 329-330; B. B. Aggarwal, Vileck, J., Ed., *Tumor Necrosis Factors: Structure, Function and Mechanism of Action*. (Dekker, New York, 1992), pp. 1-587); and (iii) mTNFα knockout mice are viable and show no apparent phenotypic abnormalities (Pasparakis, et al. (1996) "Immune and inflammatory responses in TNF alpha-deficient mice: a critical requirement for TNF alpha in the formation of primary B cell follicles, follicular dendritic cell networks and germinal centers, and in the maturation of the humoral immune response." *J Exp Med* 184: 1397-1411), suggesting that mice will survive a neutralizing immune response against TNFα. In addition, anti-TNFα antibodies (Knight, et al. (1993) "Construction and initial characterization of a mouse-human chimeric anti-TNF antibody." *Mol Immunol* 30: 1443-1453; Present, et al. (1999) "Infliximab for the Treatment of Fistulas in Patients with Crohn's Disease." *New Engl J Med* 340: 1398-1405) and soluble chimeric TNFα receptors (Peppel, et al. (1991) "A tumor necrosis factor (TNF) receptor-IgG heavy chain chimeric protein as a bivalent antagonist of TNF activity." *J Exp Med* 174: 1483-1489; Williams, et al. (1995) "Successful therapy of collagen-induced arthritis with TNF receptor-IgG fusion protein and combination with anti-CD4." *Immunology* 84: 433-439) are widely used in the treatment of autoimmune disease, and a number of approaches are being pursued to develop TNFα-specific vaccines for clinical use. The latter include recombinant TNFα molecules containing foreign immunodominant T-helper epitopes, TNFα fusions to virus-like particles of the bacteriophage Q$^\beta$, and keyhole limpet hemocyanin-TNFα heterocomplexes (Dalum, et al. (1999) "Therapeutic antibodies elicited by immunization against TNF-alpha." *Nat Biotechnol* 17: 666-669, Spohn, et al. (2007) "A Virus-Like Particle-Based Vaccine Selectively Targeting Soluble TNFα Protects from Arthritis without Inducing Reactivation of Latent Tuberculosis." *J Immunol* 178: 7450-7457; Le Buanec, et al. "TNFα kinoid vaccination-induced neutralizing antibodies to TNFα protect mice from autologous TNFα-driven chronic and acute inflammation." *Proc Natl Acad Sci USA* 103: 19442-19447).

Based on the X-ray crystal structure of trimeric mTNFα (Baeyens, et al. (1997) "Crystallization and preliminary X-ray studies of mouse tumor necrosis factor." *Acta Crystallogr D Biol Crystallogr* 53: 329-330; Baeyens, et al. (1999) "The structure of mouse tumour-necrosis factor at 1.4 A resolution: towards modulation of its selectivity and trimerization." *Acta Crystallogr D Biol Crystallogr* 55: 772-778) a single Tyr$^{86}$→pNO$_2$Phe mutant mTNFα (pNO$_2$Phe$^{86}$ mTNFα) was selected as an immunogen for our initial studies (FIG. 1B). Tyr$^{86}$ is highly conserved among different mammalian TNFs, and it has been determined that mutations at this site have no effect on protein folding and trimer formation, but lead to a significant loss in cytotoxicity (Van Ostade, et al. (1994) "Structure-activity studies of human tumour necrosis factors." *Protein Engineering* 7: 5-22; Loetscher, et al. (1993) "Human tumor necrosis factor alpha (TNF alpha) mutants with exclusive specificity for the 55-kDa or 75-kDa TNF receptors." *J Biol Chem* 268: 26350-7; Zhang, et al. (1992) "Site-directed mutational analysis of human tumor necrosis factor-alpha receptor binding site and structure-functional relationship." *J Biol Chem* 267: 24069-75) (which is advantageous for vaccination purposes).

In this example, the unnatural amino acid p-nitrophenylalanine (pNO$_2$Phe) was genetically introduced into murine tumor necrosis factor-α (mTNFα) to replace residue Tyr$^{86}$. Mice immunized with this pNO$_2$Phe containing protein were found to generate a strongly neutralizing antibody response that effectively cross-reacted with wild-type mTNFα. Furthermore, this immunization was found to efficiently protect mice against a lipopolysaccharide (LPS) induced lethality. These results show that a self-protein, which bears a unique NO$_2$ group, a highly immunogenic moiety not found in naturally occurring proteins, will be recognized as a foreign antigen by the immune system. Due to the close structure similarity of the protein comprising the unique NO$_2$ group and the native protein, the antibodies elicited against the modified protein cross-reacted with the corresponding self-protein. This approach thus provides a general method for breaking immune tolerance of self-proteins and the production of vaccines.

In the experiments, *E. coli* XL1-Blue and BL21(DE3) were used as hosts for cloning and expression, respectively. The vector pET26b was obtained from Novagen (Madison, Wis., USA). Unless described otherwise, *E. coli* strains were grown in minimal medium containing 1% glycerol and 0.3 mM leucine (GMML medium) or 2×YT medium. Restriction enzymes, T4 DNA ligase, dNTPs, and factor Xa protease were obtained from NEB (Beverly, Mass., USA). IPTG and 4-12% Bis-Tris Gels for sodium dodecylsulfate polyacrylamide gel electrophoresis (SDS-PAGE) were purchased from Invitrogen (Carlsbad, Calif., USA). pNO$_2$-Phe was purchased from Advanced ChemTech (Louisville, Ky., USA). Primers were purchased from Integrated DNA Technologies (Coralville, Iowa, USA). DNA polymerase was obtained from Stratagene (La Jolla, Calif., USA). The anti-TNFα antibody was from R&D system (Minneapolis, Minn., USA) and recombinant mTNFα was obtained from BioSource (Camarillo, Calif., USA). Plasmid DNA was isolated using QIAGEN Plasmid Purification Kits and DNA purification after restriction digestion was performed using QIAquick PCR or gel purification kit (QIAGEN, Valencia, Calif., USA).

Construction of an mTNFα Expression Vector

To express mTNFα in *E. coli*, plasmid pET26-mTNFα was constructed that consists of an N-terminal His$_6$ tag, a factor Xa cleavage site and the mTNFα gene behind the T7-lac promoter, was used. The plasmid was constructed as follows: The murine tnfα gene was amplified from plasmid pMuT-NFα (ATCC # 63169) using polymerase chain reaction (PCR) with the following primers: 5'-ATATACATATGCT-CAGATCATCTTCTCA AAATTCG (SEQ ID NO: 1) and 5'-AACAACCTCGAGTTATCACAGAGCAAT-GACTCCAAAGT AGACC (SEQ ID NO: 2). The resulting PCR product was digested with NdeI and XhoI restriction enzymes and ligated into a pET26b vector (Novagen). The recombinant vector was then modified to append an N-terminal hexahistidine-tag (His$_6$-tag) followed by a proteolysis site for factor Xa immediately prior to the first codon for mature WT mTNFα. Site specific incorporation of pNO$_2$Phe into mTNFα mutant was carried out by mutating the codon for Tyr$^{86}$, Lys$^{11}$, or Asp$^{42}$ with a TAG amber codon in plasmid pET26-mTNFα, and these substitutions were generated using the Quick Change Mutagenesis Kit (Stratagene). The same kit was also used to prepare the mTNFα mutants Ala$^{86}$ mTNFα, Phe$^{86}$ mTNFα and Phe$^{42}$ mTNFα. The sequences of all mTNFα constructs were confirmed by DNA sequence analysis performed by the Genomics Institute of the Novartis Research Foundation (San Diego, CA, USA).

Expression of pNO2Phe$^{86}$ mTNFα in *Escherichia coli*

The pNO$_2$Phe$^{86}$ mTNFα, pNO$_2$Phe$^{11}$ mTNFα, and pNO$_2$Phe$^{42}$ mTNFα mutants were then expressed in the presence of an orthogonal, amber suppressor tRNA$_{CUA}$/aminoacyl-tRNA synthetase pair derived from *M. jannaschii* that specifically inserts pNO$_2$Phe (structure shown in FIG. 1A) into proteins in *E. coli* in response to amber codon (Tsao, et al., (2006) "The genetic incorporation of a distance probe into proteins in *Escherichia coli*." *J Am Chem Soc* 128:4572-4573). The mutant protein (~1 mg/L in GMML minimum medium) was purified by Ni$^{2+}$ affinity chromatography either under denaturing or native conditions, followed by cleavage of the His$_6$ tag and size-exclusion chromatography. To express the pNO$_2$Phe$^{86}$ mTNFα, pNO$_2$Phe$^{11}$ mTNFα, and pNO$_2$Phe$^{42}$ mTNFα mutants, *E. coli* BL21(DE3) cells were co-transformed with mutNO$_2$PheRS, mutRNA$_{CUA}$ and the respective mutant mTNFα gene. The transformed cells were grown in the presence of 1 mM pNO$_2$Phe in GMML medium at 37° C. and induced with 1 mM IPTG when OD$_{600\,nm}$ reached 0.5. The cells were then continually shaken at 37° C. for 12-16 h and then harvested. The cell pellet was stored at −80° C. until use. WT mTNFα, Phe$^{86}$ mTNFα, and Phe$^{42}$ mTNFα were expressed by essentially the same procedure. However, in contrast to the pNO$_2$Phe mTNFα mutants, these proteins were expressed in rich medium (2×YT medium) in the absence of pNO$_2$Phe.

Purification of WT mTNFα and pNO$_2$Phe$^{86}$ mTNFα under Denaturing Conditions All purification steps were performed at room temperature. After thawing the cell pellet for 15 minutes on ice, the cell paste was resuspended in lysis buffer (100 mM NaH$_2$PO$_4$, pH=8.0, 10 mM Tris/HCl, 8M urea) at 5 ml per gram of wet weight. The cell suspension was sonicated on ice for 3 minutes. After centrifugation at 10,000×g for 25 minutes, 10 ml of Ni-NTA His-Bind Resin (Novagen, Madison, Wis., USA) was added to the supernatant and mixed on a rotary shaker for 60 minutes.

The lysate-resin mixture was loaded into a 5 ml polypropylene column (QIAGEN) and washed twice with 40 ml of wash buffer A (100 mM NaH$_2$PO$_4$, pH=6.3, mM Tris/HCl, 8M urea). After another two washing steps with 10 ml of wash buffer B (100 mM NaH$_2$PO$_4$, pH=5.9, 10 mM Tris/HCl, 8M urea), elution was carried out with 100 mM NaH$_2$PO$_4$, pH=4.5, 10 mM Tris/HCl, 8M urea. The protein mixture was concentrated with a 10 K molecular weight cut-off Amicon Ultra-15 centrifugal filter device (Millipore, Bedford, Mass., USA) and loaded onto a HiPrep™26/10 desalting column (GE Healthcare, Piscataway, N.J., USA) pre-equilibrated with factor Xa cleavage buffer (20 mM Tris/HCl; 200 mM NaCl; 1 mM EDTA, pH=7.4). Turbid fractions containing inclusion bodies were concentrated by several rounds of diafiltration using a 10 K molecular weight cut-off Amicon Ultra-15 centrifugal filter device prior to addition of factor Xa (5% w/w).

Quantitative removal of the N-terminal His$_6$-tag was achieved within ~3 days at room temperature as verified by SDS-PAGE analysis. After protease digestion, soluble factor Xa protease and the His$_6$-tag peptide were separated from the inclusion bodies by centrifugation. The protein was then dissolved in ~1 ml solubilization buffer (8M urea, 50 mM Tris/HCl, pH=8.0, 10 mM DTT) and injected onto a Superdex 75 10/300 GL column (GE Healthcare) pre-equilibrated with solubilization buffer. Two rounds of size-exclusion chromatography were carried out on an ÄKTA purifier instrument (GE Healthcare) at a flow rate of 0.3 ml/minute. For refolding, the protein sample was dialyzed against renaturation buffer (240 mM NaCl; 10 mM KCl; 0.5% Triton X-100; 50 mM Tris/HCl; 1 mM EDTA, pH=8.0) using a 10 K molecular weight cut-off Slide-A-Lyzer dialysis cassette (Pierce, Rockford, Ill., USA). The refolded pNO$_2$Phe$^{86}$ mTNFα was dialyzed against phosphate-buffered saline (PBS).

Purification of WT and Mutant mTNFα under Native Conditions

All purification steps under native conditions were performed at 4° C. After thawing the cell pellet for 15 min on ice, the cell paste was resuspended in lysis buffer (50 mM Tris/HCl, pH=8.0; 150 mM NaCl, 10% (v/v) glycerol) at 5 ml per gram wet weight. After addition of Complete Protease Inhibitor Cocktail (Roche, Indianapolis, Ind., USA), 10 mL of cell suspension was treated with 150 μL of lysozyme (100 mg/mL; MP Biomedicals, Irvine, Calif., USA), 50 μL of DNase I (5 mg/mL; Roche), 5 μL of RNase A (100 mg/mL; Sigma-Aldrich, St. Louis, Mo., USA), and 125 U benzonase nuclease (Novagen). The cell suspension was stirred at room temperature for 20 min to allow lysis to occur. The prelysed cells were then flash-frozen in liquid nitrogen and thawed in a 37° C. water bath. This freeze-thaw cycle was repeated once. Complete lysis was then achieved by sonication on ice for 2 min.

After centrifugation at 18,000×g for 20 min, 1 ml of Ni-NTA His-Bind Resin (Novagen) was added to the supernatant and mixed on a rotary shaker for 30 min. The lysate-resin mixture was loaded onto a 5 ml polypropylene column (QIAGEN) and washed twice with 20 ml of lysis buffer. Protein was eluted with 2 mL of elution buffer (50 mM Tris/HCl, pH 8.0; 150 mM NaCl, 250 mM imidazole, 10% (v/v) glycerol), concentrated with a 10 K molecular weight cut-off Amicon Ultra-15 centrifugal filter device (Millipore), and further purified by a Superdex 75 10/300 GL column (flow rate of 0.3 ml/min) pre-equilibrated with PBS. All proteins were characterized by MALDI-TOF mass spectrometry, which was performed on a Voyager-DE-STR instrument (Applied Biosystems, Foster City, Calif., USA) with sinapinic acid as a matrix at the Scripps Center for Mass Spectrometry, The Scripps Research Institute (La Jolla, Calif., USA). All mTNFα proteins purified under native conditions were completely soluble at >10 mg/mL in PBS buffer (pH=7.5) at 25° C.

Analyzing the Composition and Homogeneity of pNO$_2$Phe$^{86}$ mTNFα

Figure 1D:
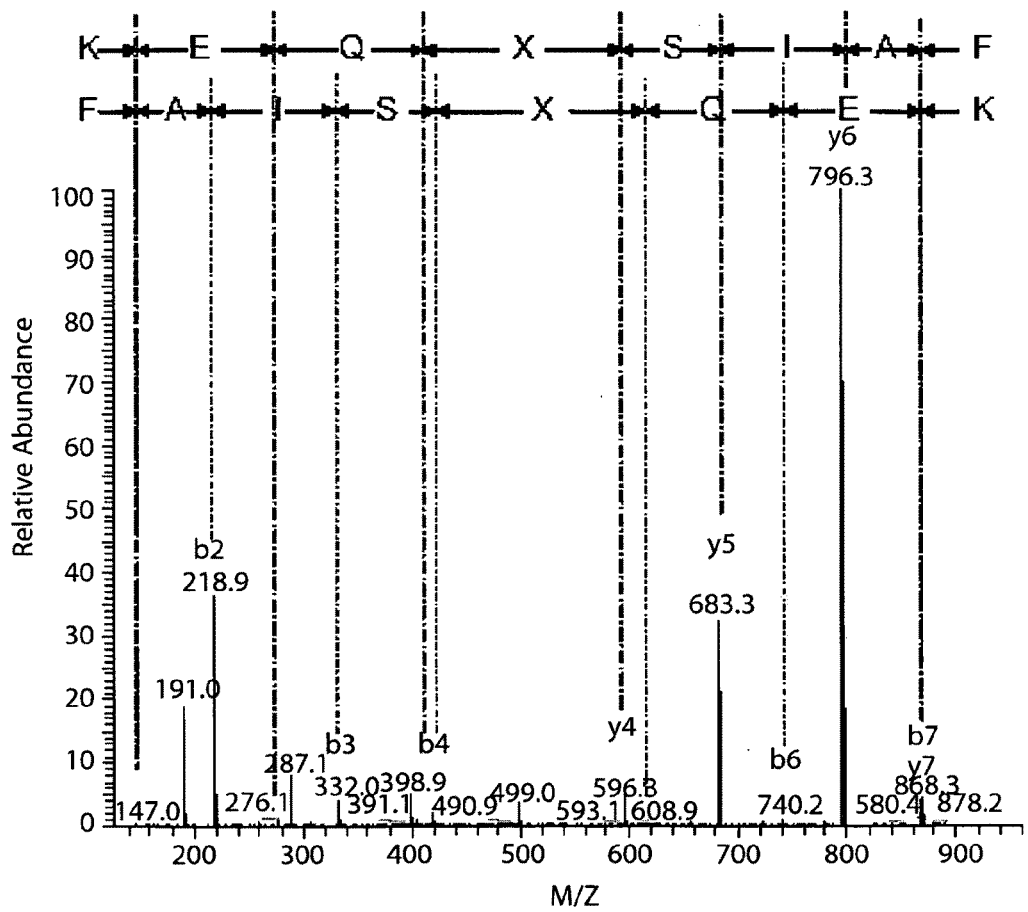

The composition and homogeneity of the mutant protein was subsequently analyzed by SDS-PAGE (FIG. 1C) and mass spectrometry (FIG. 1D). Shown in FIG. 1C is the expression of the Tyr$^{86}$ amber mutant of mTNFα in the absence (lane 2) and presence (lane 3) of 1 mM pNO$_2$Phe with the pNO$_2$Phe specific mutRNACUA/aminoacyl-tRNA synthetase pair. Protein samples were purified by Ni-NTA affinity column and analyzed by SDS-PAGE with SimplyBlue™ staining. Lane 4 represents wild-type mTNFα and lane 1 is a molecular mass standard. The results depicted in FIG. 1C show that the pNO$_2$Phe$^{86}$ mTNFα purified under denaturing conditions has a similar mobility on SDS-PAGE as WT mTNFα; no full-length mTNFα was observed when the mutant gene was expressed in the absence of pNO$_2$Phe, indicating that there is no detectable incorporation of endogenous amino acids at position 86.

Figure 12:
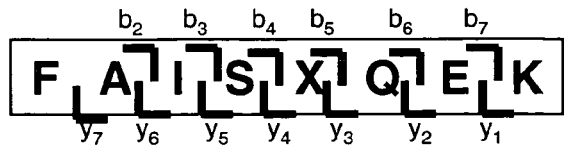
FIG. 12 depicts the results of MS/MS sequencing of a tryptic fragment of $pNO_2Phe^{86}$-mTNFα.

The composition of homogeneity of the mutant protein was also analyzed by MS/MS sequencing analysis of its tryptic fragments (FIG. 1D). To prepare the protein sample for this procedure, an excised gel slice containing pNO$_2$Phe$^{86}$ mTNFα was diced into small pieces and mixed with 100 μL of 25 mM NH$_4$HCO$_3$/50% acetonitrile. After vortexing for 10 minutes, the supernatant was discarded. This step was repeated twice, and the gel pieces were then dried in a Speed Vac for approximately 20 minutes. The protein sample was reduced by addition of 25 μl of 10 mM DTT in 25 mM NH$_4$HCO$_3$. The reaction was allowed to proceed at 56° C. for 1 hour. After removal of the supernatant, the gel pieces were nixed with 25 μl of 55 mM iodoacetamide. After incubation in the dark for 45 minutes at room temperature, the gel pieces were subjected to tryptic in-gel digestion as described in a published procedure (Rosenfeld, et al., (1992) "In-gel digestion of proteins for internal sequence analysis after one- or two-dimensional gel electrophoresis." *Anal Biochem* 203: 173-179; Hellman, et al., (1995) "Improvement of an 'In-Gel' digestion procedure for the micropreparation of internal protein fragments for amino acid sequencing." *Anal Biochem* 224:451-455). The resultant peptide mixture was purified with C18 ZipTip (Millipore) and subjected to MS/MS fragmentation on a Thermo Finnigan LTQ mass spectrometer (Thermo Scientific, Somerset, N.J., USA), which was run in positive ion mode using the nanospray source at the Scripps Center for Mass Spectrometry, The Scripps Research Institute (La Jolla, Calif., USA). The MS/MS analysis of an 8-mer tryptic fragment, prepared as described above, exactly matches the pattern for the incorporation of pNO$_2$Phe at residue 86 (FIG. 1D, FIG. 12). The partial sequence of the octomer fragment FAISXQEK, where X denotes pNO$_2$Phe, can be read from the annotated b or y ion series in FIG. 1D. In FIG. 12, the sequence of the tryptic fragment containing pNO$_2$-Phe is shown in single letter code (X, pNO$_2$-Phe). Observed fragment ions of the y and b series are indicated. Key y and b ions proving the incorporation of pNO$_2$-Phe are represented in red. All masses are reported as monoisotopic masses.

All proteins were characterized by MALDI-TOF mass spectrometry (FIGS. 2, 3, and Table 1), which was performed on a Voyager-DE-STR instrument (Applied Biosystems, Foster City, Calif., USA) with sinapinic acid as a matrix at the Scripps Center for Mass Spectrometry, The Scripps Research Institute (La Jolla, Calif., USA). The MALDI-TOF spectrum (Table 1, FIG. 2) also shows a peak ([M-H]+:17287) that matches the expected molecular weight of pNO$_2$Phe containing full-length mTNFα ([M-H]+: 17286). These results demonstrate the selective incorporation of pNO$_2$Phe into the mutant mTNFα.

TABLE 1

MALDI-TOF mass spectroscopy analysis of mTNFα variants.

| compound | species | observed mass (calculated mass) (Da) full-length protein without His$_6$ tag | protein without Leu$^1$Arg$^2$ |
|---|---|---|---|
| pNO$_2$Phe$^{86}$ mTNFα | [M + H]+ | 17287 (17286) | 17038 (17017) |
| mTNFα WT | [M + H]+ | 17255 (17257) | 16987 (16988) |
| mTNFα Phe$^{86}$ | [M + H]+ | 17237 (17241) | 16972 (16972) |
| mTNFα Ala$^{86}$ | [M + H]+ | 17162 (17165) | 16895 (16896) |

Analyzing the Tertiary Structure of pNO$_2$Phe$^{86}$ mTNFα

To determine the effect of the pNO$_2$Phe mutations on the tertiary/quaternary structure of pNO$_2$Phe$^{86}$ mTNFα, Phe$^{86}$ mTNFα, pNO$_2$Phe$^{42}$ mTNFα, Phe$^{42}$ mTNFα, and pNO$_2$Phe$^{11}$ mTNFα both WT mTNFα and mutant mTNFα samples were analyzed by fast protein liquid chromatography (Table 2). The X-ray crystal structure of mTNFα trimer with Tyr-86, Asp42m, and Lys-11 inducted (PDB ID code 2TNF) is shown in FIG. 1B). All protein samples were analyzed by fast protein liquid chromatography (FLPC) with a Superdex 75 10/300 GL gel filtration column (GE Healthcare). Size-exclusion chromatography was performed in PBS buffer at 25° C. using a flow rate of 0.3 ml/minute. Both WT mTNFα and pNO$_2$Phe$^{86}$ mTNFα were completely soluble at >10 mg/ml in PBS buffer (pH=7.5) at 25° C. The column was calibrated with a molecular weight gel-filtration standard from Bio-Rad (Bio-Rad Labs, Hercules, Calif., USA) containing thyroglobulin (670 kDa), gamma globulin (158 kDa), ovalbumin (44.0 kDa), myoglobin (17.0 kDa), and vitamin B-12 (1.35 kDa). Protein elution was followed by measuring the absorption of eluted fractions at 280 nm.

Figure 4:
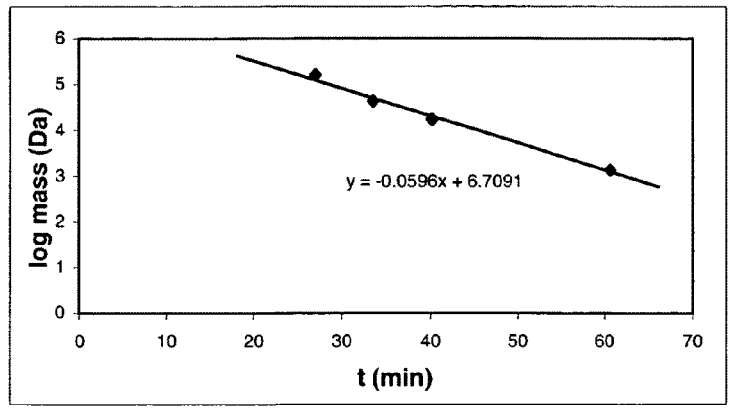
FIG. 4 depicts the results of FPLC experiments performed to determine the effects of $Tyr^{86}pNO_2Phe$ substitution on the tertiary structure of a mutant mTNFα protein.

Both WT mTNFα and pNO$_2$Phe$^{86}$ mTNFα showed a similar retention time that corresponded to a molecular weight matching their trimeric forms. A plot of the logarithm of the molecular mass of the protein standards versus the retention time on a Superdex 75 10/300 GL gel filtration column is shown in FIG. 4. Thyroglobulin (670 kDa) was omitted for calculation, because its molecular weight was far outside the separation range of the Superdex 75 10/300 GL column (3 kDa-70 kDa). Based on the plot shown in FIG. 4, the molecular masses of the quaternary structures pNO$_2$Phe$^{86}$ mTNFα, WT mTNFα, mTNFα F$^{86}$, pNO$_2$Phe$^{42}$ mTNFα, mTNFα F$^{42}$, and pNO$_2$Phe$^{11}$ mTNFα were determined, and are shown in Table 2 (below). Monomeric pNO$_2$Phe$^{86}$ mTNFα would have eluted at a retention time of 41.47 minutes.

TABLE 2

Observed and Calculated Molecular Masses of WT mTNFα and mTNFα mutants

| Sample | Retention time (min) | Observed mass (calculated mass of trimer) (kDa) |
|---|---|---|
| pNO$_2$Phe$^{86}$ mTNFα without His$_6$ tag | 33.00 | 55.2 (51.9) |
| Phe$^{86}$ mTNFα without His$_6$ tag | 33.20 | 53.8 (51.7) |
| pNO$_2$Phe$^{42}$ mTNFα with His$_6$ tag | 32.64 | 58.0 (57.7) |
| Phe$^{42}$ mTNFα with His$_6$ tag | 32.01 | 63.3 (57.6) |
| WT mTNFα without His$_6$ tag | 32.97 | 55.5 (51.8) |
| pNO$_2$Phe$^{11}$ mTNFα with His6 tag | 32.55 | 58.8 (57.6) |

The quaternary structures of pNO$_2$Phe$^{86}$TNFα, Phe$^{86}$ mTNFα, pNO$_2$Phe$^{42}$ mTNFα, Phe$^{42}$ mTNFα, pNO$_2$Phe$^{11}$ mTNFα, and WT mTNFα were determined based on a plot of the logarithm of the molecular mass of the protein standards versus the retention time on a Superdex 75 10/300 GL gel filtration column.

Analysis of the Biological Activity of pNO$_2$Phe$^{86}$ mTNFα

Figure 5:
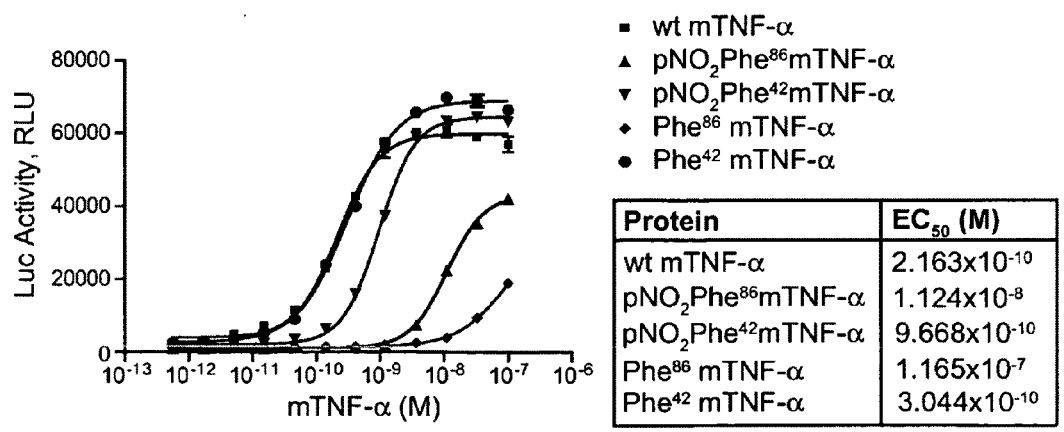
FIG. 5 depicts the analysis NFκB-Luc activity of various mTNFα mutants.

The biological activities of the proteins were assayed by measuring the mTNFα-induced activation of NFκB pathway in a NFκB-luciferase reporter cell line. HEK293 cells stably expressing NFκB-Luc were used in the reporter gene assay (Ye, et al., (2000) "ER Stress Induces Cleavage of Membrane-Bound ATF6 by the Same Proteases that Process SREBPs" *Mol Cell* 6:1355-1364). The stable cells were dissociated with trypsin, resuspended in DMEM containing 10% FBS at 5×10$^5$ cells/ml, and plated at 20 µl/well in 384-well white plate (Greiner, Longwood, Fla.). After 2 hours incubation at 5% CO$_2$ in a 37° C. tissue culture incubator, 20 µl of TNFα was added to the cells. The cells were continuously incubated for 24 hours. Luciferase activities were measured by addition of 20 µl Bright-Glo (Promega, Madison, Wis.), and the plate was read using a luminescence plate reader. The results of the assay indicated that, WT mTNFα activated NFκB signaling in a NFκB-luciferase reporter cell line. In contrast, the pNO$_2$Phe$^{86}$ mutant (FIG. 5) had only 2% of the activity of WT mTNFα in the assay, consistent with previous reports that Tyr$^{86}$ is essential for receptor binding and that a variety of mutations at residue 86 lead to a significant loss in activity (Van Ostade, et al., (1994) "Structure-activity studies of human tumour necrosis factors" *Protein Engineering* 7:5-22; Loetscher, et al., (1993) "Human tumor necrosis factor alpha (TNF alpha) mutants with exclusive specificity for the 55-kDa or 75-kDa TNF receptors" *J Biol Chem* 268:26350-7; Zhang, et al., (1992) "Site-directed mutational analysis of human tumor necrosis factor-alpha receptor binding site and structure-functional relationship" *J Biol Chem* 267:24069-75). One additional peak was also found in the MALDI-TOF spectrum which corresponded to the deletion of first two amino acids of pNO$_2$Phe$^{86}$ mTNFα (Table 1, FIG. 2), presumably due to over-digestion during factor Xa proteolytic cleavage step. Because it was difficult to separate this truncated protein from full-length protein, and because the deletion of the first two N-terminal amino acids only slightly affected TNF activity (Van Ostade, et al., (1994) "Structure-activity studies of human tumour necrosis factors" *Protein*

Engineering 7:5-22), the mixture was used directly to immunize mice both for the mutant mTNFα and WT control.

Figure 13:
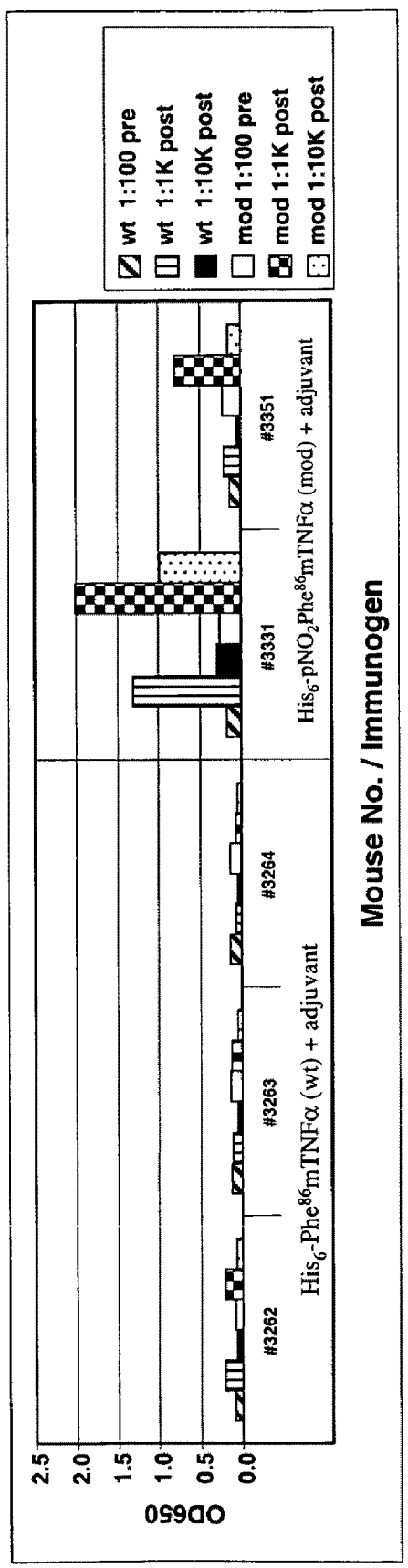
FIG. 13 depicts the results of experiments that were performed to show that the presence of an N-terminal $His_6$ tag on $His_6$-$Phe^{86}$ mTNFα (WT) or $His_6$-$pNO_2Phe^{86}$ mTNFα had no influence on the results of subsequent immunization experiments.

Additional experiments were performed to show that the presence or absence of an N-terminal $His_6$ tag had no influence on the immunization results (FIG. 13). Five Bcl2 mice, e.g., #3262, #3263, #3264, #3331, #3351, were randomized into two groups and injected with $His_6$-$Phe^{86}$ mTNFα (WT) or $His_6$-$pNO_2Phe^{86}$ mTNFα, respectively, using the RIMMS (repetitive immunization at multiple sites) protocol (described below). Briefly, the mice were injected 8 times over 18 days. In each injection, 5 μg of protein in 200 μl PBS was mixed 1:1 with complete Freund's adjuvant (CFA) for the first injection, or with incomplete Freund's adjuvant (IFA) for the remaining injections at 6 specific sites proximal to peripheral lymph nodes. On day 21, antibody titers against $pNO_2Phe^{86}$ mTNFα and $Phe^{86}$ mTNFα were determined by enzyme-linked immunosorbent assay (ELISA) using a horseradish peroxidase conjugate of goat anti-mouse IgG secondary antibody. See FIG. 13. In the figure, before immunization, the mouse serum was diluted 100 fold (1:100 pre) and after immunization the mouse serum was diluted either 1,000 fold (1:1 K post) or 10,000 fold (1:10 K post) and subjected to ELISA. The ELISA plate was coated either with WT mTNFα (WT, first three bars) or $pNO_2Phe^{86}$ mTNFα (mod, last three bars).

Figure 6:
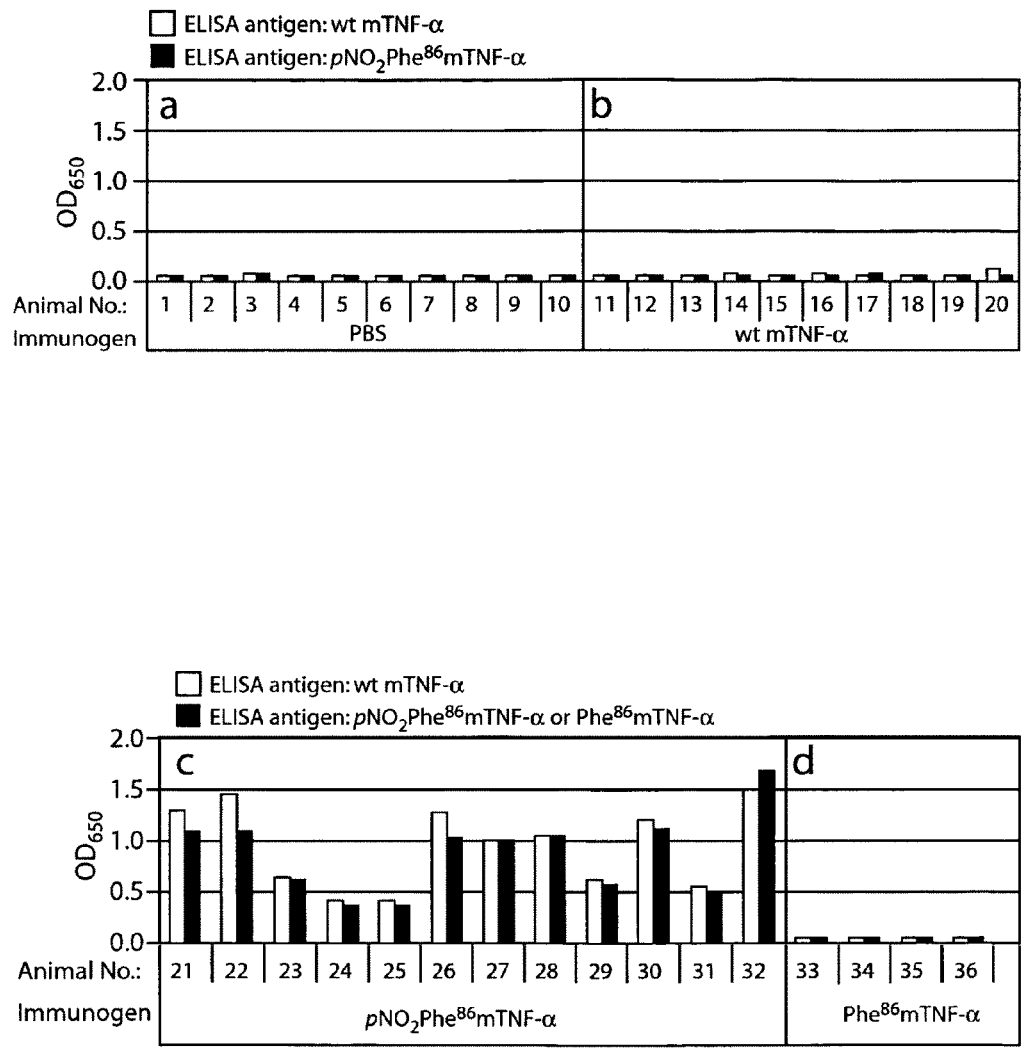
FIG. 6 depicts serum titers for C57BL/6 mice immunized with (a) PBS, (b) WT-mTNFα, (c) $pNO_2Phe^{86}$ mTNFα or (d) $Phe^{86}$ mTNFα.
Figure 7:
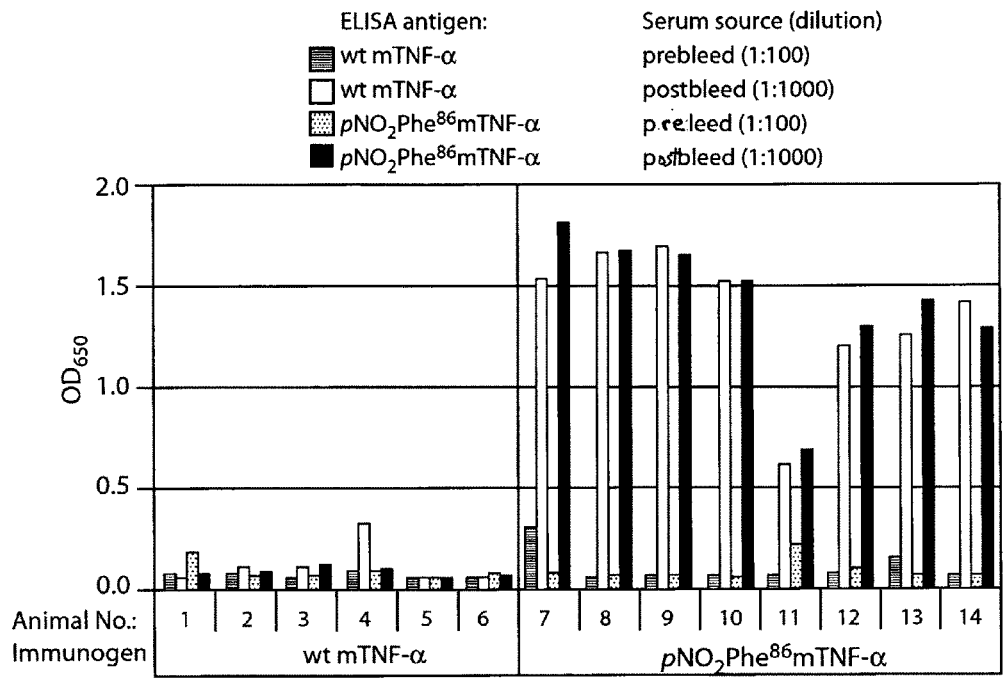
FIG. 7 depicts serum titers against wt mTNFα and $pNO_2Phe^{86}$ mTNFα for Bcl2 mice immunized with wt mTNFα or $pNO_2Phe^{86}$ mTNFα.
Figure 8:
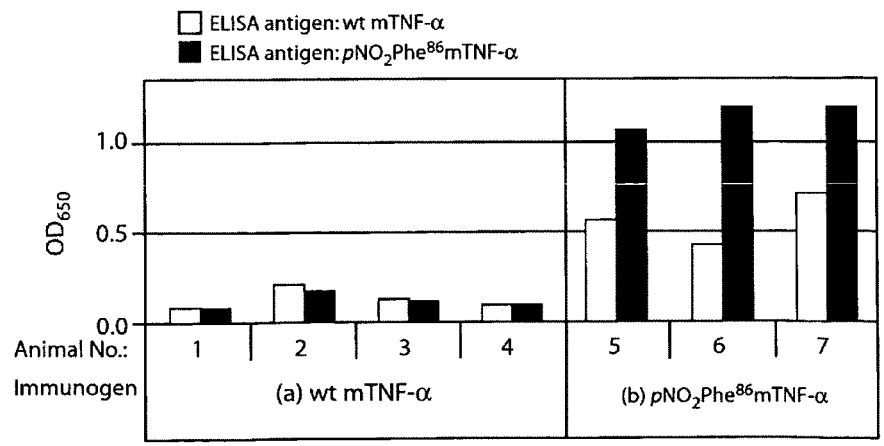
FIG. 8 depicts the results of ELISAs against wt mTNFα or $pNO_2Phe^{86}$ mTNFα performed to determine serum titers for Bcl-2 mice immunized with wt mTNFα, or $pNO_2Phe^{86}$ mTNFα in the absence of adjuvant.
Figure 9:
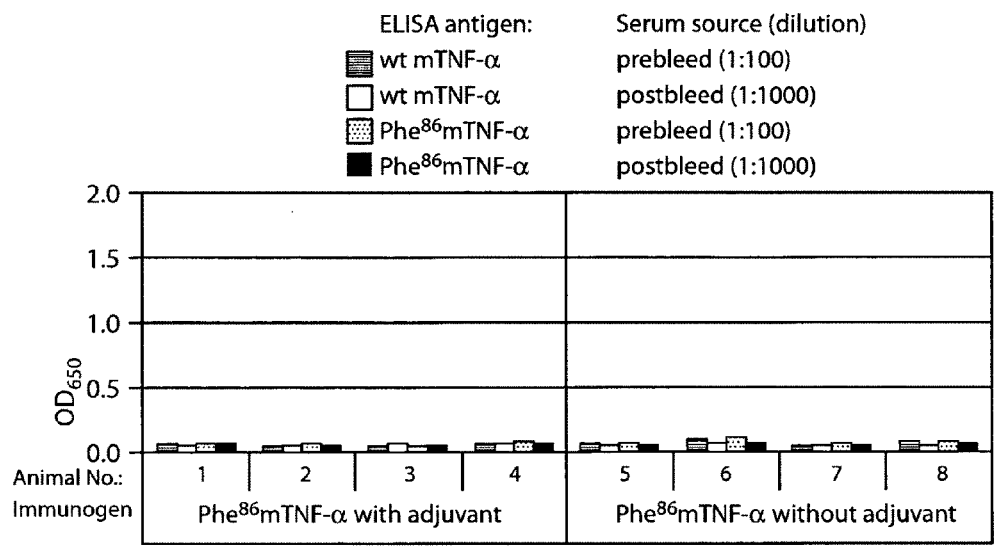
FIG. 9 depicts serum titers against wt mTNFα and $Phe^{86}$ mTNFα for Bcl2 mice immunized with $Phe^{86}$ mTNFα in the absence or presence of adjuvant.
Figure 10:
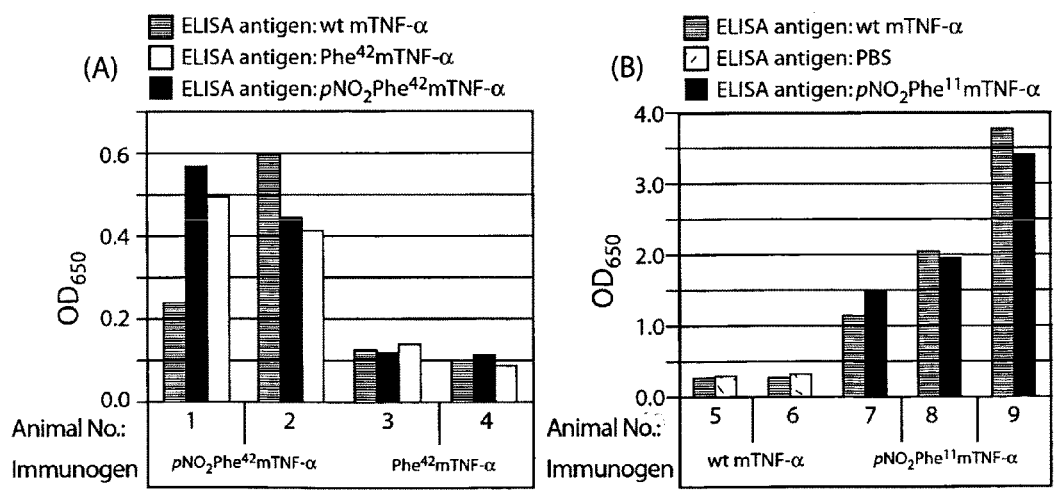
FIG. 10A depicts serum titers against wt mTNFα, $pNO_2Phe^{11}$ mTNFα, and $Phe^{42}$ mTNFα for C57BL/6 mice immunized with either $pNO_2Phe^{42}$ mTNFα or $Phe^{42}$ mTNFα.
FIG. 10B depicts serum titer against WTmTNFα, PBS, and $pNO_2Phe^{11}$ mTNFα, for C57BL/6 mice immunized with either $pNO_2Phe^{11}$mTNFα or $Phe^{42}$ mTNFα.

Analyzing Serum Titer Against $pNO_2Phe^{86}$ mTNFα or WT mTNFα in Mice Immunized with $pNO_2Phe^{86}$ mTNFα mTNFα knockout mice are viable and show no apparent phenotypic abnormalities (Pasparakis, et al. (1996) "Immune and inflammatory responses in TNF alpha-deficient mice: a critical requirement for TNF alpha in the formation of primary B cell follicles, follicular dendritic cell networks and germinal centers, and in the maturation of the humoral immune response." *J Exp Med* 184: 1397-1411), suggesting that mice will survive a neutralizing immune response against TNFα, allowing vaccinated mice to be analyzed for anti-TNFα antibody production and biological activity. To determine the immunogenicity of the $pNO_2Phe^{86}$ mTNFα mutant, thirty-two C57BL/6 mice were divided into three groups and injected with $pNO_2Phe^{86}$ mTNFα, WT mTNFα, and PBS buffer, respectively, following the RIMMS (repetitive immunization at multiple sites) protocol (Kilpatrick, et al., (1997) "Rapid development of affinity matured monoclonal antibodies using RIMMS" *Hybridoma* 16:381-389). To avoid adverse effects due to cytotoxicity of mTNFα, a dose of 5 μg of mTNFα per injection was used throughout this study (Libert, et al., (1999) "Identification of a locus on distal mouse chromosome 12 that controls resistance to tumor necrosis factor-induced lethal shock" *Genomics* 55:284-289). FIG. 6 shows the serum titers for C57BL/6 mice immunized with PBS (6A); WT mTNFα (6B); $pNO_2Phe^{86}$ mTNFα (6C); or $Phe^{86}$ mTNFα (6D). Briefly, mice were injected 8 times over 17 days. In each injection, 5 μg of protein in 200 μl of PBS was mixed 1:1 with complete Freund's Adjuvant (CFA) for the first injection or with incomplete Freund's Adjuvant (IFA) for the remaining injections at 6 specific sites proximal to peripheral lymph nodes. On day 21, antibody titers against $pNO_2Phe^{86}$ mTNFα and WT mTNFα were determined by enzyme-linked immunosorbent assay (ELISA) using a horseradish peroxidase conjugate of goat anti-mouse IgG secondary antibody.

To perform the ELISA, Maxisorp 384-well plates (Nunc, Rochester, N.Y.) were coated with 30 μl of 0.5 μg/ml protein overnight at 4° C. The coated plates were washed with PBS+0.05% Tween 20 (PBST), blocked with 80 μl of 1% BSA in PBS, and washed again with PBST. The plates were sequentially incubated with 20 μl of primary antibody or serum diluted in 1% BSA in PBS, 20 μl of HRP-conjugated goat anti-mouse IgG (Jackson ImmunoResearch Laboratories, West Grove, Pa.), and 20 μl of TMB substrate (KPL, Gaithersburg, Md.), and read at an absorbance of 650 nm. The plates were washed with PBST between incubations.

ELISAs were measured against WT mTNFα (FIGS. 6A and 6B, left bars) or $pNO_2Phe^{86}$ mTNFα (FIGS. 6A and 6B, right bars). For mice immunized with $Phe^{86}$ mTNFα, ELISAs were measured against WT mTNFα (FIGS. 6C and 6D, left bars) or $Phe^{86}$ mTNFα (FIGS. 6C and 6D, right bars). Before measurement, serum samples were diluted 1/1000 with 1% BSA in PBS buffer. Mice immunized with either WT mTNFα or PBS buffer alone had insignificant serum IgG titers against both $pNO_2Phe^{86}$ mTNFα and WT mTNFα (FIG. 6). This is expected since WT mTNFα is a self-protein and should be tolerated by the murine immune system. In contrast, mice immunized with $pNO_2Phe^{86}$ mTNFα were found to display markedly high serum titers for both $pNO_2Phe^{86}$ mTNFα (FIG. 6C, right bars in each pair of bars) as well as WT mTNFα (FIG. 6C, left bars in each pair of bars). Thus, a single $pNO_2Phe$ mutation (which altered the monomer molecular weight by 29 Daltons) induced a strong immunological response that resulted in antibodies that are highly cross-reactive with WT mTNFα. Similar results were obtained with Bcl-2 mice, indicating that this result was not strain dependent (FIG. 7). Again, the RIMMS protocol involved 8 injections (5 μg protein/injection) over a period of 17 days in the presence of CFA for the initial injection and IFA for the remaining 7 injections. ELISAs were measured against WT mTNFα (second and first bars in each group of four bars) or $pNO_2Phe^{86}$ mTNFα (fourth and third bars in each group of four bars). Before measurement, serum samples were diluted either 1/100 or 1/1000 with 1% BSA in PBS buffer.

We also examined the immunogenicity in the absence of strong immunopotentiators and found that immunization of Bcl-2 mice with $pNO_2Phe^{86}$ mTNFα in the absence of any adjuvant also elicited significant anti-TNFα titers (FIG. 8), suggesting that this approach can be applicable to therapeutic settings in which strong adjuvants are not desirable. Serum titers for Bcl-2 mice immunized with (a) WT mTNFα, or (b) $pNO_2Phe^{86}$ mTNFα for 8 injections (5 μg protein/injection) over a period of 17 days in the absence of either CFA or IFA. ELISAs were measured against WT mTNFα (left bar in each pair of bars) or $pNO_2Phe^{86}$ mTNFα (right bar in each pair of bars). Before measurement, serum samples were diluted 1/1000 with 1% BSA in PBS buffer.

Furthermore, the duration of the antibody response after a sequence of eight immunizations with the $pNO_2Phe^{86}$ mTNFα was found to quite robust after 19 weeks (FIG. 14). Such a long sustainability is highly desirable for clinical use, because current strategies often suffer from rapidly decreasing autoantibody titers when immunization ceases. FIG. 14 shows results of the determination of serum titer durability. To perform the experiment, three Bcl-2 transgenic mice were immunized with $pNO_2Phe^{86}$ mTNFα. After a sequence of eight immunizations, bleeds were taken for ELISA analysis against $pNO_2Phe^{86}$ mTNFα at defined time points. Before each measurement, serum samples were diluted 1:100 with 1% BSA in PBS buffer. At corresponds to the time period between the last immunization and the bleed.

To verify that the immunological response was a result of the immunogenic nitroaryl group of the unnatural amino acid, a $Tyr^{86}$ Phe mutant, mTNFα ($Phe^{86}$ mTNFα) was generated. After confirmation of its trimeric quaternary structure by size-exclusion chromatography, Bcl2 mice were immunized with this mutant either in the presence or absence of CFA/

IFA. For mice immunized without adjuvant, the RIMMS protocol involved 8 injections (5 µg protein/injection) over a period of 17 days. For mice immunized with adjuvant, CFA was used for the first injection and IFA for the remaining 7 injections. ELISAs were measured against WT mTNFα (FIG. 9, second and first bars in each group of four bars) or Phe$^{86}$ mTNFα (FIG. 9, fourth and third bars in each group of four bars). Before measurement, serum samples were diluted either 1/100 or 1/1000 with 1% BSA in PBS buffer. In both cases, e.g., presence or absence of adjuvant, no significant anti-TNFα titers were generated, indicating that the NO$_2$ group is required to break immunological tolerance (FIGS. 6D and 9). Furthermore, CD$_4^+$ T cells specific for pNO$_2$Phe$^{86}$ mTNFα were elicited only when mice were immunized with this mutant protein and not when mice were immunized with WT mTNFα or Phe$^{86}$ mTNFα (FIG. 15A). In contrast, no significant proliferation was observed when CD$_4^+$ T cells from pNO$_2$Phe$^{86}$ mTNFα-immunized Bcl-2 mice were stimulated in vitro with WT mTNFα (FIG. 15B). To perform the T-cell proliferation assays, CD4$^+$ T cells from immunized mice were isolated from lymph nodes by magnetic depletion with MACS beads (Miltenyi Biotec). T cells were then placed into culture with irradiated splenocytes from naïve Bcl-2 mice and increasing amounts of antigen. The cultures were incubated for 48 h and then pulsed with [$^3$H]thymidine overnight. The culture plates were harvested onto filter mats and radioactivity was quantified with a TopCount scintillation counter (PerkinElmer).

Preliminary epitope mapping experiments with mTNFα mutants and peptide fragments of WT mTNFα indicate that the polyclonal response to pNO$_2$Phe$^{86}$ mTNFα involves multiple protein epitopes. Together, these results suggest that insertion of pNO$_2$Phe into the sequence of mTNFα creates a T cell epitope, which enhances T cell help to trigger an effective immune response against this disease-associated self protein. Other immunization protocols (e.g., sequential immunization with the mutant and WT TNFα) can also yield high-titer cross-reactive antibodies. These results are consistent with those of Dalum, et al. (1999) "Therapeutic antibodies elicited by immunization against TNF-alpha." *Nat Biotechnol* 17: 666-669, who incorporated immunodominant T-helper cell epitopes into mTNFα to break immune tolerance. The current strategy, however, results in minor pertubations in a protein and should not disrupt its tertiary fold or dramatically affect expression, solubility, or stability.

The polypeptide sequence surrounding Tyr$^{86}$ is not predicted to be a T-cell epitope based on in silico sequence-based analysis of potential MHC class II DR epitopes in TNFα (Steed, et al. (2003) "Inactivation of TNF Signaling by Rationally Designed Dominant-Negative TNF Variants." *Science* 301: 1895-1898). Nonetheless, to begin to explore the generality of this approach, we determined whether substitution of $pNO_2Phe$ at other sites might have a similar effect. The surface exposed residue $Asp^{42}$, which is not involved in trimerization or receptor binding, was therefore mutated to $pNO_2Phe$. After confirming the mutation by SDS-PAGE and mass spectrometry, two groups of C57BL/6 mice were immunized with either $pNO_2Phe^{42}$ mTNFα or the $Phe^{42}$ mTNFα mutant (FIG. 10). The RIMMS protocol involved 8 injections (5 μg protein/injection) over a period of 17 days in the absence of adjuvant. ELISAs were measured against WT mTNFα (FIG. 10A, first bars in each group of three bars; FIG. 10B, first bars in each pair of bars), $pNO_2Phe^{42}$ mTNFα/ $pNO_2Phe^{11}$ mTNFα (FIG. 10A, second bars in each group of three bars; FIG. 10B, second bars in each pair of bars in 7, 8, and 9), or $Phe^{42}$ mTNFα (FIG. 10A, third bars in each group of bars) or PBS (FIG. 10B, second bars in each pair of bars in 5 and 6). Before measurement, serum samples were diluted 1/100 (FIG. 10A) or 1/800 (FIG. 10B) with 1% BSA in PBS buffer. Again, significant anti-TNFα titers were elicited only by immunization with $pNO_2Phe^{42}$ mTNFα immunized mice elicited significant anti-TNFα titers. This result indicated that $pNO_2Phe$ mutagenesis would be a fairly general approach to render specific self- or foreign antigens highly immunogenic.

A similar result was obtained with mutation of another surface-exposed residue, $Lys^{11}$, to $pNO_2Phe$. These results suggest that $pNO_2Phe$ mutagenesis can be a fairly general approach to render specific self- or foreign antigens highly immunogenic and may not be limited to substitutions at surface-exposed Tyr or Phe residues. However, preliminary studies indicate that incorporation of $pNO_2Phe$ is less effective at positions 104 and 19. Immunization of C57BL/6 mice with $pNO_2Phe^{114}$ mTNFα resulted in the generation of antibodies that lacked significant cross-reactivity with native mTNFα. Thus, context effects play a role in determining the nature of the immune response. Finally, it is likely that other genetically encoded immunogenic amino acids can also be beneficially used; alternatively for smaller antigens, immunogenic unnatural amino acids can be incorporated by semisynthesis or total peptide synthesis.

Analyzing the Response of $pNO_2Phe^{86}$ mTNFα Immunized Mice to LPS Challenge

We next determined whether vaccination of mice with the $pNO_2Phe^{86}$ TNFα would protect against a lipopolysaccharide (LPS) challenge in a severe endotoxemia mouse model (F. Niessen, et al. (2008) "Dendritic cell PAR-S1P3 signalling couples coagulation and inflammation." *Nature* 452: 654-658). Septic shock induced by LPS in this model was known to involve in the production and release of TNFα. All experiments to study mouse endotoxemia were carried out in accordance with the National Institutes of Health Animal Protection Guidelines and were approved by The Scripps Research Institute Animal Care and Use Committee. Lipopolysaccharide (LPS, *E. coli* O111:B4, Calbiochem/EMD Biosciences, San Diego, Calif., USA) was dissolved in 37° C. normal saline (0.9% w/v of NaCl) by vortexing for 30 seconds before and after two minutes of sonication. Male C57BL/6 mice from Jackson Laboratories (Bar Harbor, Me., USA) were injected intraperitoneally under 2% isoflurane at the age of 9 weeks with 7.5 mg/kg LPS for the passive immunizations or 15 weeks with 8.5 mg/kg LPS for the active immunization. All experiments were carried out in a room with alternating 12 h light dark cycles under stable conditions of temperature (20-22° C.) and relative humidity (40-60%). Kaplan-Meier survival plots of mice receiving active or passive immunizations are shown in FIG. 11. The Kaplan-Meier curves were plotted and survival differences were analyzed using a log rank test.

C57BL/6 mice were immunized with PBS, WT mTNFα and $pNO_2Phe^{86}$ mTNFα. These mice were subsequently injected intraperitoneally with LPS (8.5 mg/kg) three days after completion of the above immunization regime, and their survival rate was determined. In FIG. 11A, mice (8 per group) immunized with $pNO_2Phe^{86}$ mTNFα or WT mTNFα were compared with 7 mice receiving sham immunizations. Survival advantage of mice immunized with $pNO_2Phe^{86}$ mTNFα ($p<0.01$) vs. wild-type is shown. In FIG. 11B, mice (8 per group) injected with 100 μg purified IgG from $pNO_2Phe^{86}$ mTNFα or wild-type immunized mice were compared to controls receiving saline injection. Survival advantage of mice immunized with $pNO_2Phe^{86}$ mTNFα ($p<0.01$) vs. wild-type is shown. In FIG. 11C, mice (6 per group) received 100 μL of pooled serum from mice immunized with $pNO_2Phe^{86}$ mTNFα or wild-type mTNFα. Survival advantage of mice immunized with pNO$_2$Phe$^{86}$ mTNFα (p<0.01) vs. wild-type is shown. Control mice were injected with equal volumes of physiological saline.

Figure 11:
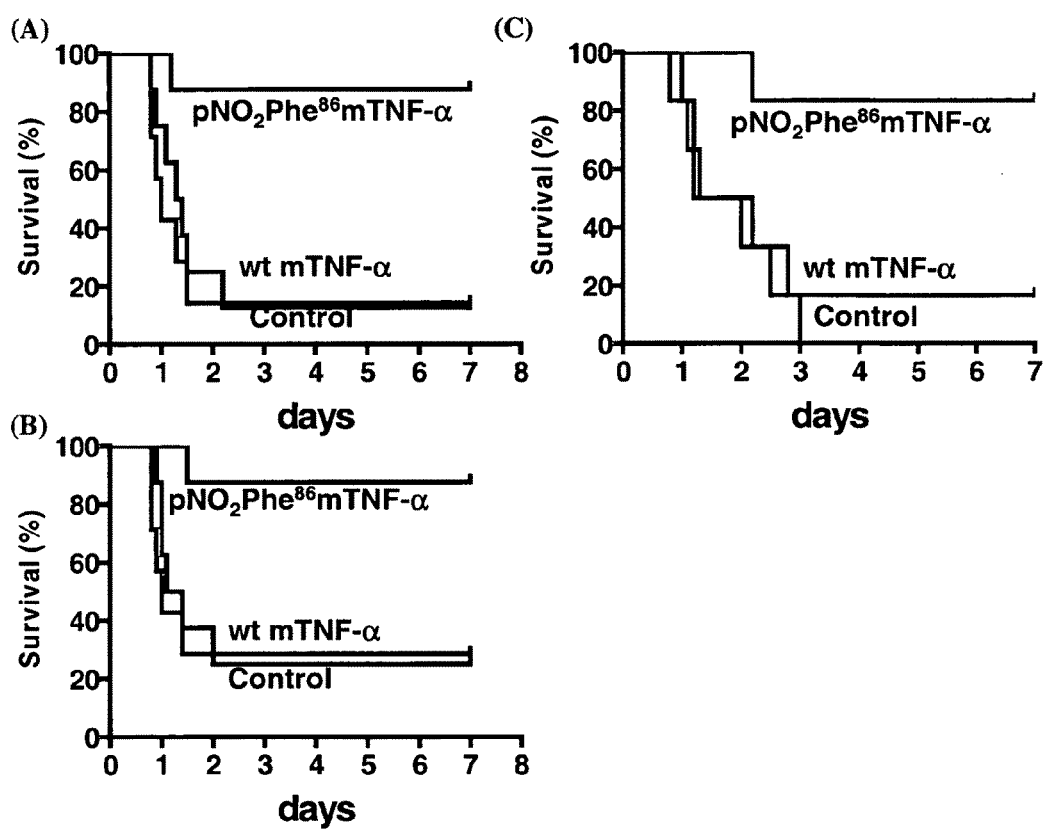
FIG. 11 depicts results from experiments performed to determine whether immunization with $pNO_2Phe^{86}$ mTNFα improves survival of mice in a TNFα-dependent severe endotoxemia model.

As depicted in FIG. 11A, mice immunized with the pNO$_2$Phe$^{86}$ mTNFα mutant showed a significantly greater survival advantage (87.5%) than those that received PBS and WT mTNFα (12.5% survival rate) immunizations. Similarly, C57BL/6 mice receiving either pooled serum (100 uL) or purified IgG antibody (4 mg/kg) collected from Bcl-2 mice pre-immunized with pNO$_2$Phe$^{86}$ mTNFα showed a significantly higher survival rate (83.3-87.5%) than those receiving pooled serum or IgG from Bcl-2 mice immunized with WT mTNFα (16.7-25.0%) (FIGS. 11B, 11C). Hence, these results demonstrate that a single NO$_2$Phe mutant of a self-protein induces a robust cross-reactive antibody response against native protein that is protective in a disease model. We are currently extending these studies to other TNFα dependent models including collagen-induced arthritis (CIA) model and KRN transgenic mouse (K/BxN) model (Ditzel (2004) "The K/BxN mouse: A model of human inflammatory arthritis." Trends Mol Med 10: 40-45).

The IgG antibody used in the injections described above was prepared by loading murine serum onto a 10 ml sepharose-conjugated protein G affinity column (GammaBind Plus Sepharose, Pharmacia Biotech, Piscataway, N.J., USA). The column was washed with three column volumes of PBS (pH 7=4). Elution was carried out with two column volumes of 0.1M acetic acid (pH 3=0). The eluate was then neutralized with 1M Tris/HCl (pH=9.0) and dialyzed into PBS (pH=7.4).

Mice were passively immunized 24 hours prior to the endotoxin challenge. In the first experiment, mice received an intraperitoneal injection of 100 μL of pooled serum from mice immunized with either pNO$_2$Phe$^{86}$ mTNFα or WT mTNFα. A second cohort received 4 mg/kg of IgG purified from serum of mice immunized with either pNO$_2$Phe$^{86}$ mTNFα or WT mTNFα. Control mice were injected with equal volumes of physiological saline.

The above findings demonstrate that a single mutation of Tyr$^{86}$ to pNO$_2$Phe (the only difference with WT-protein was substitution of an —OH with an —NO$_2$ group at a solvent exposed site) dramatically enhanced the immunogenicity of the protein and led to a neutralizing antibody response in a TNFα dependent mouse model. Mutagenesis of residues 86 and close proximal residue 85 to Ala had little effect on the antibody titers to either the pNO$_2$Phe$^{86}$ or WT protein, indicating that the antibodies recognized a discontinuous epitope. The results indicate that a protein bearing a unique NO$_2$ group, a highly immunogenic moiety not found in natural occurring proteins, will be recognized as a foreign antigen by the immune system. Due to the close structure similarity, the elicited antibodies cross-reacted with the corresponding self-protein thereby breaking immunological tolerance.

This example shows that it is possible to break immunological self-tolerance, e.g., for vaccine production, by the site-specific incorporation of pNO$_2$Phe into a protein epitope, e.g., in target self-proteins. Although it has been known for some time that altered proteins can induce autologous antibodies, the ill-defined nature of the changes that render the proteins immunogenic complicate their production and therapeutic utility (Lerner, et al. (1968) "The induction of acute glomerulonephritis in rabbits with soluble antigens isolated from normal homologous and autologous urine" J Immunol 100: 1277-1287). For example, the arsanil-sulfanil-thryoglobulin preparations used in the studies of Weigle contained ~50 azo linkages per molecule of thyroglobulin (Weigle (1965) "The production of thyroiditis and antibody following injection of unaltered thyroglobulin without adjuvant into rabbits previously stimulated with altered thyroglobulin" J Exp Med 122:1049-1062), resulting in a highly heterogeneous and possibly aggregated or partially unfolded antigen. Similarly, insertion of T-cell epitopes at various positions in antigens can create proteins with altered tertiary structure, solubility, and stability compared with native protein. In contrast, the changes made here are chemically defined and confined to single residues. Moreover, these mutations do not appear to affect the overall quaternary structure of the protein nor its solubility. The resulting antibodies are therefore more likely to recognize the corresponding epitopes in the native protein. Finally, pNO$_2$Phe-containing TNFα mutants induced a protective cross-reactive immune response without the need for strong adjuvants and resulted in high titers for at least 4 months, attributes that may facilitate therapeutic applications of this methodology.

This strategy can be applicable to other self-proteins, including those associated with protein folding diseases (e.g., amyloid-beta1-42 peptide) or cancer. In addition, by introducing the pNO$_2$Phe group at weakly immunogenic or otherwise silent epitopes, this approach may also permit the generation of a strong antibody response against regions of a pathogen that are predicted to result in neutralizing antibodies against viral, bacterial or parasite infections (e.g., the CS1 protein of malaria or the E410 epitope of HIV-1 gp41). Furthermore, the selective introduction of immunogenic amino acids into proteins can facilitate the generation of functional antibodies, e.g., agonists or antagonists, of G protein-coupled receptors and other membrane-bound receptors for which it has historically been difficult to generate strong antibody responses. The structural bases for this phenomenon and exploration of its application to human disease are currently being elucidated.

Explanation of Results Depicted in Figures of Example 1

FIG. 1 shows the results of experiments that were performed to confirm the in corporation of pNO$_2$Phe into mTNFα. FIG. 1A shows the structure of the unnatural amino acid pNO$_2$Phe. FIG. 1B provides an X-ray crystal structure of mTNFα trimer with Tyr-86, Asp-42, and Lys-11 indicated (PDB ID code 2TNF). FIG. 1C shows the results of experiments that were performed to confirm, that the expression of the Tyr$^{86}$ amber mutant of mTNFα occurs in the presence (lane 3), but not in the absence (lane 2) of 1 mM pNO$_2$Phe with the pNO$_2$Phe-specific mutRNA$_{CUA}$/aminoacyl-tRNA synthetase pair. Protein samples in FIG. 1C were purified by Ni-NTA affinity column under denaturing conditions and analyzed by SDS/PAGE with SimplyBlue staining. Lane 4 contains WT mTNFα, and lane 1 is a molecular mass standard. The pNO$_2$Phe$^{86}$ mTNFα mutant is characterized in FIG. 1D. A tandem mass spectrum of the octamer fragment FAISXQEK is provided, where X denotes pNO$_2$Phe. The octamer fragment was produced from trypsin digestion of pNO$_2$Phe$^{86}$ mTNFα. The partial sequence of the octamer containing pNO$_2$Phe can be read from the annotated b or y ion series.

Figure 2:
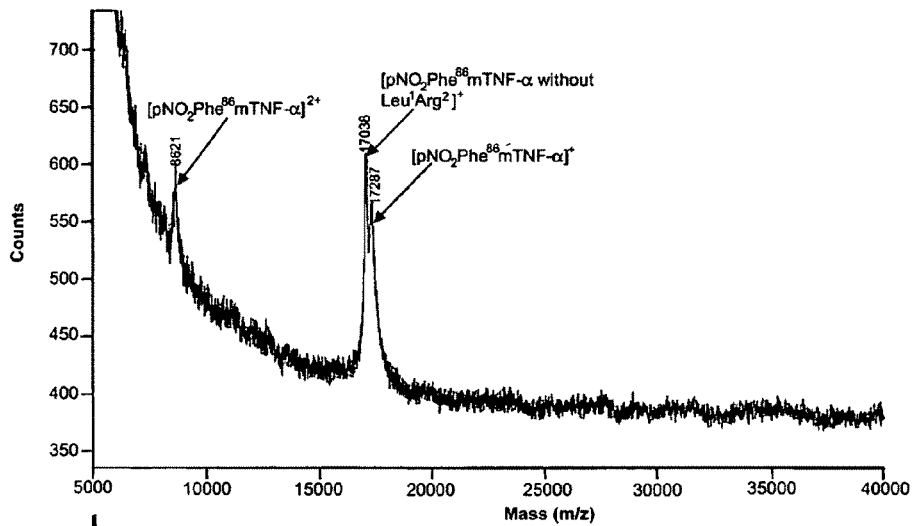
FIG. 2 depicts the results of MALDI-TOF mass spectrometric analysis of $pNO_2Phe^{86}$-mTNFα.
Figure 3:
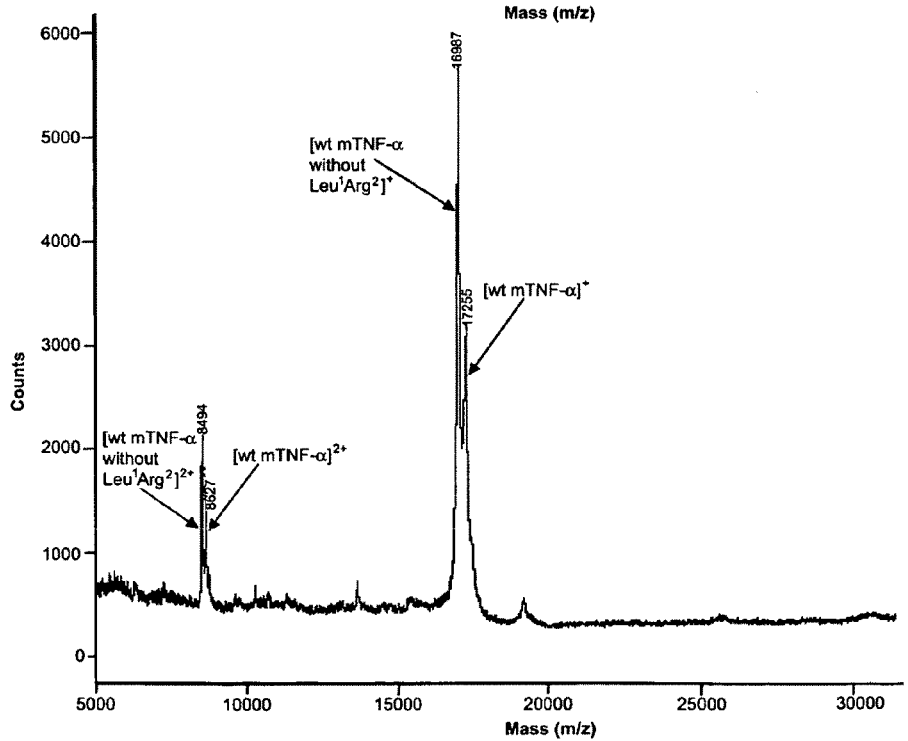
FIG. 3 depicts the results of MALDI-TOF mass spectrometric analysis of wt-mTNFα.

Several experiments were performed to confirm the incorporation of pNO$_2$Phe into mTNFα and to show that the incorporation of pNO$_2$Phe did not affect the quaternary structure of the unnatural TNFα. FIG. 2 provides the results of a MALDI-TOF mass spectrometric analysis of pNO$_2$Phe$^{86}$ mTNFα, and FIG. 3 provides the results of a MALDI-TOF mass spectrometric analysis of WT mTNFα. The peaks in FIG. 2 confirm that the mass of the unnatural TNFα indicate that a pNO$_2$Phe residue was incorporated. FIG. 4 depicts the results of FPLC experiments performed to determine the effects of Tyr$^{86}$→pNO$_2$Phe substitution on the tertiary structure of a mutant mTNFα protein. The mutant eluted at a time that indicates that the mutant trimerizes.

Activity assess were also performed on the mutant TNFα. FIG. 5 shows the results of NF-κB-luciferase activity analysis of WT mTNFα (squares), $pNO_2Phe^{86}$ mTNFα (triangles), $pNO_2Phe^{42}$ mTNFα (inverted triangles), $Phe^{86}$ mTNFα (diamonds), and $Phe^{42}$ mTNFα (circles). The unnatural TNFα's activity is reduced compared to WT TNFα.

Serum titers for C57BL/6 mice immunized with PBS are shown in FIG. 6A; serum titers for mice immunized with WT mTNFα are shown in FIG. 6B; serum titers for mice immunized with $pNO_2Phe^{86}$ mTNFα are shown in FIG. 6C; and serum titers mice immunized with $Phe^{86}$ mTNFα are shown in FIG. 6D. Mice immunized with either WT mTNFα or PBS buffer alone had insignificant serum IgG titers against both $pNO_2Phe^{86}$ mTNFα and WT mTNFα. This is expected since WT mTNFα is a self-protein and should be tolerated by the murine immune system. In contrast, mice immunized with $pNO_2Phe^{86}$ mTNFα were found to display markedly high serum titers for both $pNO_2Phe^{86}$ mTNFα.

The protocol involved eight injections (5 μg of protein per injection) over a period of 17 days in the presence of complete Freund's adjuvant (CFA) for the initial injection and incomplete Freund's adjuvant (IFA) for the remainder. ELISAs were measured against WT mTNFα (left bars in each pair of bars 1-32) $pNO_2Phe^{86}$ mTNFα (right bars in each pair of bars 1-32). For mice immunized with $Phe^{86}$ mTNFα (FIG. 6D), ELISAs were measured against WT mTNFα (left bars in each pair of bars 33-36) or $Phe^{86}$ mTNFα (right bars in each pair of bars 33-36). Before measurement, serum samples were diluted 1:1,000 with 1% BSA in PBS buffer.

Similar results were as those above were obtained with Bcl-2 mice, indicating that this result was not strain dependent. FIG. 7 shows serum titer levels against WT mTNFα and $pNO_2Phe^{86}$ mTNFα for Bcl2 mice immunized WT mTNFα or $pNO_2Phe^{86}$ mTNFα. The RIMMS protocol involved eight injections (5 μg of protein per injection) over a period of 17 days in the presence of CFA for the initial injection and IFA for the remaining seven injections. ELISAs were measured against WT mTNFα (second and first bars in each group of four bars) or $pNO_2Phe^{86}$ mTNFα (fourth and third bars in each group of four bars). Before measurement, serum samples were diluted either 1:100 or 1:1,000 with 1% BSA in PBS buffer.

FIG. 8 shows the results of serum titer measurements for mice that were immunized with $pNO_2Phe^{86}$ mTNFα in the absence of adjuvant. This immunization also elicited significant anti-TNFα titers, suggesting that this approach can be applicable to therapeutic settings in which strong adjuvants are not desirable. Serum titers for Bcl-2 mice immunized with WT mTNFα are shown in FIG. 8A, and titers for mice immunized with $pNO_2Phe^{86}$ mTNFα are shown in FIG. 8B. The immunizations were performed as follows: eight injections (5 μg of protein per injection) were done over a period of 17 days in the absence of either CFA or IFA. ELISAs were measured against WT mTNFα (left bars in each pair of bars) or $pNO_2Phe^{86}$ mTNFα (right bars in each pair of bars). Before measurement, serum samples were diluted 1:1,000 with 1% BSA in PBS buffer.

To verify that the immunological response was a result of the immunogenic nitroaryl group of the unnatural amino acid, a $Tyr^{86}$→Phe mutant, mTNFα ($Phe^{86}$ mTNFα) was generated, and Bcl2 mice were immunized with this mutant either in the presence or absence of CFA/IFA. FIG. 9 provides serum titer measurements against WT mTNFα and $Phe^{86}$ mTNFα for Bcl2 mice immunized with $Phe^{86}$ mTNFα in the absence or presence of adjuvant. In both cases, e.g., presence or absence of adjuvant, no significant anti-TNFα titers were generated, indicating that the $NO_2$ group is required to break immunological tolerance.

For mice immunized without adjuvant, the RIMMS protocol involved eight injections (5 μg of protein per injection) over a period of 17 days. For mice immunized with adjuvant, CFA was used for the first injection and IFA for the remaining seven injections. ELISAs were measured against WT mTNFα (second and first bars in each group of four bars) or $Phe^{86}$ mTNFα (fourth and third bars in each group of four bars). Before measurement, serum samples were diluted either 1:100 or 1:1,000 with 1% BSA in PBS buffer.

FIG. 10 shows the results of experiments that were performed to determine the immunogenicity of other surface sites on TNFα. In FIG. 10A, serum titers against WT mTNFα, $pNO_2Phe^{21}$ mTNFα, and $Phe^{42}$ mTNFα for C57BL/6 mice immunized with either $pNO_2Phe^{42}$ mTNFα or $Phe^{42}$ mTNFα are shown. In FIG. 10B, serum titers against WT mTNFα, PBS, and $pNO_2Phe^{11}$ mTNFα for C57BL/6 mice immunized with either $pNO_2Phe^{11}$ mTNFα or WT mTNFα are shown. Significant anti-TNFα titers were elicited only by immunization with $pNO_2Phe^{42}$ mTNFα immunized mice elicited significant anti-TNFα titers. This result indicated that $pNO_2Phe$ mutagenesis would be a fairly general approach to render specific self- or foreign antigens highly immunogenic The RIMMS protocol in the experiment involved eight injections (5 μg of protein per injection) over a period of 17 days in the absence of adjuvant. ELISAs were measured against WT mTNFα (first bars in each group of three bars in 10A; left bars in each pair of bars in 10B), $pNO_2Phe^{42}$ mTNFα/$pNO_2Phe^{11}$ mTNFα (second bars in each group of three bars in 10A; right bars in each pair of bars 7, 8, and 9 in 10B), $Phe^{42}$ mTNFα (third bars in each group of three bars in 10A), or PBS (right bars in each pair of bars 5 and 6 in 10B). Before measurement, serum samples were diluted 1/100 (for 10A) or 1/800 (for 10B) with 1% BSA in PBS buffer.

Septic shock induced by LPS in this model was known to involve in the production and release of TNFα. Thus, it was next determined whether vaccination of mice with the $pNO_2Phe^{86}$ TNFα would protect against a lipopolysaccharide (LPS) challenge in a severe endotoxemia mouse model (F. Niessen, et al. (2008) "Dendritic cell PAR-S1P3 signalling couples coagulation and inflammation." *Nature* 452: 654-658). FIG. 11 shows the results of experiments that were performed to determine whether immunization with $pNO_2Phe^{86}$ mTNFα improves survival of mice in a TNFα-dependent severe endotoxemia model. Kaplan-Meier survival plots of mice receiving active or passive immunizations are shown. In FIG. 11A, mice (eight per group) immunized with $pNO_2Phe^{86}$ mTNFα or WT mTNFα are compared with seven mice receiving sham immunizations. Survival advantage of mice immunized with $pNO_2Phe^{86}$ mTNFα ($P<0.01$) vs. WT is shown. In FIG. 11B, mice (eight per group) injected with 100 μg of purified IgG from $pNO_2Phe^{86}$ mTNFα or WT immunized mice were compared with controls receiving saline injection. Survival advantage of mice immunized with $pNO_2Phe^{86}$ mTNFα ($P<0.01$) vs. WT is shown. In FIG. 11C, Mice (six per group) received 100 μl of pooled serum from mice immunized with $pNO_2Phe^{86}$ mTNFα or WT mTNFα. Survival advantage of mice immunized with $pNO_2Phe^{86}$ mTNFα ($P<0.01$) vs. WT is shown.

FIG. 12 provides the results of MS/MS analysis of an 8-mer tryptic fragment derived from $pNO_2Phe^{86}$ mTNFα. The sequence of the tryptic fragment containing $pNO_2Phe$ is shown in single letter code (X=$pNO_2Phe$). Observed fragment ions of the y and b series are indicated. Key y and b ions proving the incorporation of pNO$_2$Phe are b$_5$, b$_6$, b$_7$, y$_7$, y$_6$, y$_5$, and y$_4$. All masses are reported as monoisotopic masses. The MS/MS analysis exactly matches the pattern for the incorporation of pNO$_2$Phe at residue 86.

FIG. 13 depicts the results of experiments that were performed to show that the presence of an N-terminal His$_6$ tag on His$_6$-Phe$^{86}$ mTNFα (WT) or His$_6$-pNO$_2$Phe$^{86}$ mTNFα had no influence on the results of subsequent immunization experiments.

Figure 14:
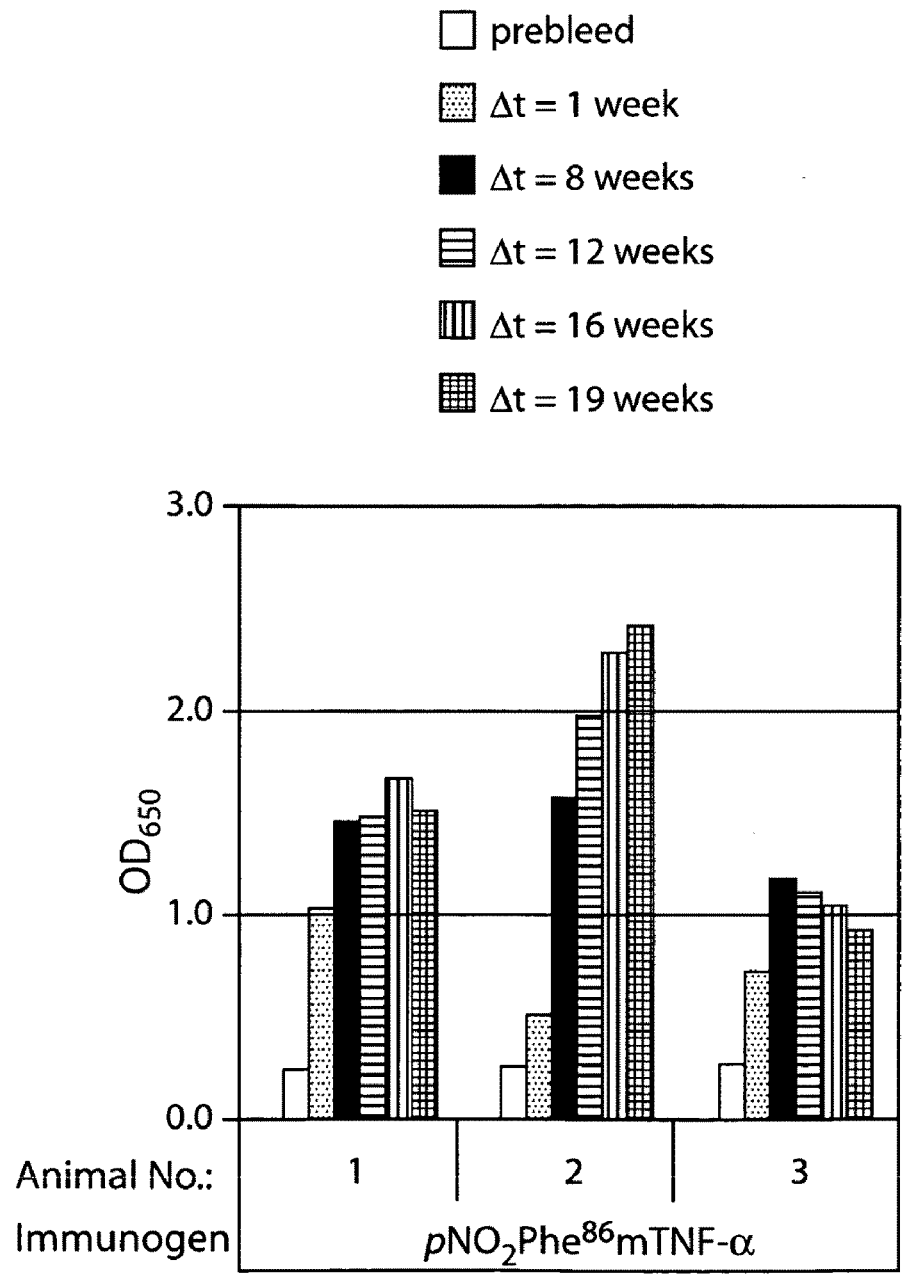
FIG. 14 depicts the results of experiments performed to determine serum titer durability.

Long sustainability of serum antibody titers is highly desirable for clinical use, because current strategies often suffer from rapidly decreasing autoantibody titers when immunization ceases. FIG. 14 shows the results of experiments performed to determine serum titer durability of the immune response against TNFα. Three Bcl-2 transgenic mice were immunized with pNO$_2$Phe$^{86}$ mTNFα. After a sequence of eight immunizations, bleeds were taken for ELISA analysis against pNO$_2$Phe$^{86}$ mTNFα at defined time points. Before each measurement, serum samples were diluted 1:100 with 1% BSA in PBS buffer. At corresponds to the time period between the last immunization and the bleed. The first bar in each group of 6 bars is prebleed, the second bar is Δt=1 week, the third bar is Δt=8 weeks, the fourth bar is Δt=12 weeks, the fifth bar is Δt=16 weeks, and the sixth bar is Δt=19 weeks.

Figure 15:
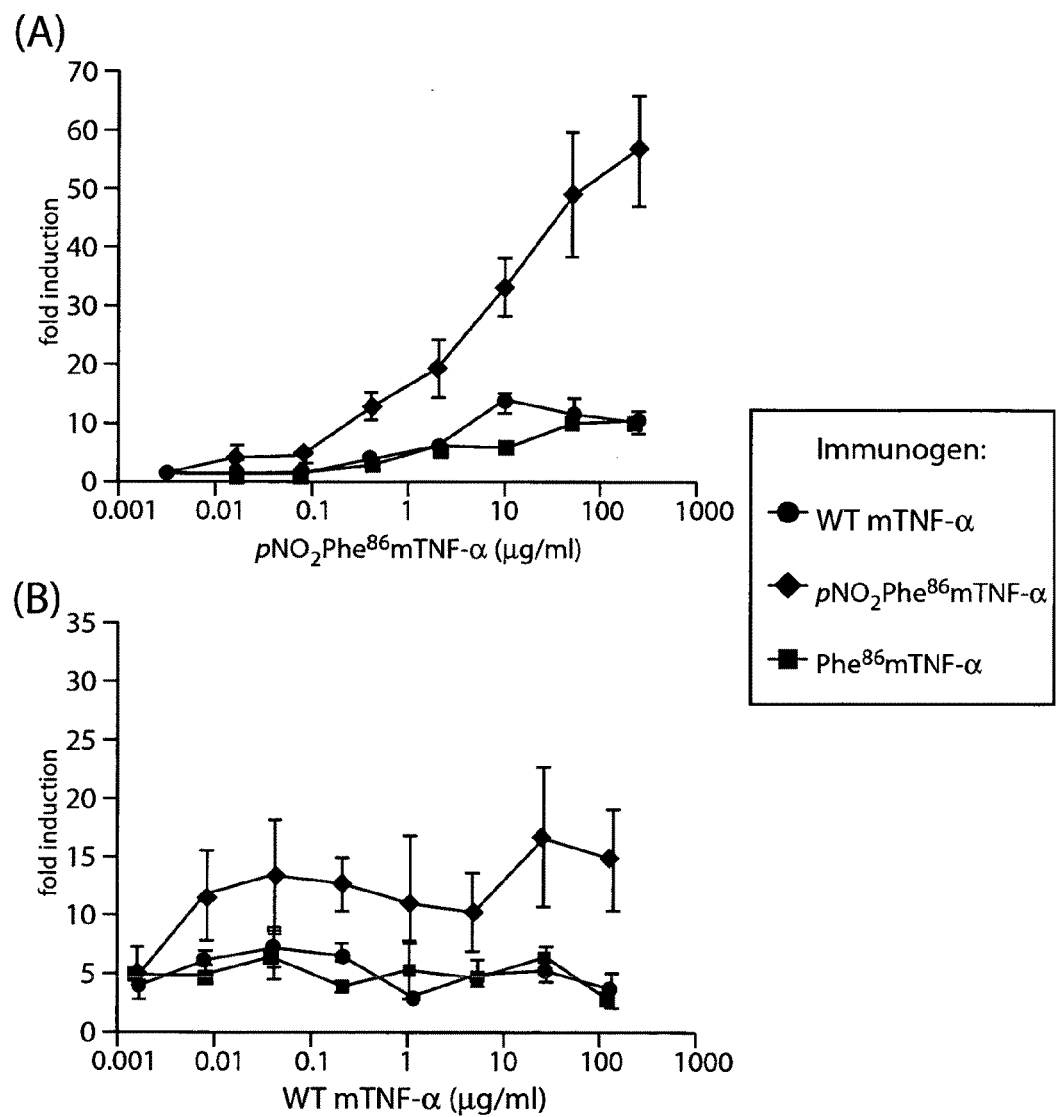
FIG. 15 depicts the results of T cell proliferative assays.

FIG. 15 shows the results of T cell proliferative assays. In FIG. 15A, proliferation of CD4$^+$ T cells from Bcl-2 transgenic mice immunized with WT mTNFα, pNO$_2$Phe$^{86}$ mTNFα, and Phe$^{86}$ mTNFα and stimulated in vitro with serial dilutions of pNO$_2$Phe$^{86}$ mTNFα is shown. In FIG. 15B, proliferation of CD4$^+$ T cells from Bcl-2 transgenic mice immunized with WT mTNFα, pNO$_2$Phe$^{86}$ mTNFα, and Phe$^{86}$ mTNFα and stimulated in vitro with serial dilutions of WT mTNFα is shown. CD$_4^+$T cells specific for pNO$_2$Phe$^{86}$ mTNFα were elicited only when mice were immunized with this mutant protein and not when mice were immunized with WT mTNFα or Phe$^{86}$ mTNFα. In contrast, no significant proliferation was observed when CD$_4^+$T cells from pNO$_2$Phe$^{86}$ mTNFα-immunized Bcl-2 mice were stimulated in vitro with WT mTNFα.

Example 2

Figure 17A:
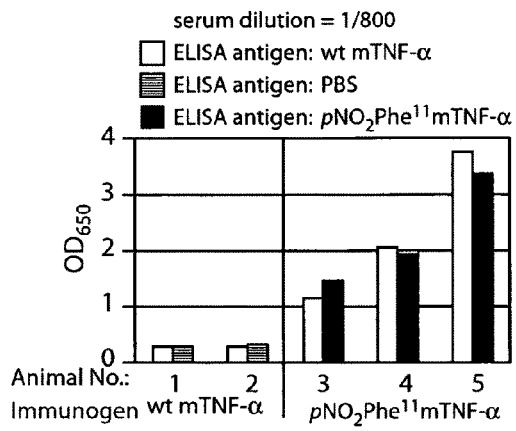
FIG. 17 shows that the four surface-exposed sites on mTNFα exhibit significant immunogenicity.
Figure 17B:
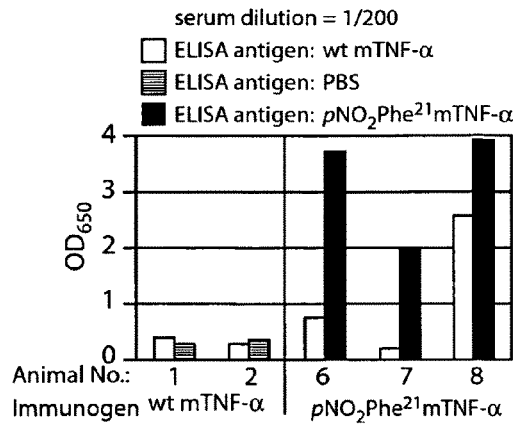
Figure 17C:
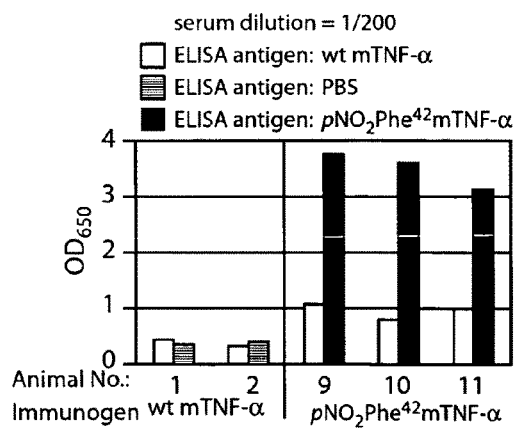
Figure 17D:
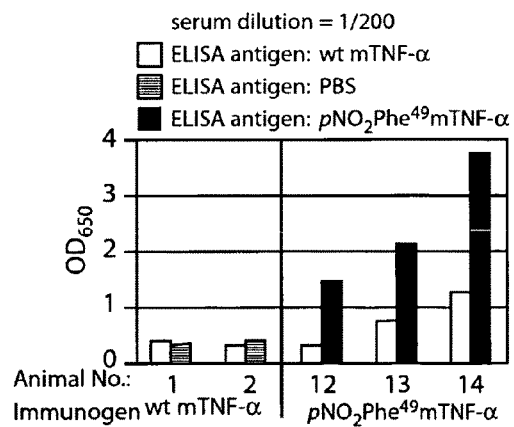
Figure 18:
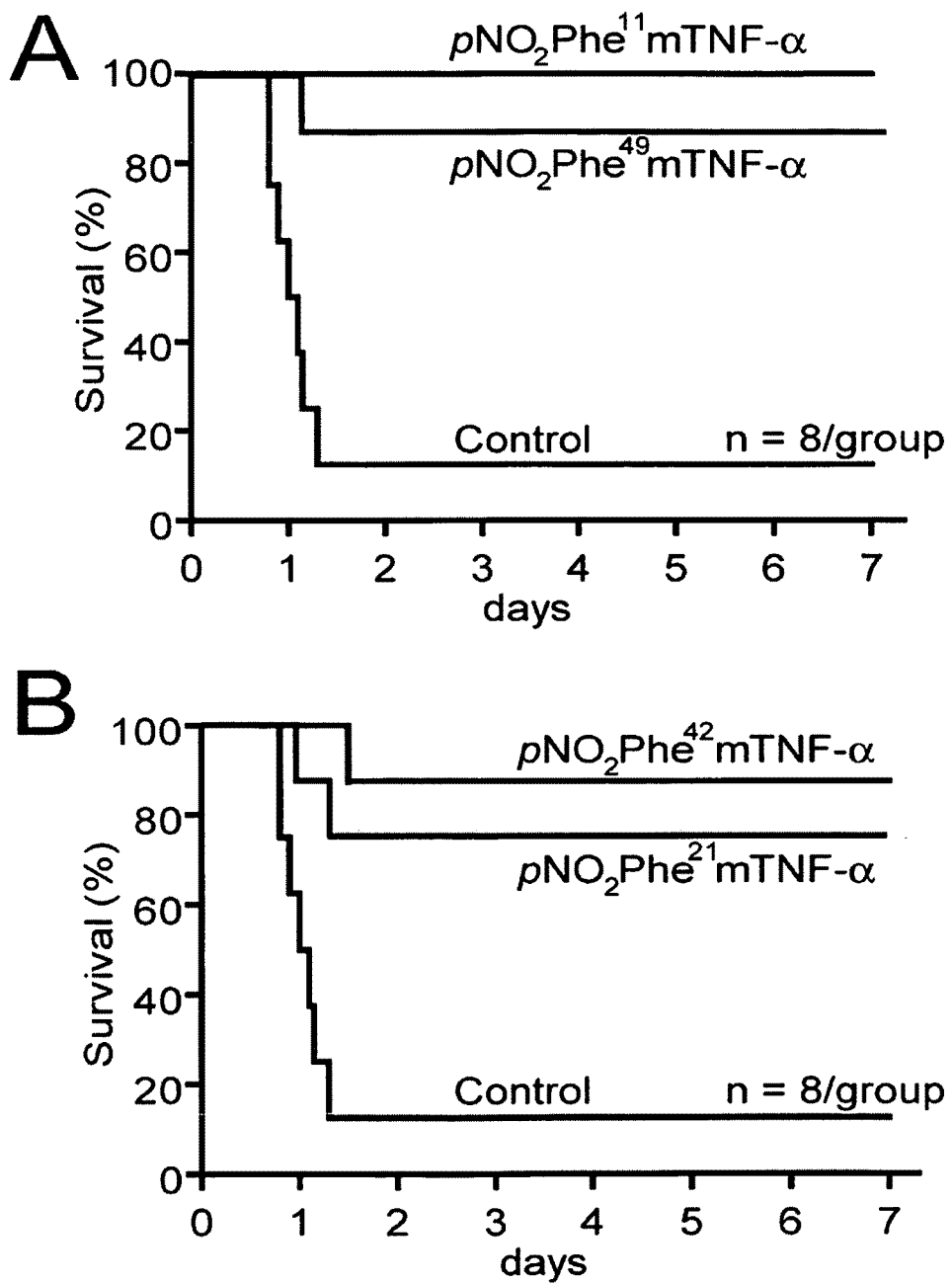
FIG. 18 shows that there is a significant survival benefit for mice immunized with various $pNO_2Phe$ mTNFα mutants after lipopolysaccharide (LPS) challenge.

Mechanistic Studies of the Immunochemical Termination of Tolerance with Unnatural Amino Acids Example 2 characterizes the nature and durability of the polyclonal IgG antibody response created by incorporation of an unnatural amino acid(s) into TNFα and adds additional support for the generality of unnatural amino acid-induced (e.g., pNO$_2$Phe-induced) loss of self-tolerance. Example 2 shows that the mutation of several surface residues of murine tumor necrosis factor-α (mTNFα) independently to p-nitrophenylalanine (pNO$_2$Phe) lead to a T cell-dependent polyclonal and sustainable anti-mTNFα IgG autoantibody response lasting for at least 40 weeks. The Example shows that the antibodies bound multiple epitopes on mTNFα and protected mice from severe endotoxemia induced by lipopolysaccharide (LPS) challenge. Immunization of mice with a $pNO_2Phe^{43}$ mutant of murine retinol binding protein (RBP4) was also shown to elicit a high titer IgG antibody response, which was cross-reactive with wild-type mRBP4. Thus, Example 2 further supports that the current invention can be a general approach to generate effective immunotherapeutics against cancer-associated or other weakly immunogenic antigens.

For over two centuries active immunotherapy has been at the forefront of efforts to prevent infectious disease (Waldmann, T. A. (2003) "Immunotherapy: past, present and future" *Nat Med* 9:269-277). However, the decreased ability of the immune system to mount a robust immune response to self-antigens has made it more difficult to generate therapeutic vaccines against cancer or chronic degenerative diseases. Recently, we showed that the site-specific incorporation of an immunogenic unnatural amino acid into an autologous protein offers a simple and effective approach to overcome self-tolerance (see Grunewald, J. et al. (2008) "Immunochemical termination of self-tolerance" *Proc Natl Acad Sci USA* 105: 11276-11280 and Example 1). Here we characterize the nature and durability of the polyclonal IgG antibody response and begin to establish the generality of $pNO_2Phe$-induced loss of self-tolerance. Mutation of several surface residues of murine tumor necrosis factor-α (mTNFα) independently to p-nitrophenylalanine ($pNO_2Phe$) leads to a T cell-dependent polyclonal and sustainable anti-mTNFα IgG autoantibody response that lasts for at least 40 weeks. The antibodies bind multiple epitopes on mTNFα and protect mice from severe endotoxemia induced by lipopolysaccharide (LPS) challenge. Immunization of mice with a $pNO_2Phe^{43}$ mutant of murine retinol binding protein (RBP4) also elicited a high titer IgG antibody response, which was cross-reactive with wild-type mRBP4. These findings suggest that this may be a relatively general approach to generate effective immunotherapeutics against cancer associated or other weakly immunogenic antigens.

Critical to the process of immunological self-nonself discrimination is self-tolerance (Goodnow (2007) "Multistep pathogenesis of autoimmune disease" *Cell* 130:25-35), in which a mammal's immune system is "tolerized" to self-proteins in order to avoid autoimmune disease, primarily due to the absence or inactivation of self-reactive B- or T-cells. It has been known for years, however, that the immune system can be induced to attack self-proteins. For example, cross-reactive immune responses to self-proteins can be induced by introducing foreign T helper cell epitopes into chimeric antigens (Dalum, et al. (1999) "Therapeutic antibodies elicited by immunization against TNF-alpha" *Nat Biotechnol* 17:666-669, Zuany-Amorim, et al. (2004) "Induction of TNF-alpha autoantibody production by AutoVac TNF106: a novel therapeutic approach for the treatment of allergic diseases" *Int Arch Allergy Immunol* 133:154-163), by extensive chemical derivatization of self-antigens (Weigle, W. O. (1965) "The Induction of Autoimmunity in Rabbits Following Injection of Heterologous or Altered Homologous Thyroglobulin" *J Exp Med* 121:289-308), and by DNA vaccines (Leitner, et al. (2003) "Alphavirus-based DNA vaccine breaks immunological tolerance by activating innate antiviral Pathways" *Nat Med* 9:33-39). Furthermore, a number of specific genes and cellular mechanisms involved in self-tolerance have been identified which when disrupted result in breakdown of tolerance and autoimmune disease (Goodnow (2007) "Multistep pathogenesis of autoimmune disease" *Cell* 130:25-35; Hill, et al. (2008) "Recent acquisitions on the genetic basis of autoimmune disease" *Front Biosci* 13:4838-4851). Despite these advances, the design of effective immunotherapeutics has been a slow process, as exemplified by the fact that only a few vaccines for cancer treatment have reached late stage clinical development (Small, et al. (2006) "Placebo controlled phase III trial of immunologic therapy with sipuleucel-T (APC8015) in patients with metastatic, asymptomatic hormone refractory prostate cancer" *J Clin Oncol* 24:3089-3094; Schlom, et al. (2007) "Role of vaccine therapy in cancer: biology and practice" *Curr Oncol* 14:238-245).

Nitroaryl groups are highly immunogenic, likely due to their ability to form strong stacking and van der Waals interactions. Indeed, the nonspecific derivatization of autologous cancer cells with dinitrophenyl groups has been exploited as a vaccine in melanoma patients (Berd, D. (2004) "M-Vax: an autologous, hapten-modified vaccine for human cancer." *Expert Rev Vaccines* 3:521-527), and physiological 3'-nitrotyrosine formation has been implicated in the pathology of a number of autoimmune diseases (Aulak, et al. (2001) "Proteomic method identifies proteins nitrated in vivo during inflammatory challenge" *Proc Natl Acad Sci USA* 98:12056-12061; Pacher, et al. (2007) "Nitric oxide and peroxynitrite in health and disease" *Physiol Rev* 87:315-424; Hardy, et al. (2008) "Conversion of tyrosine to the inflammation-associated analog 3'-nitrotyrosine at either TCR- or MHC-contact positions can profoundly affect recognition of the MHC class I-restricted epitope of lymphocytic choriomeningitis virus glycoprotein 33 by CD8 T cells." *J Immunol* 180: 5956-5962). To test whether this immunogenic group could be used to break tolerance to specific self-proteins, we previously introduced a p-nitrophenylalanine (pNO$_2$Phe) residue at a single site in murine TNFα. Genetic substitution of pNO2Phe for Tyr86 of mTNFα created a T cell epitope, which enhanced T cell help to elicit a strong cross-reactive antibody response against this disease-related self-protein (Grunewald, J. et al. (2008) "Immunochemical termination of self-tolerance." *Proc Natl Acad Sci USA* 105: 11276-11280). Here, we show that immunochemical breakdown of self-tolerance leads to sustained high-titer antibody responses that efficiently protect mice against a lipopolysaccharide (LPS) challenge. Moreover, we demonstrate that this methodology is generalizable to a self-protein unrelated to immune function, namely retinol binding protein 4 (RBP4).

Mechanistic Studies of $pNO_2Phe$-Induced Breakdown of Self-Tolerance

Previously, we showed that substitution of $pNO_2Phe$ for Tyr86 in mTNFα led to a high titer cross-reactive antibody response to wildtype (WT) protein. The mutant protein was shown to induce T-cell proliferation in immunized animals, whereas WT protein did not (Grunewald, J. et al. (2008) "Immunochemical termination of self-tolerance." *Proc Natl Acad Sci USA* 105: 11276-11280). To provide further evidence for a T cell-dependent immune response against $pNO_2Phe$ TNFα, we have carried out ELISA analysis of the mTNFα autoantibodies with either anti-mouse IgM or anti-mouse IgG secondary antibody. The majority of the anti-mTNFα autoantibodies in sera from Bcl-2 mice immunized with $pNO_2Phe^{86}$ mTNFα are of the IgG subtype, indicating T cell-mediated immunoglobulin class switching (FIG. 16A). To determine whether the presence of $pNO_2Phe$ is critical throughout the immunization process, we initially injected 4 mice with $pNO_2Phe^{86}$ mTNFα in complete Freund's adjuvant (CFA) followed by 7 injections of either WT mTNFα or $pNO_2Phe^{86}$ mTNFα in incomplete Freund's adjuvant (IFA). The results shown in FIG. 20 clearly demonstrate that, in contrast to $pNO_2Phe^{86}$ mTNFα, WT mTNFα cannot sustain significant titers of cross-reactive anti-mTNFα antibodies. This result supports the notion that $pNO_2Phe$-induced breakdown of self-tolerance requires a T cell response mediated by the nitrophenyl group, and is consistent with previous studies which showed that a Tyr86Phe TNFα mutant is not able to elicit a strong immune response.

One question regarding the mechanism of $pNO_2Phe$-induced breakdown of self-tolerance is whether the antibody response is directed at the epitope that contains $pNO_2Phe$, or whether epitope spreading occurs, resulting in a polyclonal IgG response against multiple epitopes in the target protein. To address this issue, Bcl-2 mice were immunized with $pNO_2Phe^{86}$ mTNFα to generate 50 B cell hybridomas, which were screened by ELISA to identify those clones that produced antibodies against WT mTNFα. We then assessed the binding of these monoclonal antibodies (mAbs) to a set of three mTNFα fragments that were expressed in *E. coli* and whose molecular weights were verified by MALDI TOF (FIG. 21): an N-terminal fragment (aa 1-60), an internal fragment (aa 61-100), and a C-terminal fragment (aa 101-156). Although this assay largely detects specificities against linear (presumably continuous) B cell epitopes, we identified five mAbs (3L24, 5K19, 6J22, 7O1, and 7F23) that bound the N-terminal fragment and one mAb (1P19) that bound the C-terminal fragment (FIG. 22). Significantly, none of the mAbs bound the internal fragment encoding $pNO_2Phe^{86}$ in the original immunogen. Thus, antibodies binding more than one epitope are produced through $pNO_2Phe^{86}$ mTNFα immunization, and these epitopes do not necessarily include the $pNO_2Phe$ residue of the immunogen. The polyclonal IgGs from $pNO_2Phe^{86}$ mTNFα-immunized mice cross-react with native mTNFα with Kd values in the nanomolar range (FIG. 16B). Together, these results further support the hypothesis that a cross-reactive neutralizing antibody response can be generated against a self-protein by simply inserting a $pNO_2Phe$ residue into its sequence.

Sustainability of $pNO_2Phe$-Induced Antibody Response

To determine the durability of anti-mTNFα IgG antibody titers, we immunized three Bcl-2 mice with $pNO_2Phe^{86}$ mTNFα. After the last boost injection, bleeds were analyzed by ELISA against $pNO_2Phe^{86}$ mTNFα at defined time points. Remarkably, antibody levels were maintained at greater than 80% their initial levels for at least 40 weeks (FIG. 16C), after which time the mice were sacrificed. In contrast, in a previous anti-mTNFα vaccination study based on immunization with mTNFα mutant containing a hen egg-white lysozyme T-cell epitope, titers declined four weeks after the last boost, and after 26 weeks the mTNFα antibody titers had dropped by 80-87% (Dalum, et al. (1999) "Therapeutic antibodies elicited by immunization against TNF-alpha." *Nat Biotechnol* 17: 666-669). Thus, our $pNO_2Phe$-based vaccine strategy is effective in inducing persistent immunity and long-term protection against TNFα as a disease-associated self-antigen.

Extension to Mutations at Other Surface Sites within mTNFα

To examine the generality of the $pNO_2Phe$-induced breakdown of self-tolerance, four additional surface-exposed residues of mTNFα were mutated to $pNO_2Phe$: $Lys^{11}$, $Gln^{21}$, $Asp^{42}$, and $Val^{49}$ (FIG. 23A). These residues are also structurally distinct from p-nitrophenylalanine. After confirming the composition and homogeneity of $pNO_2Phe^{11}$ mTNFα, $pNO_2Phe$ mTNFα, $pNO_2Phe^{42}$ mTNFα, and $pNO_2Phe^{49}$ mTNFα by SDS-PAGE and mass spectrometry (FIG. 23B and Table 3), the quaternary structure of these mutant proteins was shown to be trimeric by size exclusion chromatography (Table 4). Furthermore, an NFκB-luciferase reporter gene assay showed that $pNO_2Phe^{11}$ mTNFα has 9%, $pNO_2Phe^{21}$ mTNFα has 22%, $pNO_2Phe^{42}$ mTNFα has 22%, and $pNO_2Phe^{49}$ mTNFα has 10% of the activity of WT mTNFα (Table 4 and FIG. 23C). All mutants are therefore significantly more active than the previously characterized $pNO_2Phe^{86}$ mTNFα, which has only 2% of the activity of the wild-type protein in this assay. To determine the immunogenicity of these $pNO_2Phe$ mTNFα mutants, fourteen C57BL/6 mice were randomized into five groups and injected with these mutants, or WT mTNFα by the RIMMS (repetitive immunization at multiple sites) protocol (Kilpatrick, et al. (1997) "Rapid development of affinity matured monoclonal antibodies using RIMMS." *Hybridoma* 16: 381-389). An ELISA analysis revealed no correlation between mTNFα activity in the NFκB-luciferase reporter gene assay and the ability to induce an antibody response, ruling out a direct effect on the immune system. As shown in FIG. 17, pNO$_2$Phe at position 11 induced a high titer IgG response to WT mTNFα, equivalent to that against the pNO$_2$Phe[11] mTNFα immunogen. In contrast, although mutations of positions 21, 42, and 49 also yielded high titer IgG responses against the pNO$_2$Phe-containing immunogen, the IgG antibodies had only moderate cross-reactivity to WT mTNFα. Antibodies generated against all four mutant TNFαs were then used for passive immunization of forty C57BL/6 mice, which were randomized into five groups and injected with the anti-pNO$_2$Phe or anti-WT mTNFα IgG. Twenty-four hours after passive immunization, the animals were challenged with LPS as described previously (Niessen, et al. (2008) "Dendritic cell PAR1-S1P3 signalling couples coagulation and inflammation." *Nature* 452: 654-658). All mice receiving anti-pNO$_2$Phe[11] mTNFα IgG survived the lethal LPS challenge (FIG. 18). Even the other groups receiving moderately cross-reactive anti-pNO$_2$Phe[21] mTNFα IgG, anti-pNO$_2$Phe[42] mTNFα IgG, and anti-pNO$_2$Phe[49] mTNFα IgG had survival rates of at least 75%; whereas mice injected with anti-WT mTNFα IgG showed a survival rate of only 13%. Thus, the ability to break self-tolerance using pNO$_2$Phe is not dependent on a single amino acid position, since we have shown that at least five positions (including position 86) can induce a neutralizing cross-reactive anti-mTNFα IgG response in vivo. Moreover, the site of substitution does not need to be structurally similar to p-nitrophenylalanine.

TABLE 3

ESI mass spectrometry analysis of mRBP4 variants

| Sample | Method | Full-length protein | Protein without Met[1] |
|---|---|---|---|
| pNO$_2$Phe[11] mTNFα | MALDI TOF | 19178 (19232) | |
| pNO$_2$Phe[21] mTNFα | MALDI TOF | 19191 (19232) | |
| pNO$_2$Phe[42] mTNFα | MALDI TOF | 19222 (19245) | |
| pNO$_2$Phe[49] mTNFα | MALDI TOF | 19249 (19261) | |
| pNO$_2$Phe[43] MRBP4 | ESI | 23710 (23710) | 23579 (23579) |
| pNO$_2$Phe[108] MRBP4 | ESI | 23710 (23710) | 23579 (23579) |
| WT mRBP4 | ESI | n.d. (23681) | 23550 (23550) |

(n.d., not detected)

TABLE 4

Quaternary structure determination and NF-κB-luciferase activity analysis of mTNFα variants.

| Sample | Observed mass (calculated mass of trimer) (kDa) | EC50 (M) | R² |
|---|---|---|---|
| WT mTNFα | 55.5 (51.8) | 2.163 × 10 − 10 | 0.9944 |
| pNO$_2$Phe[11] mTNFα | 55.7 (57.5) | 2.465 × 10 − 9 | 0.9992 |
| pNO$_2$Phe[21] mTNFα | 51.9 (57.5) | 9.651 × 10 − 10 | 0.9981 |
| pNO$_2$Phe[42] mTNFα | 50.9 (57.5) | 9.668 × 10 − 10 | 0.9985 |
| pNO$_2$Phe[49] mTNFα | 52.3 (57.5) | 2.133 × 10 − 9 | 0.9989 |
| pNO$_2$Phe[86] mTNFα | 55.2 (51.9) | 1.124 × 10 − 8 | 0.9979 |

Expression and Characterization of Mutant mRBP4 Proteins

Figure 24:
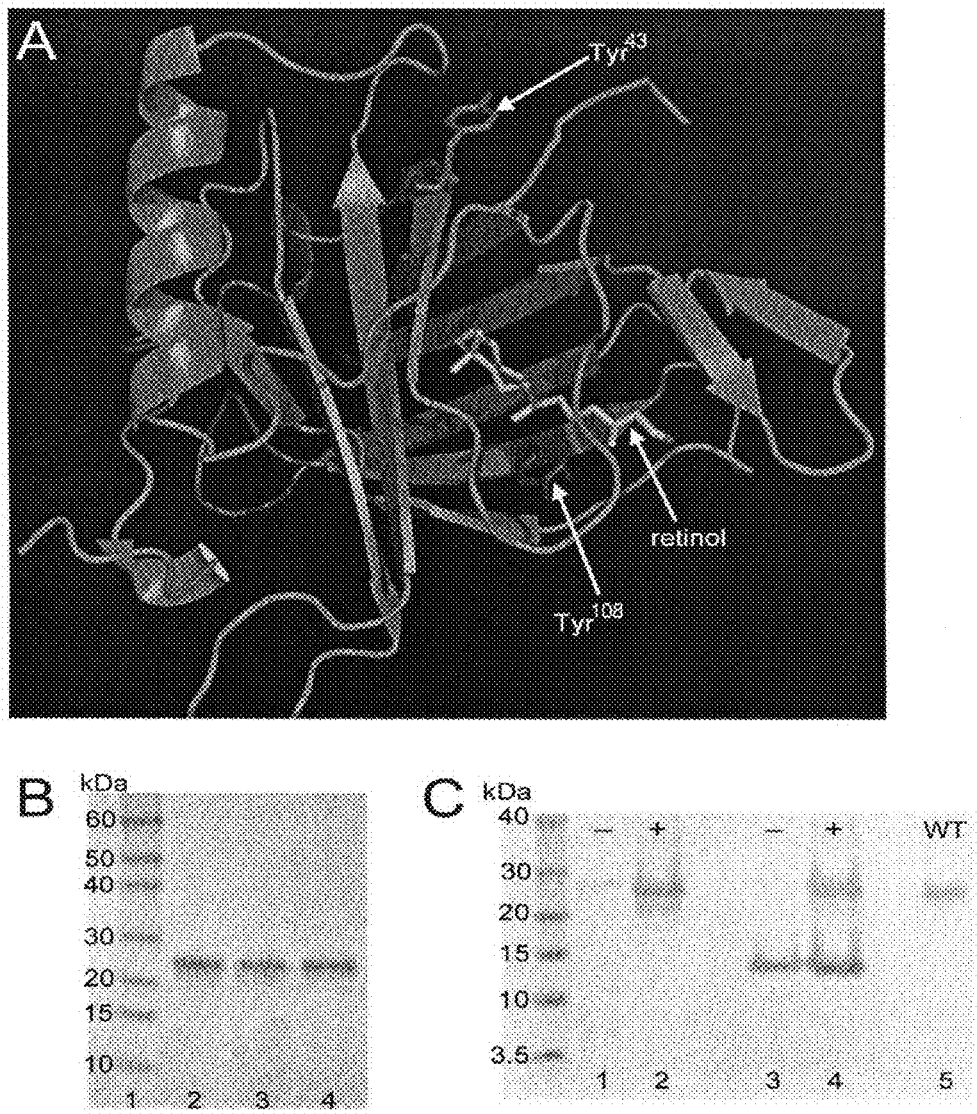
FIG. 24 depicts the results of experiments performed to confirm the incorporation of $pNO_2Phe$ into surface-exposed sites of mRBP4.

Given that multiple positions within mTNFα lead to breakdown of self-tolerance when mutated to pNO$_2$Phe, we then asked whether this methodology could be generalized to other self-proteins. Specifically, we examined the ability of pNO$_2$Phe to break self-tolerance against another model self-protein found in serum, RBP4 (Zanotti, et al. (2004) "Plasma retinol-binding protein: structure and interactions with retinol, retinoids, and transthyretin." *Vitam Horm* 69: 271-295; Raghu, et al. (2004) "Interactions amongst plasma retinol-binding protein, transthyretin and their ligands: implications in vitamin A homeostasis and transthyretin amyloidosis." *Biochim Biophys Acta* 1703: 1-9). In contrast to TNFα, this is a highly soluble, relatively low molecular weight (20 kDa), monomeric protein. RBP4 knockout mice show no apparent phenotypic abnormalities other than visual deficiency (Vogel, et al. (2002) "Retinol-binding protein-deficient mice: biochemical basis for impaired vision." *Biochemistry* 41: 15360-15368), suggesting that mice will survive a neutralizing immune response against self-RBP4. Based on the x-ray crystal structure of monomeric human RBP4 (Cowan, et al. (1990) "Crystallographic refinement of human serum retinol binding protein at 2A resolution." *Proteins* 8: 44-61), we selected the following surface-exposed residues for mutation to pNO$_2$Phe: Tyr[43] and Tyr[108] (FIG. 24). These residues are highly conserved among different mammalian RBP4s, including murine RBP4 (mRBP4). These mRBP4 mutants as well as WT mRBP4 were expressed in *E. coli* as N-terminal His6-tagged proteins, purified by Ni2+ affinity chromatography under denaturing conditions, and refolded according to a previously described protocol (Greene, et al. (2001) "Role of conserved residues in structure and stability: tryptophans of human serum retinol-binding protein, a model for the lipocalin superfamily." *Protein Sci* 10: 2301-2316). The site-specific incorporation of pNO$_2$Phe into mRBP4 at positions 43 and 108 was confirmed by SDS-PAGE analysis, as well as by MS/MS fragmentation of the tryptic fragments containing the unnatural amino acid (FIGS. 24, 25 and 27). Analytical size-exclusion chromatography indicated a monomeric structure for all mRBP4 proteins, which is in agreement with the published quaternary structure of human RBP4 (Table 5) (Cowan, et al. (1990) "Crystallographic refinement of human serum retinol binding protein at 2A resolution." *Proteins* 8: 44-61). Moreover, according to a retinol displacement assay, all pNO$_2$Phe mRBP4 mutants bind retinol with Kd values in the nanomolar range, which is in good agreement with WT mRBP4 (Table 5).

TABLE 5

Quaternary structure determination and retinol binding affinities of mRBP4 proteins.

| Sample | Sample Retention time (min) | Observed mass (calculated mass of monomer) (kDa) | Kd (nM) |
|---|---|---|---|
| pNO$_2$Phe[43] mRBP4 | 42.63 | 9.6 (23.7) | 191.4 |
| pNO$_2$Phe[108] mRBP4 | 41.84 | 10.9 (23.7) | 229.5 |
| WT mRBP4 | 42.51 | 9.8 (23.7) | 170.8 |

The quaternary structures of pNO$_2$Phe[43] mRBP4, pNO$_2$Phe[108] mRBP4, and WT mRBP4 were determined based on a plot of the logarithm of the molecular mass of the protein standards versus the retention time on a Superdex 75 10/300 GL column. The binding affinities of mRBP4 proteins were determined by a TR-FRET retinol binding assay.

Generality of pNO$_2$Phe-Induced Breakdown of Self-Tolerance

Figure 26:
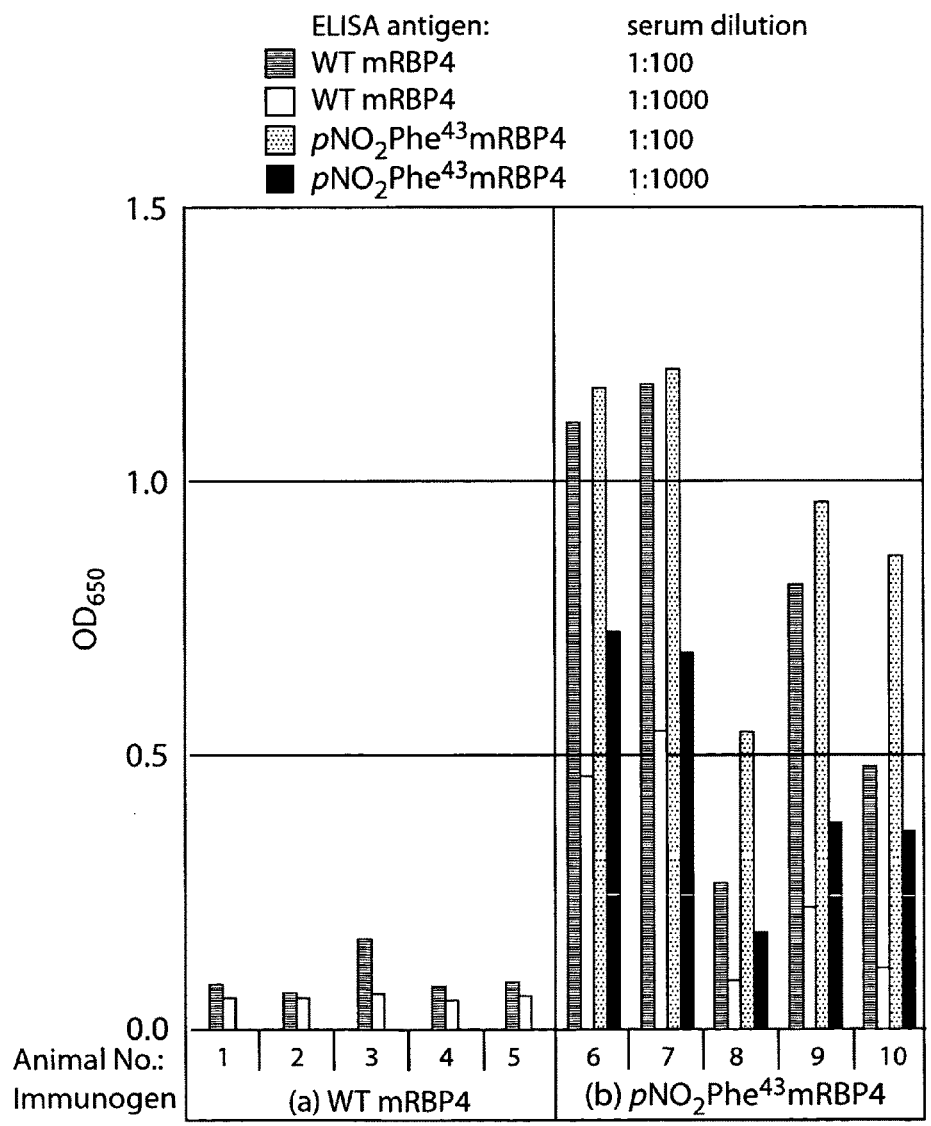
FIG. 26 depicts the results of experiments that were performed to determine the immunogenicity of $pNO_2Phe^{43}$ mRBP4 in C57BL/6 mice.

To determine the immunogenicity of the pNO$_2$Phe mRBP4 mutants, twelve Bcl2 mice were randomized into four groups and injected with pNO$_2$Phe$^{43}$ mRBP4, pNO$_2$Phe$^{108}$ mRBP4, and WT mRBP4 by the RIMMS protocol. (See, e.g., Kilpatrick, et al. (1997) "Rapid development of affinity matured monoclonal antibodies using RIMMS." *Hybridoma* 16: 381-389). According to ELISA analysis, mice immunized with either WT mRBP4 or pNO$_2$Phe$^{108}$ mRBP4 had insignificant serum IgG titers against WT mRBP4 (FIG. 19A). In contrast, mice immunized with pNO$_2$Phe$^{43}$ mRBP4 were found to display markedly high serum IgG titers (up to 1:100,000), binding both the pNO$_2$Phe$^{43}$ mRBP4 immunogen and the wild-type protein. Similar results were obtained with C57BL/6 mice (FIG. 26). Furthermore, in accordance with previous observations with pNO$_2$Phe$^{86}$ mTNFα, CD4$^+$ T cells specific for pNO$_2$Phe$^{43}$ mRBP4 were induced upon immunization with pNO$_2$Phe$^{43}$ mRBP4 protein, indicating a mature T cell-dependent immune response (FIG. 19B). Together, these results further support the hypothesis that the introduction of pNO$_2$Phe into a protein sequence can create a strong T cell epitope, which initiates a sustained cross-reactive IgG antibody response. Not all sites lead to a strong cross-reactive immune response, which is not surprising since it is unlikely that all sites correspond to potential T cell epitopes.

We have shown that the genetic introduction of pNO$_2$Phe leads to sustained IgG antibody responses against the self-proteins mTNFα and mRBP4. In terms of mechanism, incorporation of the p-nitrophenyl group at a single position results 10 in T cells that can only be stimulated by the pNO2Phe mutant but not the WT protein. This pNO$_2$Phe-induced T cell-dependent response ultimately leads to activation of autoreactive B cells and the production of polyclonal antibodies that are highly cross-reactive to the native self-protein. These results are comparable to recent studies showing that post-translationally modified proteins can enhance T cell responsiveness (Cantaert, et al. (2006) "Citrullinated proteins in rheumatoid arthritis: crucial . . . but not sufficient!" *Arthritis Rheum* 54: 3381-3389; Backlund, et al. (2002) "Predominant selection of T cells specific for the glycosylated collagen type II epitope (263-270) in humanized transgenic mice and in rheumatoid arthritis." *Proc Natl Acad Sci USA* 99: 9960-9965; Dzhambazov, et al. 2005) "The major T cell epitope on type II collagen is glycosylated in normal cartilage but modified by arthritis in both rats and humans" *Eur J Immunol* 35: 357-366). For example, citrullination and glycosylation are post-translational modifications involved in T cell-dependent autoimmune diseases (Cantaert, et al. (2006) "Citrullinated proteins in rheumatoid arthritis: crucial . . . but not sufficient!" *Arthritis Rheum* 54: 3381-3389; Backlund, et al. (2002) "Predominant selection of T cells specific for the glycosylated collagen type II epitope (263-270) in humanized transgenic mice and in rheumatoid arthritis." *Proc Natl Acad Sci USA* 99: 9960-9965; Dzhambazov, et al. (2005) "The major T cell epitope on type II collagen is glycosylated in normal cartilage but modified by arthritis in both rats and humans" *Eur J Immunol* 35: 357-366; Klareskog, et al. (2008) "Immunity to citrullinated proteins in rheumatoid arthritis." *Annu Rev Immunol* 26: 651-675; Sollid, L. M. (2000) "Molecular basis of celiac disease." *Annu Rev Immunol* 18: 53-81). Similarly, dinitrofluorobenzene modification of skin antigens has been used for decades as a model of the T cell response in contact hypersensitivity (Toews, et al. (1980) "Epidermal Langerhans cell density determines whether contact hypersensitivity or unresponsiveness follows skin painting with DNFB." *J Immunol* 124: 445-453). Site-specific incorporation of pNO$_2$Phe into self-proteins therefore establishes a simple model system to biochemically mimic post-translationally or chemically mediated loss of self-tolerance. This methodology should therefore also help to understand how the immune system responds to chemically modified antigens during autoimmunity. Furthermore, pNO$_2$Phe-induced breakdown of self-tolerance should not only afford a robust method for raising neutralizing antibodies against pathogenic self proteins associated with cancer or degenerative diseases, it can also be applicable to weakly immunogenic foreign antigens of infectious agents.

Bacterial Strains and Reagents

*E. coli* XL1-Blue and XL10-Gold were used as hosts for cloning, and *E. coli* BL21(DE3) was used as an expression strain. Restriction enzymes, T4 DNA ligase, dNTPs, and factor Xa protease were obtained from NEB (Beverly, Mass.). Primers were purchased from Integrated DNA Technologies (Coralville, Iowa). Plasmid DNA preparation was carried out with PureLink™ Quick Plasmid Miniprep Kit (Invitrogen), and DNA purification after restriction digestion was performed using PureLink™ PCR Micro Kit (Invitrogen).

Production of pNO$_2$Phe-Containing mTNFα and WT mTNFα

WT mTNFα and pNO$_2$Phe mTNFα mutants were produced as previously described (Grunewald, J. et al. (2008) "Immunochemical termination of self-tolerance." *Proc Natl Acad Sci USA* 105: 11276-11280). Briefly, site-specific incorporation of pNO$_2$Phe into the murine TNFα gene was carried out by introducing TAG amber codons using standard PCR mutagenesis procedures. To express pNO$_2$Phe mTNFα mutants, *E. coli* BL21(DE3) cells were cotransformed with mutNO$_2$PheRS, mutRNACUA and the mutated mTNFα gene. The transformed cells were then grown in the presence of 1 mM pNO$_2$Phe (Alfa Aesar, Ward Hill, Mass.) in minimal medium containing 1% glycerol and 0.3 mM leucine (GMML medium) at 37° C. and protein expression was initiated by the addition of 1 mM IPTG. WT mTNFα was expressed in 2×YT medium in the absence of pNO$_2$Phe. Protein purification was carried out by immobilized metal affinity chromatography (IMAC) and size-exclusion chromatography (SEC) under either native or denaturing conditions. All proteins were characterized by MALDI-TOF or ESI mass spectrometry. Successful incorporation of pNO$_2$Phe into mutant proteins was also verified by tryptic in-gel digestion and subsequent MS/MS fragmentation of the respective tryptic fragment containing this unnatural amino acid. Protein quaternary structures were analyzed by analytical SEC on a Superdex 75 10/300 GL gel filtration column, which was calibrated by a molecular weight gel-filtration standard from Bio-Rad (Bio-Rad Labs, Hercules, Calif.). The activity of pNO$_2$Phe mTNFα mutants was determined by an NFκB-luciferase reporter gene assay using HEK293 cells stably expressing NFκB-luciferase as described previously (Grunewald, J. et al. (2008) "Immunochemical termination of self-tolerance." *Proc Natl Acad Sci USA* 105: 11276-11280).

Construction of mRBP4 Expression Vector, pSpeedET-mRBP4

The cDNA encoding murine RBP4 (aa 19-201) (Genomics Institute of the Novartis Research Foundation) was amplified with PCR using two primers designed specifically for the Polymerase Incomplete Primer Extension (PIPE) cloning method (Klock, et al. (2008) "Combining the polymerase incomplete primer extension method for cloning and mutagenesis with microscreening to accelerate structural genomics efforts." *Proteins* 71: 982-994): 5'-CTGTACTTC-CAGGGCGAGCGCGACTGCAGGG (5' insert forward primer, SEQ ID NO: 3) and 5'-AATTAAGTCGCGTTA-CAAACTGTTTCTGGAGGGCC (3' insert reverse primer, SEQ ID NO: 4). The pSpeedET vector was amplified using a 5' vector reverse primer 5'-GCCCTGGAAGTACAG- GTTTTCGTGATGATGATGATGATG (SEQ ID NO: 5)and a 3' vector forward primer 5'-TAACGCGACTTAAT-TAACTCGTTTAAACGGTCTCCAGC (SEQ ID :6). The underlined and italicized bases highlight the two distinct complementary regions between primers where annealing occurs. The pSpeedET vector appends an N-terminal His6-tag sequence (MGSDKIHHHHHH), followed by a TEV protease site (ENLYFQG) immediately before the 19th codon for mRBP4. The unpurified mRBP4 (aa 19-201) insert PCR product was mixed 1:1 (v/v) with the unpurified pSpeedET vector PCR product. After mixing, E. coli XL10-Gold cells were transformed with 2 µL of the reaction mixture. Site-specific incorporation of pNO$_2$Phe into mRBP4 (aa 19-201) was performed by mutating the codons for Tyr43 or Tyr108 to a TAG amber codon. The sequences of all pSpeedET-mRBP4 constructs were confirmed by DNA sequence analysis.

Protein Expression and Purification of pNO2Phe mRBP4 and WT mRBP4

To express the pNOPhe mRBP4 mutants, E. coli BL21 (DE3) cells were cotransformed with mutNO$_2$PheRS, mutR-NACUA, and the respective mutant mRBP4 gene. The transformed strains were grown at 37° C. in the presence of 1 mM pNO$_2$Phe in GMML medium, induced with 0.2% (w/v) arabinose when the OD$_{600}$ reached 0.5, and harvested after 12-16 h. In contrast to the pNO$_2$Phe mRBP4 mutants, WT mRBP4 was expressed in 2×YT medium in the absence of pNO$_2$Phe for 3 h. The cell pellets were suspended in 8 M urea containing 100 mM NaH$_2$PO$_4$, 10 mM Tris (pH 8.0) and lysed by sonication on ice for 3 minutes. Cell debris was removed by centrifugation at 40,000×g for 25 min. 5 ml 50% Ni-NTA slurry (Novagen, Madison, Wis.) was added to the supernatant and mixed gently by shaking for 60 minutes. The Ni-NTA beads were washed with 8 M urea, 100 mM NaH$_2$PO$_4$, and 10 mM Tris (pH 6.3). Elution was carried out with 8 M urea containing 100 mM NaH$_2$PO$_4$, and 10 mM Tris (pH 4.5). The protein was concentrated with a 10 K molecular mass cut-off Amicon Ultra-15 centrifugal filter device (Millipore, Bedford, Mass.). The mRBP4 protein was precipitated by dialysis against phosphate buffered saline (PBS, pH 7.4), and redissolved in 8 M urea containing 20 mM Tris and 20 mM dithiothreitol (pH 8.0). In vitro folding of mRBP4 protein was performed according to Greene, et al. (2001) "Role of conserved residues in structure and stability: tryptophans of human serum retinol-binding protein, a model for the lipocalin superfamily." *Protein Sci* 10: 2301-2316. Briefly, native protein was generated by adding the denatured material in 8 M urea dropwise to folding buffer containing 20 mM Tris, 10 mM β-mercaptoethanol, 1 mM 2-hydroxyethyldisulfide, and 1% glycerol (pH 8.5) at a rate of ~30 drops/minute. Folding was allowed to proceed for 16 h at 4° C., and the protein solution was then concentrated using a 10K molecular mass cut-off Amicon Ultra-15 centrifugal filter device (Millipore). The protein was further purified by SEC on a Superdex 75 10/300 GL column (GE Healthcare, Piscataway, N.J.) equilibrated with PBS (pH 7.4) at a flow rate of 0.3 ml/minute.

Mouse Model of Severe Systemic Inflammation

All experiments were carried out in accordance with the National Institutes of Health Animal Protection Guidelines and were approved by The Scripps Research Institute Animal Care and Use Committee. Animal experiments were performed in a room with alternating 12 h light dark cycles under stable conditions of temperature (20-22° C.) and relative humidity (40-60%) (Niessen, et al. (2008) "Dendritic cell PAR1-S1P3 signalling couples coagulation and inflammation." *Nature* 452: 654-658). Twenty four hours before LPS challenge, 9-week old male C57BL/6 mice (Jackson Laboratories, Bar Harbor, Me.) were passively immunized by injection into the left half of the peritoneal cavity with 4 mg/kg of IgG purified from serum of mice immunized with pNO$_2$Phe[11] mTNFα, pNO$_2$Phe[21] mTNFα, pNO$_2$Phe[42] mTNFα, and pNO$_2$Phe[49] mTNFα IgG derived from non-immunized wild-type mice was employed as a negative control. Mice were then injected into the right half of the peritoneal cavity under 2% isoflurane with 7.5 mg/kg lipopolysaccharide (LPS, E. coli O111:B4 Calbiochem/EMD Biosciences, La Jolla, Calif.). For statistical analysis, Kaplan-Meier curves were plotted and survival differences were analyzed using a log rank test with Bonferroni correction.

ELISA

30 µl of 0.5 µg/ml protein was used to coat the wells of Maxisorp 384-well plates (Nunc, Rochester, N.Y.) overnight at 4° C. After washing with PBS+0.05% Tween 20 (PBST), the coated plates were blocked with 80 µl of 1% BSA in PBS, and washed again with PBST. The plates were sequentially incubated with 20 µl of primary antibody or serum diluted in 1% BSA in PBS, 20 µl of HRP-conjugated goat anti-mouse IgG or anti-mouse IgM (Jackson ImmunoResearch Laboratories, West Grove, Pa.), and 20 µl of TMB substrate (KPL, Gaithersburg, Md.), and read at an absorbance of 650 nm. Between incubations, the plates were washed at least six times with PBST.

T Cell Proliferation Assay

Isolation of CD4$^+$ T cells from the lymph nodes of immunized C57BL/6 mice was carried out by magnetic depletion with MACS beads (Miltenyi Biotec, Auburn, Calif.). T cells were then placed into culture with irradiated splenocytes from naïve C57BL/6 mice and increasing amounts of antigen. Following incubation for 48 h, the cultures were incubated with $^3$H-thymidine overnight. After harvesting the culture plates onto filter mats, radioactivity was quantified with a TopCount scintillation counter (PerkinElmer, Boston, Mass.).

Murine RBP4 Activity Assay

WT and pNO$_2$Phe mRBP4 mutant proteins were labeled with biotin using the Sulfo-NHS-Biotin kit (Pierce, Rockford, Ill.) according to manufacturer instructions. For determination of retinol binding activity, 10 nM biotin-labeled RBP4 was mixed with 1 nM Streptavidin-Europium chelate (LANCE® Eu-W8044 Streptavidin, Perkin Elmer, Foster City, Calif.). Increasing concentrations of Cy5-labeled retinol were added to the reaction and retinol binding was assessed by homogeneous time-resolved fluorescence resonance energy transfer (TR-FRET).

Immunization and Generation of Monoclonal Antibody (mAb)

Purified WT or pNO$_2$Phe mTNFα was used as immunogen to produce anti-mTNFα antibodies. Bcl-2 transgenic mice (C57BU6-TgN(BCL2)$_{22}$Wehi) or C57BL/6 mice were immunized using the RIMMS protocol. See, e.g., Kilpatrick, et al. (1997) "Rapid development of affinity matured monoclonal antibodies using RIMMS." *Hybridoma* 16: 381-389. Bcl-2 transgenic mice demonstrate extended B cell survival and follicular lymphoproliferation making them especially suitable for immunization. Briefly, mice were injected 8 times over 18 days. In each injection, 5 µg of protein in 200 µl PBS was 1:1 mixed with complete Freund's adjuvant (first injection) or with incomplete Freund's adjuvant (for the remaining injections). Immunogen was injected at 6 specific sites proximal to peripheral lymph nodes (PLNs). On the day of the 8th injection, a test bleed was collected, and the serum antibody titer was analyzed by ELISA. PLNs from a high serum titer mouse were harvested and dissociated. The isolated lymphocytes were fused to F0 mouse myeloma cells using 50% PEG 1500. Fused cells were plated in a 384-well tissue culture plate. Hybridomas were selected in hypoxanthine aminopterin thymidine (HAT) medium and screened by ELISA against WT mTNFα.

Explanation of Results Depicted in Figures of Example 2

Figure 16A:
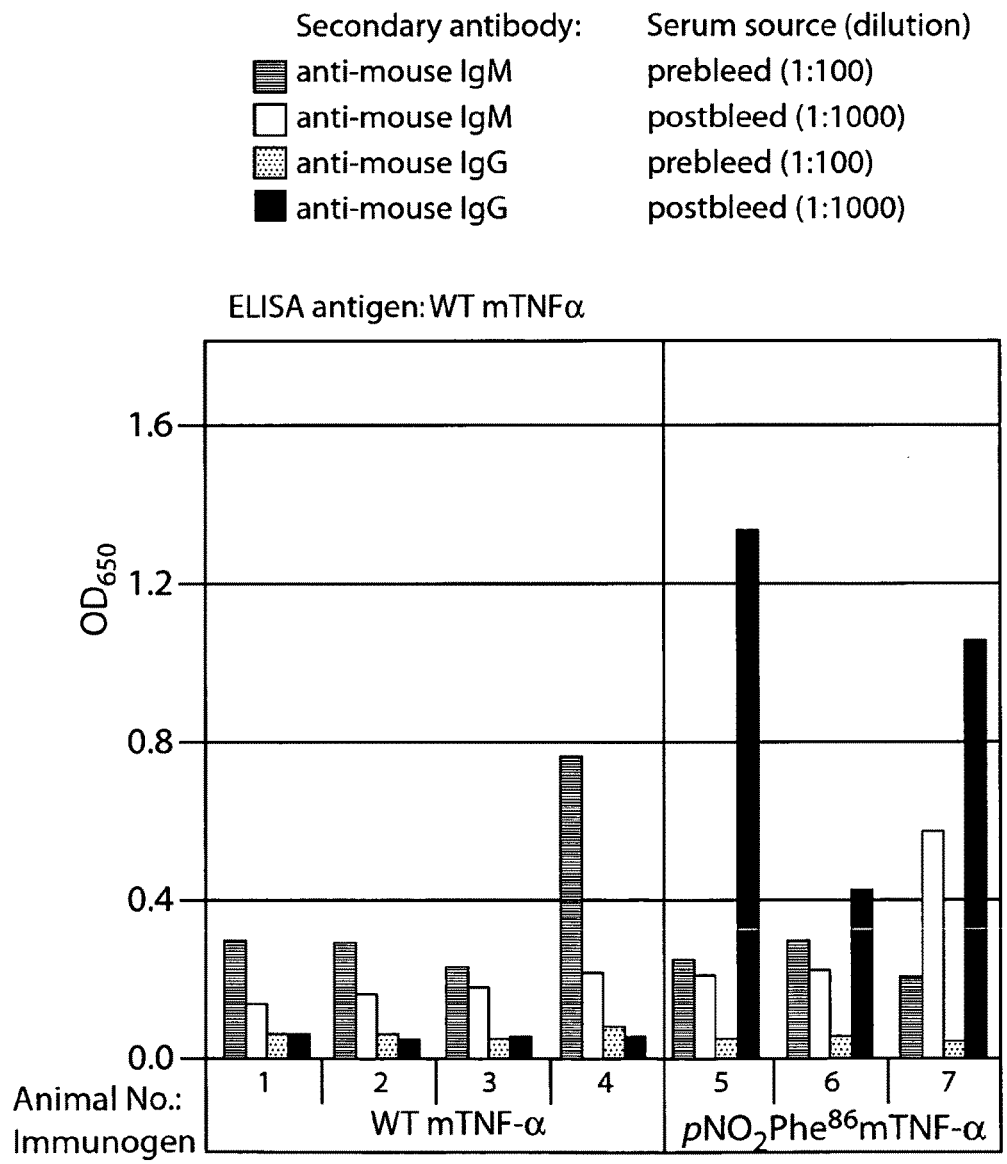
FIG. 16 shows that $pNO_2Phe^{86}$ mTNFα immunization promotes class-switching to an IgG response, which displays significant cross-reactivity with WT mTNFα and lasts for at least 40 weeks in mice.
Figure 16B:
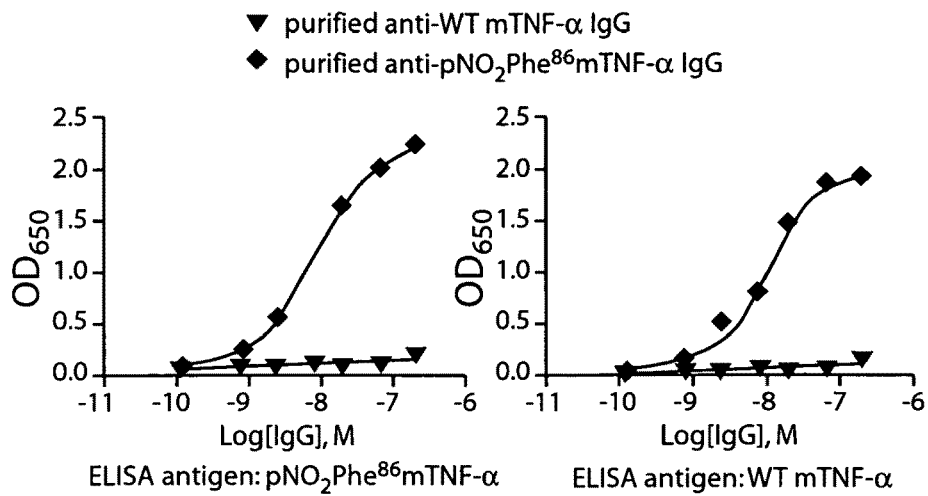
Figure 16C:
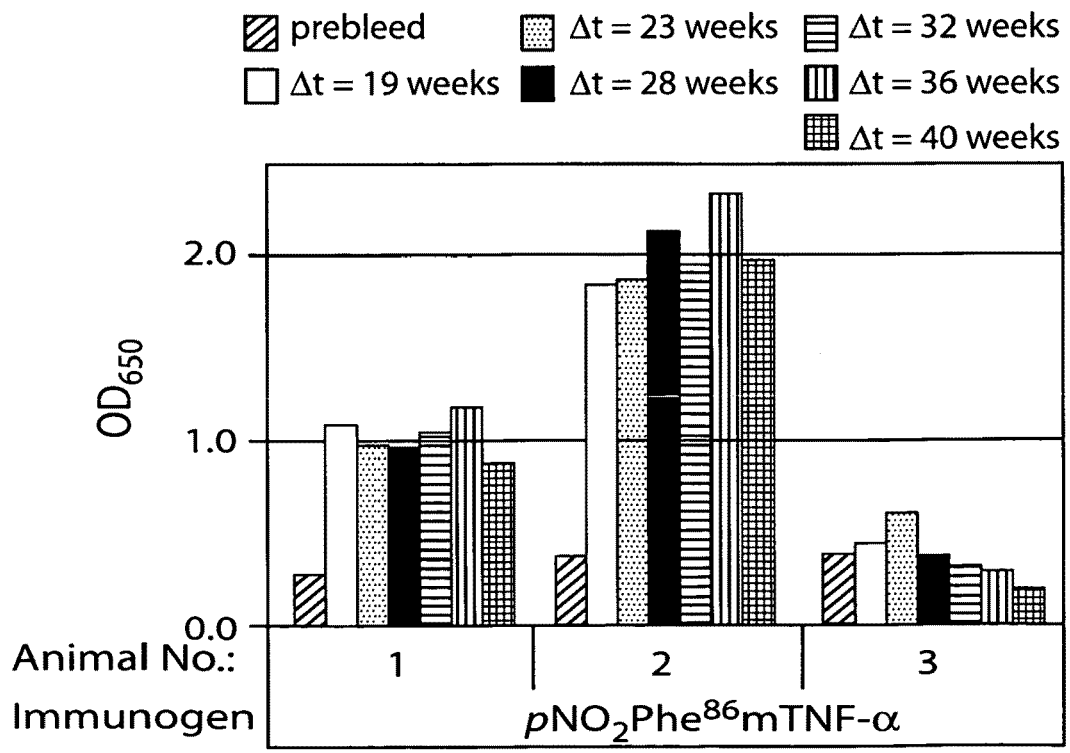

FIG. 16 shows the results of experiments that were performed to determine whether pNO$_2$Phe$^{86}$ mTNFα immunization promotes class-switching to an IgG response. The IgG response that was detected displays significant cross-reactivity with WT mTNFα and lasts for at least 40 weeks in mice. In FIG. 16A, serum titers for Bcl-2 mice immunized with pNO$_2$Phe$^{86}$ mTNFα or WT mTNFα were determined over a period of 17 days in the presence of complete Freund's adjuvant (CFA) for the initial injection and incomplete Freund's adjuvant (IFA) for the remainder. ELISAs were measured against WT mTNFα using either anti-mouse IgM (first and second bars in each group of four bars) or anti-mouse IgG (third and fourth bars in each group of four bars) as a secondary antibody. Before measurement, serum samples were diluted 1:100 (first and third bars) or 1:1,000 (second and fourth bars) with 1% BSA in PBS buffer. FIG. 16B shows ELISA titrations that were performed to quantify the affinity of polyclonal anti-WT mTNFα IgG (inverted triangles) and polyclonal anti-pNO$_2$Phe$^{86}$ mTNFα IgG (diamonds) for either pNO$_2$Phe$^{86}$ mTNFα or WT mTNFα. FIG. 16C shows serum titer durability study of three Bcl-2 mice immunized with pNO$_2$Phe$^{86}$ mTNFα. After a sequence of eight immunizations, bleeds were taken for 20 ELISA analysis against pNO$_2$Phe$^{86}$ mTNFα at defined time points (Δt corresponds to the time period between the last immunization and the bleed). Before each measurement, serum samples were diluted 1:100 with 1% BSA in PBS buffer. The first bar in each group of 7 bars is prebleed, the second bar is Δ19 weeks, the third bar is Δ23 weeks, the fourth bar is Δ28 weeks, the fifth bar is Δ32 weeks, the sixth bar is Δ36 weeks, and the seventh bar is Δ40 weeks.

Other surface-exposed sites on mTNFα are also significantly immunogenic. In FIG. 17A, serum titers against WT mTNFα (left bars in each pair of bars), pNO$_2$Phe$^{11}$ mTNFα (right bars in pairs 3, 4, and 5), and PBS (right bars in pairs 1 and 2) for C57BL/6 mice immunized with pNO$_2$Phe$^{11}$ mTNFα or WT mTNFα are shown. In FIG. 17B, serum titers against WT mTNFα (left bars in each pair of bars), pNO$_2$Phe$^{21}$ mTNFα (right bars in pairs 6, 7, and 8), and PBS (right bars in pairs 1 and 2) for C57BL/6 mice immunized with pNO$_2$Phe$^{21}$ mTNFα or WT mTNFα are shown. In FIG. 17C, serum titers against WT mTNFα (left bars in each pair of bars), pNO$_2$Phe$^{42}$ mTNFα (right bars in pairs 9, 10, and 11), and PBS (right bars in pairs 1 and 2) for C57BL/6 mice immunized with pNO$_2$Phe$^{42}$ mTNFα or WT mTNFα are shown. In FIG. 17D, serum titers against WT mTNFα (left bars in each pair of bars), pNO$_2$Phe$^{49}$ mTNFα (right bars in pairs 12, 13, and 14), and PBS right bars in pairs 1 and 2) for C57BL/6 mice immunized with pNO$_2$Phe$^{49}$ mTNFα or WT mTNFα are shown. Before each measurement, serum samples were diluted (17A) 1/800; (17B) 1/200; (17C) 1/200; or (17D) 1/200 with 1% BSA in PBS buffer.

The results indicate that pNO$_2$Phe at position 11 induced a high titer IgG response to WT mTNFα, equivalent to that against the pNO$_2$Phe$^{11}$ mTNFα immunogen. In contrast, although mutations of positions 21, 42, and 49 also yielded high titer IgG responses against the pNO$_2$Phe-containing immunogen, the IgG antibodies had only moderate cross-reactivity to WT mTNFα.

FIG. 18 shows that there exists a significant survival benefit for mice immunized with various pNO$_2$Phe mTNFα mutants after lipopolysaccharide (LPS) challenge. In FIG. 18A, Male C57BL/6 mice were intraperitoneally injected with 4 mg/kg purified IgG from mice immunized with pNO$_2$Phe$^{11}$ mTNFα and pNO$_2$Phe$^{49}$ mTNFα one day before LPS challenge. In FIG. 18B, the mice were intraperitoneally injected with 4 mg/kg purified IgG from mice immunized with pNO$_2$Phe$^{21}$ mTNFα and pNO$_2$Phe$^{42}$ mTNFα one day before LPS challenge. Kaplan-Meier survival plots of these mice were compared to mice injected with control IgG (n=8/group). Survival advantage of mice immunized with each modified TNF p<0.01 versus control, log rank test with Bonferroni correction.

Figure 19:
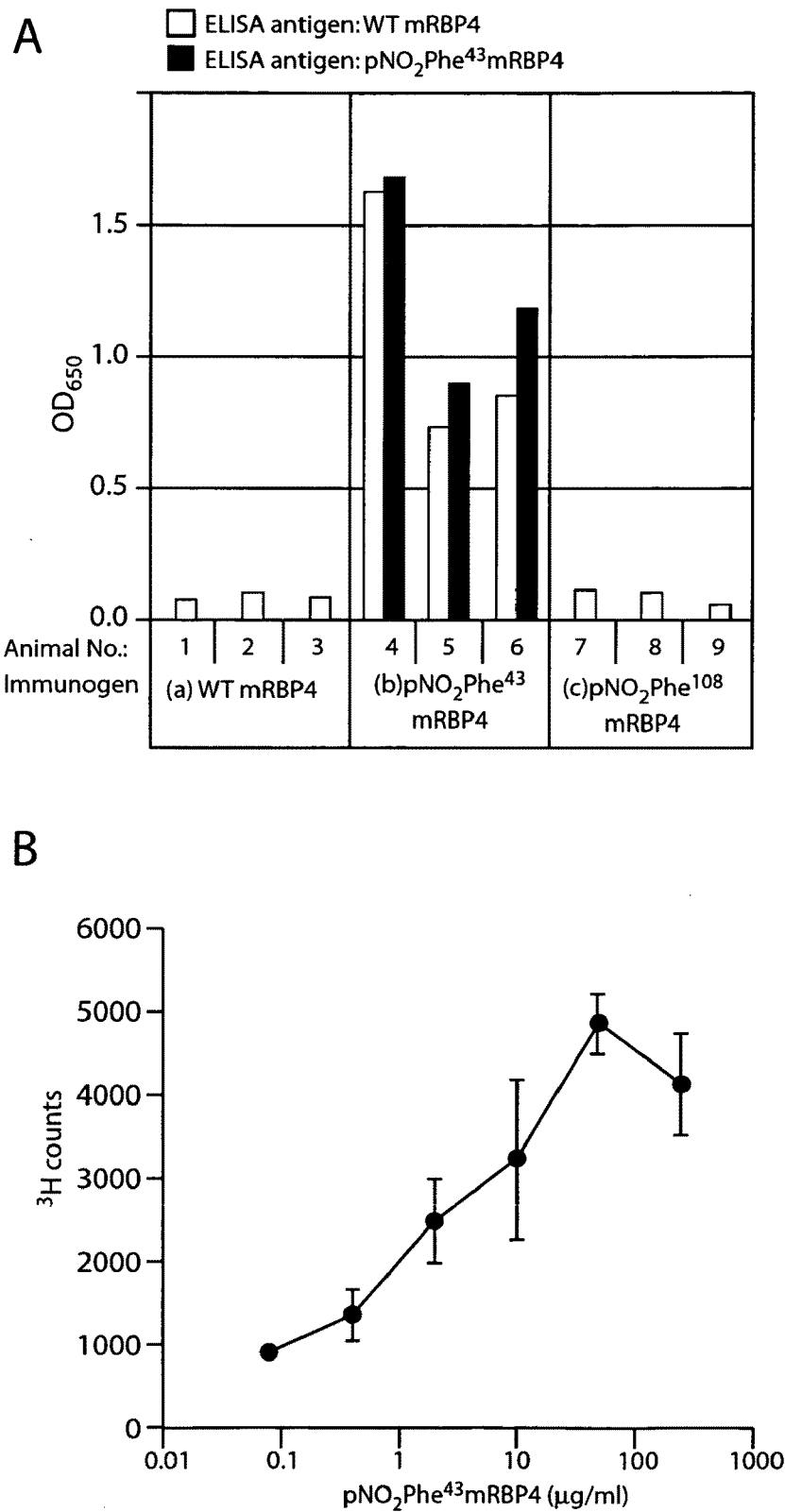
FIG. 19 depicts the results of experiments performed to determine whether the incorporation of $pNO_2Phe$ the self-antigen mRBP4 can cause loss of tolerance mRBP4.

All mice receiving anti-pNO$_2$Phe$^{11}$ mTNFα IgG survived the lethal LPS challenge. Even the other groups receiving moderately cross-reactive anti-pNO$_2$Phe$^{21}$ mTNFα IgG, anti-pNO$_2$Phe$^{42}$ mTNFα IgG, and anti-pNO$_2$Phe$^{49}$ mTNFα IgG had survival rates of at least 75%; whereas mice injected with anti-WT mTNFα IgG showed a survival rate of only 13%. Thus, the ability to break self-tolerance using pNO$_2$Phe is not dependent on a single amino acid position FIG. 19 depicts the results of experiments that show the loss of tolerance to a second self-antigen, mRBP4. Serum titers for Bcl-2 mice immunized with WT mRBP4 (19A); pNO$_2$Phe$^{43}$ mRBP4 (19B); pNO$_2$Phe$^{108}$mRBP4 (19C), are shown. ELISAs were measured against WT mRBP4 (single bars in 1, 2, 3, 7, 8, and 9; left bars in each pair of bars 4, 5, and 6) and pNO$_2$Phe$^{43}$ mRBP4 (right bars in each pair of bars 4, 5, and 6). Before measurement, serum samples were diluted 1:1,000 with 1% BSA in PBS buffer. FIG. 19B depicts results that show the proliferation of CD4$^+$ T cells from C57BU6 mice immunized with pNO$_2$Phe$^{43}$ mRBP4 and stimulated in vitro with serial dilutions of pNO$_2$Phe$^{43}$ mRBP4.

Figure 20:
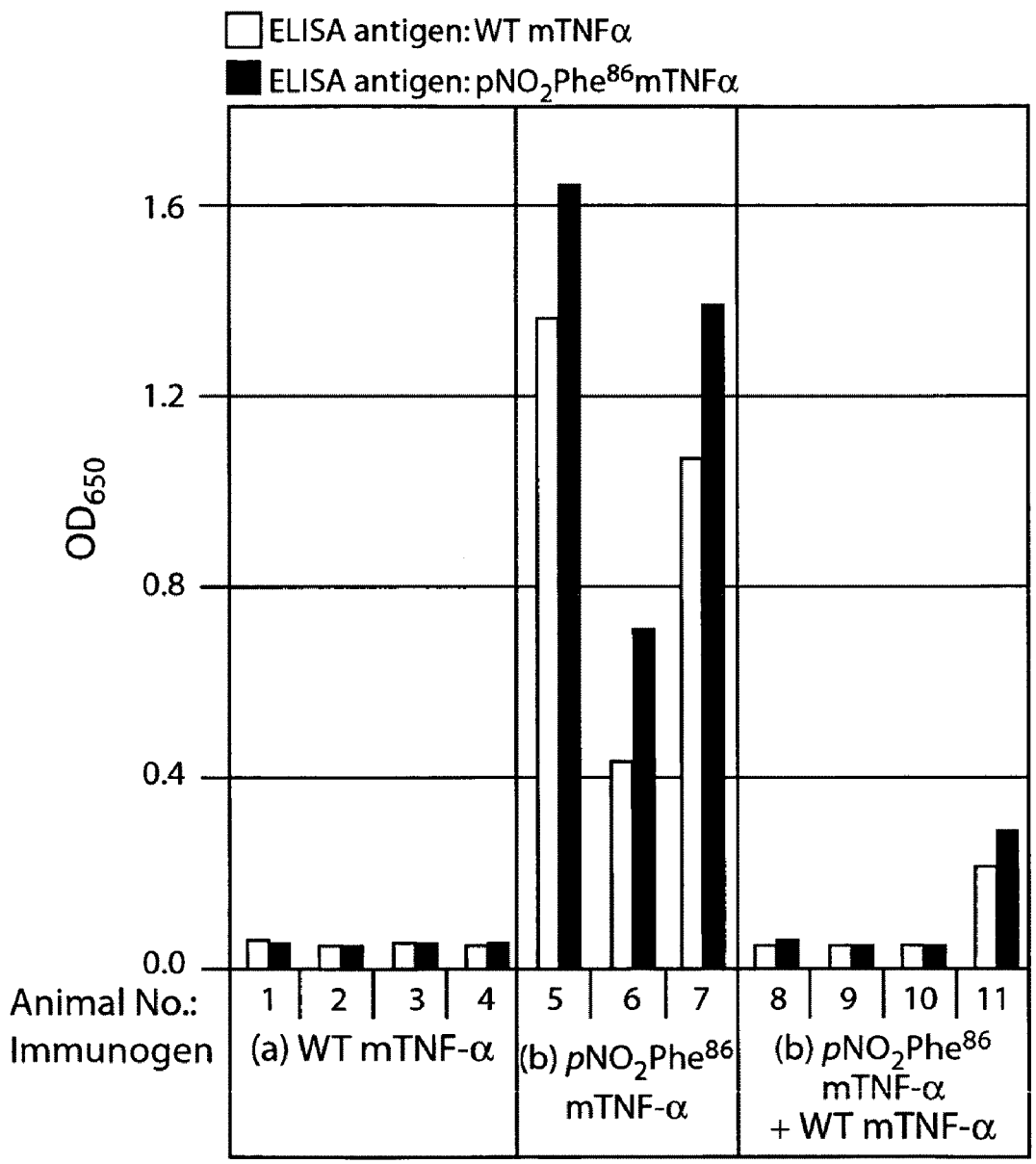
FIG. 20 shows that WT mTNFα cannot sustain $pNO_2Phe^{86}$ mTNFα induced loss of tolerance.
Figure 21:
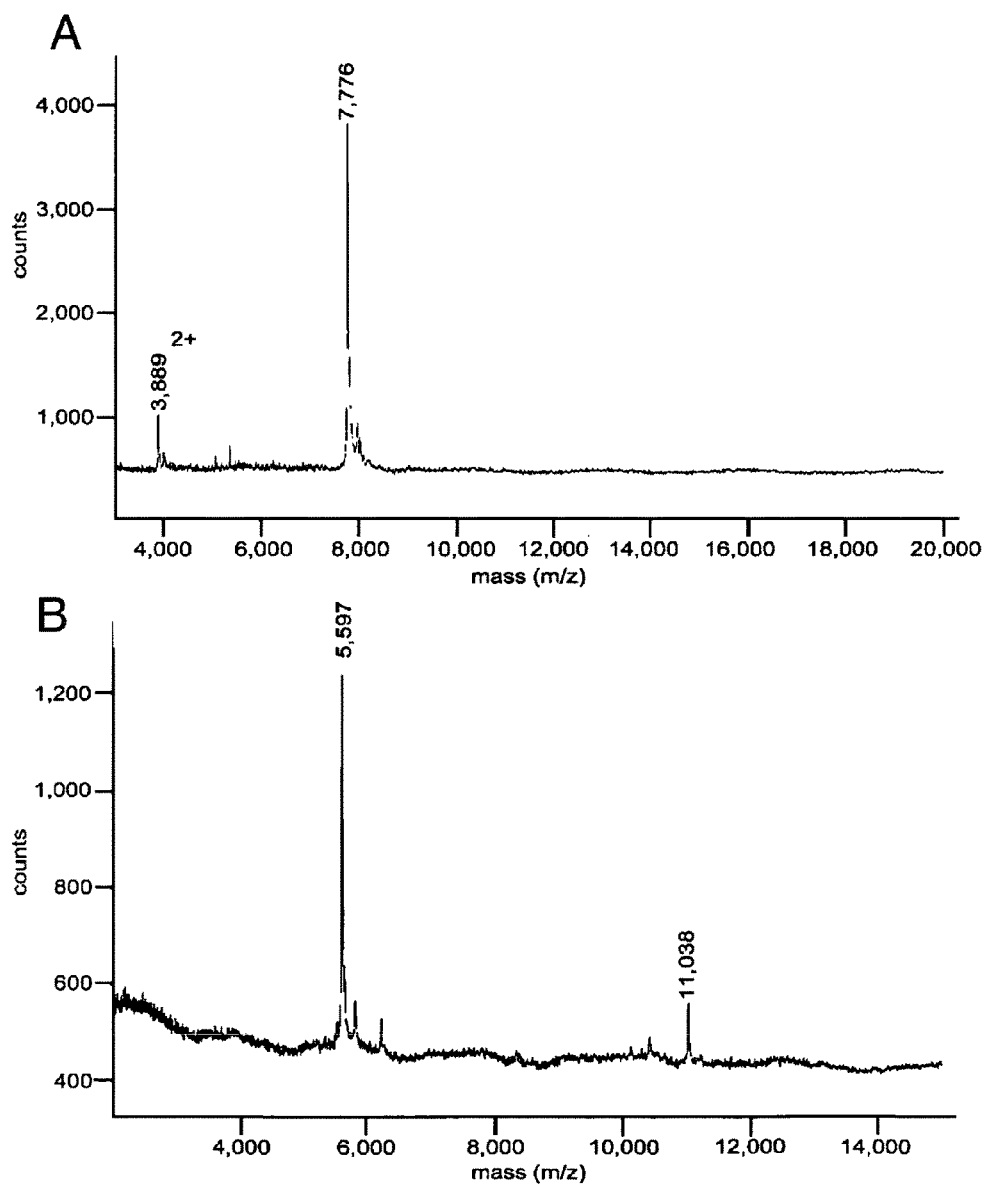
FIG. 21 shows the mass spectrometric analyses of three mTNFα fragments.
Figure 21C:
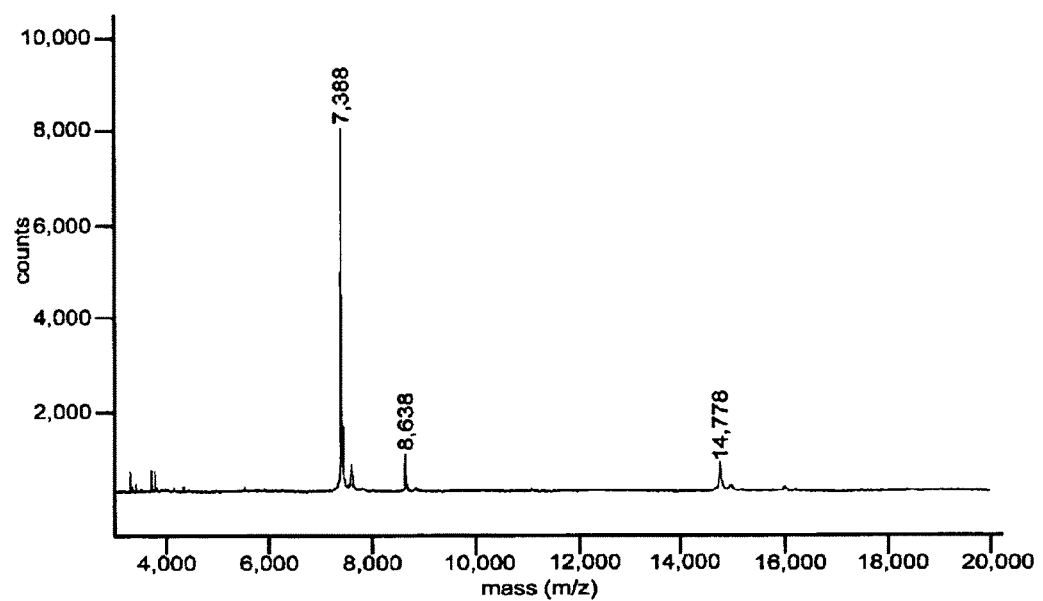

According to the ELISA analyses in FIG. 19, mice immunized with either WT mRBP4 or pNO$_2$Phe$^{108}$ mRBP4 had insignificant serum IgG titers against WT mRBP4. In contrast, mice immunized with pNO$_2$Phe$^{43}$ mRBP4 were found to display markedly high serum IgG titers (up to 1:100,000), binding both the pNO$_2$Phe$^{43}$ mRBP4 immunogen and the wild-type protein FIG. 20 shows that WT mTNFα cannot sustain pNO$_2$Phe$^{86}$ mTNFα induced loss of tolerance. Serum titers for Bcl-2 mice immunized by the RIMMS protocol with WT mTNFα (20A), pNO$_2$Phe mTNFα (20B), and pNO$_2$Phe$^{86}$ mTNFα followed by WT mTNFα (20C). For (20C), the immunization involved one initial injection of pNO$_2$Phe$^{86}$ mTNFα in CFA and seven subsequent injections of WT mTNFα in IFA. Before ELISA measurements, serum samples were diluted 1:1,000 with 1% BSA in PBS buffer. ELISAs were measured against WT mTNFα (left bars in each pair of bars) or pNO$_2$Phe$^{86}$ mTNFα (right bars in each pair of bars). In contrast to pNO$_2$Phe$^{86}$ mTNFα, WT mTNFα cannot sustain significant titers of cross-reactive anti-mTNFα antibodies. This result supports the notion that pNO$_2$Phe-induced breakdown of self-tolerance requires a T cell response mediated by the nitrophenyl group FIG. 21 shows the results of mass spectrometric analyses of three mTNFα fragments. FIG. 21A shows MALDI-TOF mass spectrometric analysis of N-terminal fragment mTNFα (aa 1-60); calc. mass, 7776.51. FIG. 21B shows MALDI-TOF mass spectrometric analysis of internal fragment mTNFα (aa 61-100); calc. mass, 5597.36. FIG. 21C shows MALDI-TOF mass spectrometric analysis of C-terminal fragment mTNFα (aa 101-156); calc. mass, 7388.18. The peaks in each panel in FIG. 21 confirm that each of the TNFα fragments are the expected mass.

Figure 22:
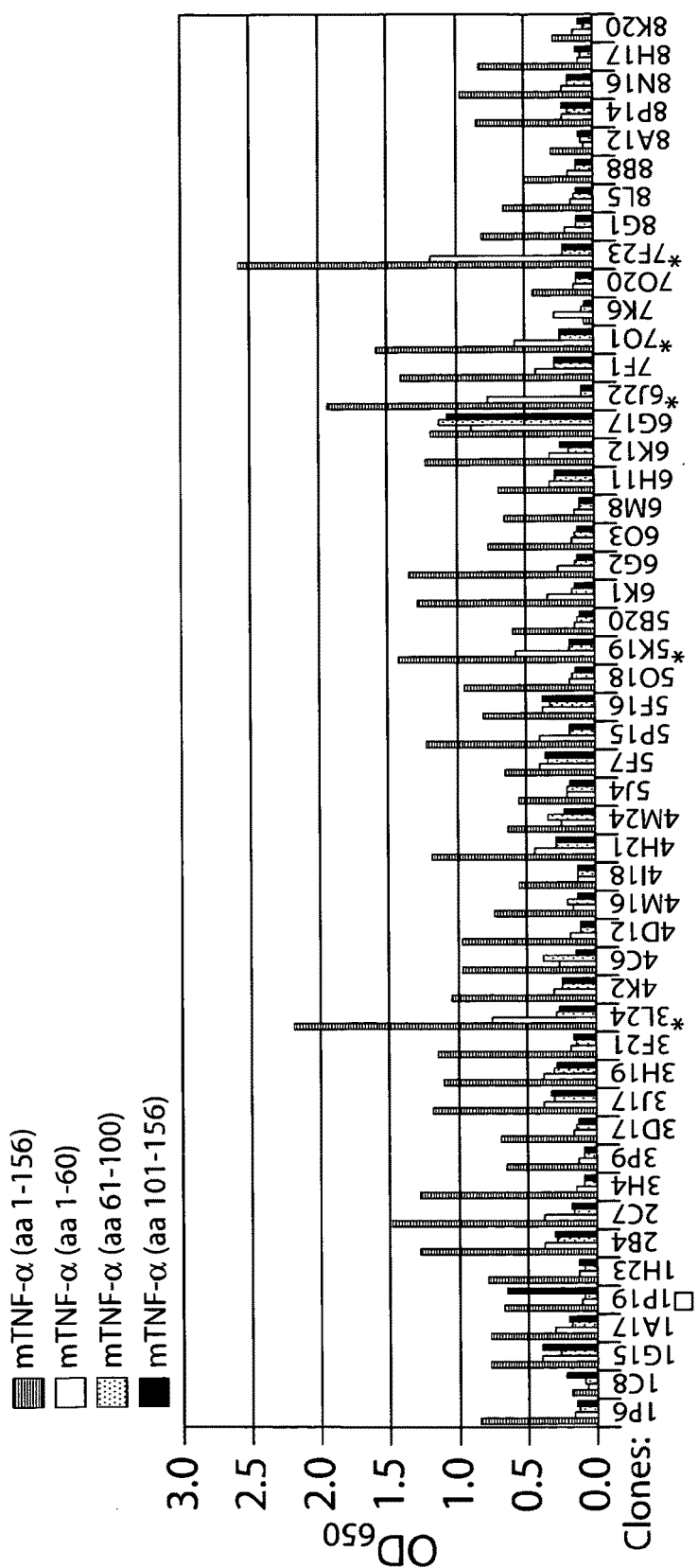
FIG. 22 shows the binding of anti-mTNFα mAbs to three mTNFα fragments.

Experiments were performed to determine the binding of anti-mTNFα mAbs to three mTNFα fragments. In FIG. 22, ELISAs were measured against WT mTNFα aa 1-156 (first bars in each group of four bars) or WT mTNFα aa 1-60

(second bars in each group of four bars), WT mTNFα aa 61-100 (third bars in each group of four bars), and WT mTNFα aa 101-156 (fourth bars in each group of four bars). Fifty hybridomas that secreted anti-mTNFα IgG were generated from pNO$_2$Phe$^{86}$ mTNFα-immunized mice. Three fragments of mTNFα were expressed and purified from *E. coli*: an N-terminal fragment (aa 1-60), an internal fragment (aa 61-100), and a C-terminal fragment (aa 101-156). Note that the pNO$_2$Phe is encoded at position 86 (internal fragment) in the original immunogen. ELISA analysis was performed using each fragment and WT mTNFα as a control. Antibodies that bind one of the fragments are marked: square, N-terminal fragment; asterisk, C-terminal fragment). Only six mAbs were found to clearly recognize one fragment. One mAb (6G17) recognized all three and likely represents non-specific binding activity. Of note, none of the 50 mAbs recognize a linear epitope corresponding to the middle fragment, which is the region that contains the pNO$_2$Phe in the mutant TNFα.

Figure 23:
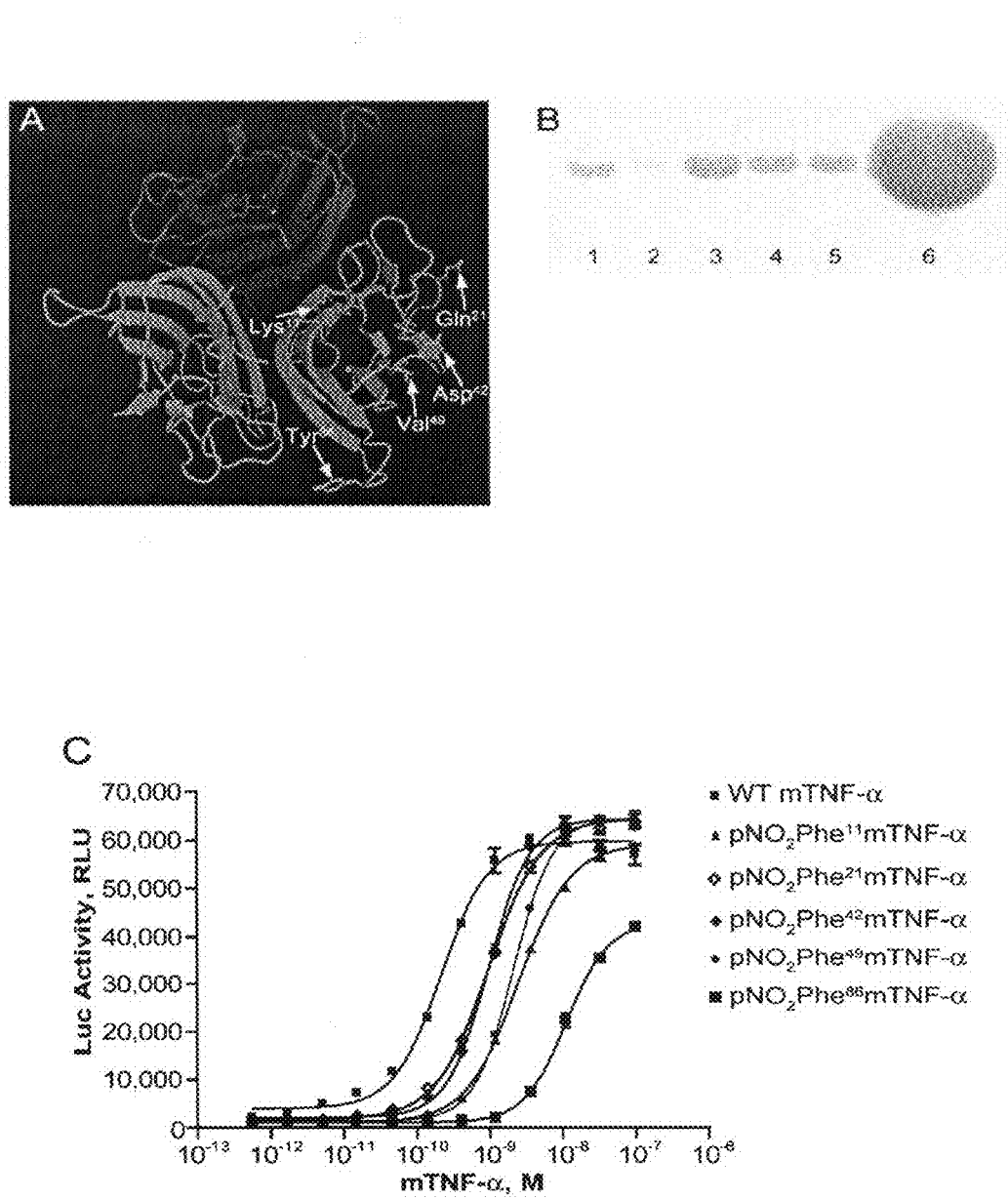
FIG. 23 depicts the results of experiments performed to confirm the incorporation of $pNO_2Phe$ into surface-exposed sites of mTNFα.

FIG. 23 shows the results of experiments performed to determine whether pNO$_2$Phe was incorporated into surface-exposed sites of mTNFα. FIG. 23A provides a schematic of a X-ray crystal structure of mTNFα trimer with Lys, Gln$^2$, Asp$^{42}$, Val$^{49}$, and Tyr$^{86}$ indicated (PDB ID code 2TNF)$^{30}$. See, Baeyens, et al. (1999) "The structure of mouse tumour-necrosis factor at 1.4 Å resolution: towards modulation of its selectivity and trimerization." Acta Crystallogr D Biol Crystallogr 55: 772-8. FIG. 23B shows SDS-PAGE gel analysis of pNO$_2$Phe$^{11}$ mTNFα (lane 1), pNO$_2$Phe$^{19}$ mTNFα (lane 2), pNO$_2$Phe$^{21}$ mTNFα (lane 3), pNO$_2$Phe$^{42}$ mTNFα (lane 4), pNO$_2$Phe$^{49}$ mTNFα (lane 5), and WT mTNFα (lane 6). Protein samples were purified by Ni-NTA affinity chromatography under native conditions and analyzed by SDS PAGE with Coomassie G-250 staining. FIG. 23C provides the results of NF-κB-luciferase activity analysis of WT mTNFα (small squares), pNO$_2$Phe$^{11}$ mTNFα (triangles), pNO$_2$Phe$^{21}$ mTNFα (hollow diamonds), pNO$_2$Phe$^{42}$ mTNFα (filled diamonds), pNO$_2$Phe$^{49}$ mTNFα (circles), and pNO$_2$Phe$^{86}$ mTNFα (large squares). All mutants are therefore significantly more active than the previously characterized pNO$_2$Phe$^{86}$ mTNFα, which has only 2% of the activity of the wild-type protein in this assay.

FIG. 24 shows the results of experiments performed to confirm the site-specific insertion of pNO$_2$Phe into surface sites of mRBP4. FIG. 24A provides a schematic of a X-ray crystal structure of human RBP4 with Tyr$^{43}$ and Tyr$^{108}$ indicated (PDB ID code 1RBP)$^{21}$. See, Cowan, et al. (1990) Crystallographic refinement of human serum retinol binding protein at 2A resolution. *Proteins* 8: 44-61). The retinol cofactor is shown in yellow. FIG. 24B shows SDS-PAGE analysis of WT mRBP4, pNO$_2$Phe$^{43}$ mRBP4, and pNO$_2$Phe$^{108}$ mRBP4 after Ni-NTA affinity chromatography and size-exclusion chromatography, indicating that each mutant trimerizes. FIG. 24C shows the expression of the Tyr$^{43}$ amber mutant of mRBP4 in the absence (lane 1) and presence (lane 2) of 1 mM pNO$_2$Phe; the Tyr$^{108}$ amber mutant of mRBP4 in the absence (lane 3) and presence (lane 4) of 1 mM pNO$_2$Phe. These results show that pNO$_2$Phe is incorporated into the mRBP mutants with high specificity. Protein samples were purified by Ni-NTA affinity chromatography under denaturing conditions and analyzed by SDS-PAGE with Coomassie G-250 staining. Lane 5 contains WT mRBP4.

Figure 25A:
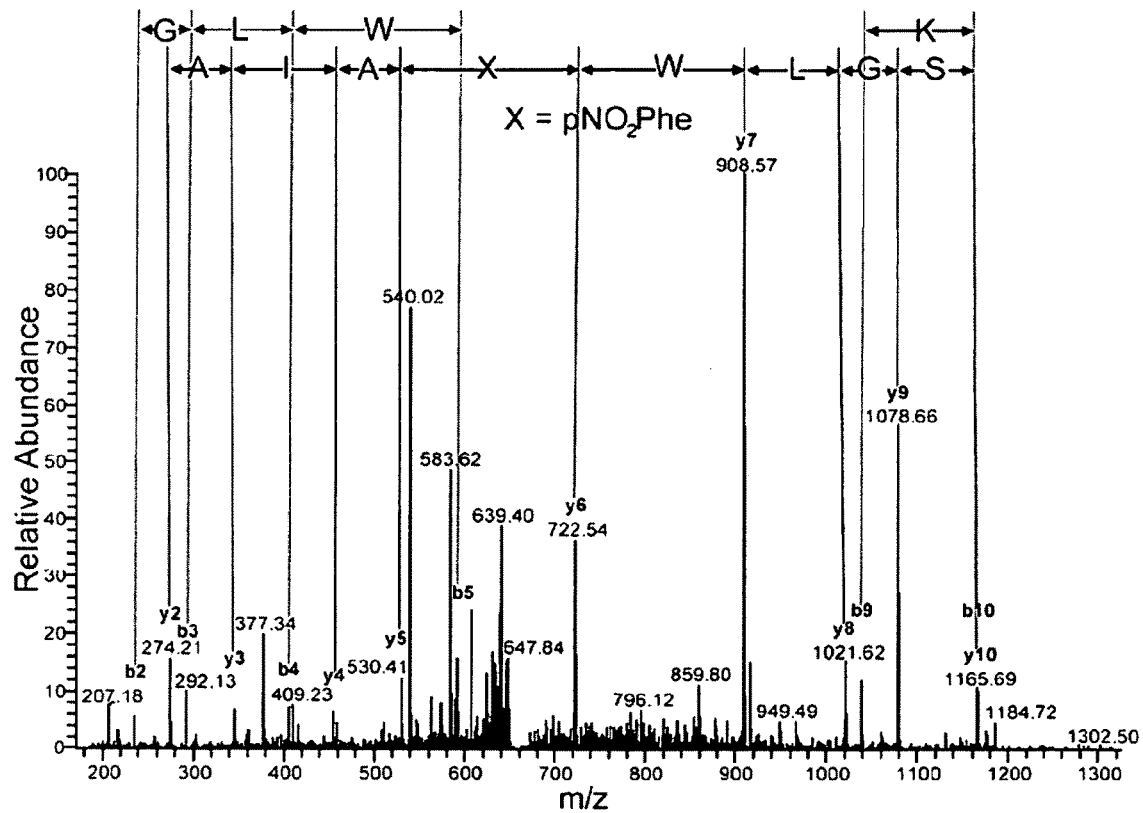
FIG. 25 shows that MS/MS analyses of tryptic fragments of $pNO_2Phe^{43}$ mRBP4 and $pNO_2Phe^{108}$ mRBP4 matches the pattern for the incorporation of $pNO_2Phe$.
Figure 25B:
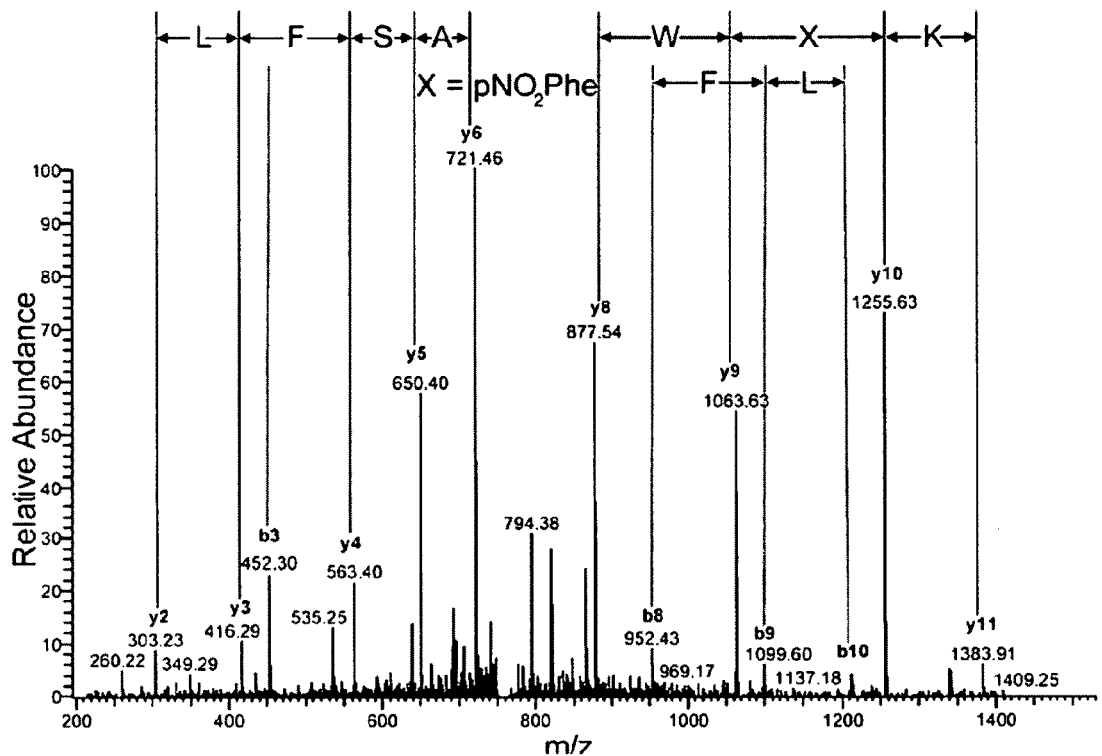

In FIG. 25, MS/MS analyses of tryptic fragments of pNO$_2$Phe$^{43}$ mRBP4 and pNO$_2$Phe$^{108}$ mRBP4 match the patterns for the incorporation of pNO$_2$Phe. FIG. 25A shows a tandem mass spectrum of the undecamer fragment FSGL-WXAIAKK (SEQ ID NO: 7), where X denotes pNO$_2$Phe. The fragment was produced from trypsin digestion of pNO$_2$Phe$^{43}$ mRBP4. FIG. 25B shows a tandem mass spectrum of the dodecamer fragment MKXWGVASFLQR (SEQ ID NO: 8), where X denotes pNO$_2$Phe. This fragment was produced from trypsin digestion of pNO$_2$Phe$^{108}$ mRBP4. The partial sequence of the peptide oligomers containing pNO$_2$Phe can be read from the annotated b or y ion series.

FIG. 26 depicts the results of experiments that were performed to determine the immunogenicity of pNO$_2$Phe$^{43}$ mRBP4 in C57BL/6 mice. FIG. 26A shows serum titers against WT mRBP4 and pNO$_2$Phe$^{43}$ mRBP4 for C57BL/6 mice immunized with WT mRBP4. FIG. 26B shows serum titers against WT mRBP4 and pNO$_2$Phe$^{43}$ mRBP4 for C57BL/6 mice immunized with pNO$_2$Phe$^{43}$ mRBP4. ELISAs were measured against WT mRBP4 (second and first bars in groups 1-10) or pNO$_2$Phe$^{43}$ mRBP4 (fourth and third bars in groups 6-10). Before measurement, serum samples were diluted either 1:100 or 1:1,000 with 1% BSA in PBS buffer.

According to these ELISA analyses, mice immunized with either WT mRBP4 or pNO$_2$Phe$^{108}$ mRBP4 had insignificant serum IgG titers against WT mRBP4. In contrast, mice immunized with pNO$_2$Phe$^{43}$ mRBP4 were found to display markedly high serum IgG titers (up to 1:100,000), binding both the pNO$_2$Phe$^{43}$ mRBP4 immunogen and the wild-type protein.

Figure 27A:
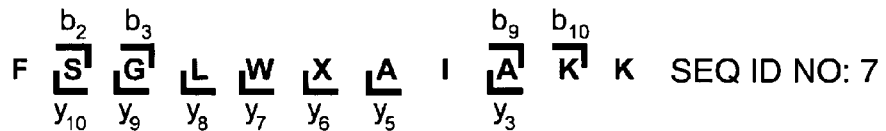
FIG. 27 (A) shows the results of MS/MS sequencing of a $pNO_2Phe$-containing tryptic fragment of $pNO_2Phe^{43}$ mRBP4. (B) shows the results of MS/MS sequencing of a $pNO_2Phe$-containing tryptic fragment of $pNO_2Phe^{108}$mRBP4.
Figure 27B:
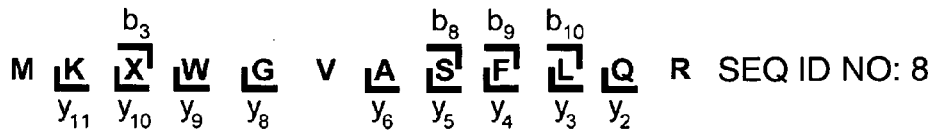

FIG. 27A provides the results of MS/MS sequencing of a pNO$_2$Phe-containing tryptic fragment of pNO$_2$Phe$^{43}$ mRBP4. The sequence of the tryptic fragment containing pNO$_2$Phe is shown in single letter code (X, pNO$_2$Phe). Observed fragment ions of the y and b series are indicated. Key y and b ions proving the incorporation of pNO$_2$Phe are represented in red. All masses are reported as monoisotopic masses. FIG. 27B provides the results of MS/MS sequencing of a pNO$_2$Phe-containing tryptic fragment of pNO$_2$Phe$^{108}$ mRBP4. The sequence of the tryptic fragment containing pNO$_2$Phe is shown in single letter code (X, pNO$_2$Phe). Observed fragment ions of the y and b series are indicated. Key y and b ions proving the incorporation of pNO$_2$Phe are $b_9$, $b_{10}$, $y_{10}$, $y_9$, $y_8$, $y_7$, and $y_6$. All masses are reported as monoisotopic masses.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of producing or enhancing an immunological response in a subject against a target moiety, wherein the target moiety is TNFα, the method comprising:

providing an unnatural immunogen, which unnatural immunogen comprises one or more unnatural amino acids, wherein the unnatural immunogen is an unnatural mTNFα, and the one or more unnatural amino acids is or are selected from the group consisting of: a $pNO_2Phe^{11}$-mTNFα, a $pNO_2Phe^{19}$-mTNFα, a $pNO_2Phe^{21}$-mTNFα, a $pNO_2Phe^{42}$-mTNFα, a $pNO_2Phe^{49}$-mTNFα, a $pNO_2Phe^{86}$-mTNFα, a $pNO_2Phe^{104}$-mTNFα, a $pNO_2Phe^{113}$-mTNFα; or wherein the unnatural immunogen is an unnatural hTNFα, and the one or more unnatural amino acids is or are selected from the group consisting of: a $pNO_2Phe^{11}$-hTNFα, a $pNO_2Phe^{19}$-hTNFα, a $pNO_2Phe^{21}$-hTNFα, a $pNO_2Phe^{42}$-hTNFα, a $pNO_2Phe^{49}$-hTNFα, a $pNO_2Phe^{87}$-hTNFα, a $pNO_2Phe^{105}$-hTNFα, and a $pNO_2Phe^{114}$-hTNFα;

wherein the $pNO_2Phe$ unnatural amino acid residues are numbered relative to the mature mTNFα and hTNFα polypeptides; and, administering the unnatural immunogen to the subject, wherein the subject produces one or more antibodies against the unnatural immunogen, which antibodies are cross-reactive against TFNα;

thereby producing or enhancing the immunological response against TFNα.

2. The method of claim 1, wherein the immunological response comprises a B-cell mediated response and/or a T-cell mediated response.

3. The method of claim 1, wherein providing an unnatural immunogen comprises producing the unnatural immunogen in an orthogonal translation system.

4. The method of claim 1, wherein the subject is selected from the group consisting of: humans, monkeys, mice, rats, pigs, cows, chickens, cage birds, aviary birds, reptiles, and amphibians.

5. The method of claim 1, wherein the target moiety comprises a polypeptide and/or a carbohydrate.

6. The method of claim 1, wherein the target moiety is a self-moiety of the subject.

7. The method of claim 1, wherein the one or more cross-reactive antibodies are specific for an epitope on the target moiety which comprises a same sequence as compared to the corresponding epitope on the unnatural immunogen.

8. The method of claim 1, wherein the one or more cross-reactive antibodies are specific for an epitope on the target moiety which comprises a different sequence as compared to the corresponding epitope on the unnatural immunogen.

9. The method of claim 8, wherein the different sequence on the corresponding epitope on the unnatural immunogen comprises one or more unnatural amino acid.

10. The method of claim 1, wherein the one or more unnatural amino acids are antibody accessible.

11. The method of claim 1, wherein the unnatural immunogen comprises a substantially similar structure to the target moiety.

12. The method of claim 1, wherein the unnatural immunogen comprises a substantially similar tertiary and/or quaternary structure to the target moiety.

13. The method of claim 1, wherein the subject is a mouse, the target moiety is mTNFα, and the immunogen is an unnatural mTNFα.

14. The method of claim 13, wherein the unnatural mTNFα comprises $pNO_2Phe^{86}$-mTNFα.

15. A method of producing a vaccine, the method comprising:
identifying a target moiety for antibody therapy, wherein the target moiety is TNFα, which target moiety does not comprise an unnatural amino acid,
providing an unnatural immunogen, which unnatural immunogen comprises one or more unnatural amino acids, and which unnatural immunogen is structurally similar to the target moiety such that when administered to a subject, the subject will produce antibodies against the unnatural immunogen that are cross-reactive against the target moiety, wherein the unnatural immunogen is an unnatural mTNFα, and the one or more unnatural amino acids is or are selected from the group consisting of: a $pNO_2Phe^{11}$-mTNFα, a $pNO_2Phe^{19}$-mTNFα, a $pNO_2Phe^{21}$-mTNFα, a $pNO_2Phe^{42}$-mTNFα, a $pNO_2Phe^{49}$-mTNFα, a $pNO_2Phe^{86}$-mTNFα, a $pNO_2Phe^{104}$mTNFα, a $pNO_2Phe^{113}$-mTNFα; or
wherein the unnatural immunogen is an unnatural hTNFα, and the one or more unnatural amino acids is or are selected from the group consisting of: a $pNO_2Phe^{11}$-hTNFα, a $pNO_2Phe^{19}$-hTNFα, a $pNO_2Phe^{21}$-hTNFα, a $pNO_2Phe^{42}$-hTNFα, a $pNO_2Phe^{49}$-hTNFα, a $pNO_2Phe^{87}$-hTNFα, a $pNO_2Phe^{105}$-hTNFα, and a $pNO_2Phe^{114}$-hTNFα;
wherein the $pNO_2Phe$ unnatural amino acid residues are numbered relative to the mature mTNFα and hTNFα polypeptides; and,
admixing the unnatural immunogen with one or more pharmaceutically acceptable adjuvant, carrier or excipient, thus producing the vaccine.

16. The method of claim 1, further comprising incorporating the one or more unnatural amino acids into the unnatural immunogen during synthesis of the immunogen.

17. The method of claim 1, further comprising incorporating the one or more unnatural amino acids into the unnatural immunogen through a process other than post-translational modification or post-synthesis chemical modification.

18. The method of claim 1, further comprising incorporating the one or more unnatural amino acids into the unnatural immunogen through one or more of:
orthogonal translation; in vitro translation; native chemical ligation; expressed protein ligation; or solid-phase synthesis.

19. The method of claim 1, wherein the one or more amino acids is nitrated by a process other than post-translational modification or by a process other than chemical modification.

20. The method of claim 1, wherein the subject is suffering from a disease state selected from the group consisting of: endotoxic shock, cerebral malaria, autoimmune disorders, multiple organ failure, multiple sclerosis, cardiac dysfunction, atherosclerosis, ischemia-reperfusion injury, insulin resistance, rheumatoid arthritis, inflammatory bowel disease, cachexia, AIDS, graft-versus-host disease, bactericidal granulomas, adult respiratory distress syndrome, and/or silica-induced pulmonary fibrosisseptic shock, and Crohn's disease.

* * * * *

SEQUENCE LISTING

<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 1
atatacatat gctcagatca tcttctcaaa attcg                          35

<210> SEQ ID NO 2
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 2
aacaacctcg agttatcaca gagcaatgac tccaaagt                       38

<210> SEQ ID NO 3
<211> LENGTH: 31
<212> TYPE: DNA
<213> ORGANISM: Artificial Sequence
<220> FEATURE:
<223> OTHER INFORMATION: Oligonuclotide primer

<400> SEQUENCE: 3
ctgtacttcc agggcgagcg cgactgcagg g                              31

<210> SEQ ID NO 4
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 4
aattaagtcg cgttacaaac tgtttctgga gggcc                          35

<210> SEQ ID NO 5
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 5
gccctggaag tacaggtttt cgtgatgatg atgatgatg                      39

<210> SEQ ID NO 6
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 6
taacgcgact taattaactc gtttaaacgg tctccagc                       38

<210> SEQ ID NO 7
<211> LENGTH: 11
<212> TYPE: PRT

```
<213> ORGANISM: Artificial Sequence
<220> FEATURE:
<223> OTHER INFORMATION: 11 amino acid fragment of mRBP4
<220> FEATURE:
<221> NAME/KEY: Xaa
<222> LOCATION: (6)..(6)
<223> OTHER INFORMATION: Xaa = p-nitrophenylalanine

<400> SEQUENCE: 7

Phe Ser Gly Leu Trp Xaa Ala Ile Ala Lys Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: 12 amino acid fragment of mRBP4
<220> FEATURE:
<221> NAME/KEY: Xaa
<222> LOCATION: (3)..(3)
<223> OTHER INFORMATION: Xaa = p-nitrophenylalanine

<400> SEQUENCE: 8

Met Lys Xaa Trp Gly Val Ala Ser Phe Leu Gln Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: 8 amino acid tryptic fragment of TNFalpha
<220> FEATURE:
<221> NAME/KEY: Xaa
<222> LOCATION: (5)..(5)
<223> OTHER INFORMATION: Xaa = p-nitrophenylalanine

<400> SEQUENCE: 9

Phe Ala Ile Ser Xaa Gln Glu Lys
1               5
```